United States Patent [19]

Sioud

[11] Patent Number: 5,864,028
[45] Date of Patent: Jan. 26, 1999

[54] DEGRADATION RESISTANT MRNA DERIVATIVES LINKED TO TNF-α RIBOZYMES

[75] Inventor: Mouldy Sioud, Oslo, Norway

[73] Assignee: Gene Shears Pty. Limited, New South Wales, Australia

[21] Appl. No.: 464,073

[22] Filed: Jun. 5, 1995

Related U.S. Application Data

[63] Continuation-in-part of Ser. No. 428,252, Jun. 22, 1995, which is a continuation-in-part of Ser. No. 971,058, Nov. 3, 1992, abandoned.

[51] Int. Cl.[6] .......................... C07H 21/00; C07H 21/02; C12Q 1/60
[52] U.S. Cl. ...................... 536/23.1; 536/24.1; 536/24.5; 435/91.31; 435/6
[58] Field of Search .............................. 435/6, 69.1, 91.3, 435/91.31, 172.3, 290.2; 514/44, 2; 536/23.1, 23.2, 23.5, 24.5, 24.1; 530/350

[56] References Cited

U.S. PATENT DOCUMENTS

| | | | |
|---|---|---|---|
| 4,666,848 | 5/1987 | Gelfand et al. | 435/252.33 |
| 5,107,065 | 4/1992 | Shewmaker et al. | 800/205 |
| 5,149,635 | 9/1992 | Gillies | 435/69.1 |

FOREIGN PATENT DOCUMENTS

| | | |
|---|---|---|
| 8905852 | 6/1989 | WIPO . |
| 9207065 | 4/1992 | WIPO . |

OTHER PUBLICATIONS

Stull et al "Antigene, Ribozyme and Aptanes Nucleic Acid Drugs: Progress and Prospects." *Pharmaceutical Research* vol. 12, No. 4 1995 pp. 465–483.

Baralle, F.E. (1983) The Functional Significance of Leader and Trailer Sequences in Eukaryotic mRNAs. International Rev. of Cytology 81:71–106.

Beutler, B. and Cerami, A. (1989) The Biology of Cachectin/TNF–A Primary Mediator of the Host Response. Ann. Rev. Immunol. 7:625–655.

Elela, S.A. and Nazar, R.N. (1992) Extended Secondary Structure as a Basis of Increased RNA Stability in a thermophilic alga Cyanidium caldarium. Biochimica et Biophysica Acta. 130:339–342.

Haseloff, J. and Gerlach, W.L. (1988) Simple RNA Enzymes with New and Highly Specific Endoribonuclease Activities. Nature 334:585–591.

Hsu, Y.–P. and Schimmel, P. (1984) Yeast LEU1, J. Biol. Chem. 259(6):3714–3719.

Nielsen, D.A. and Shapiro, D.J. (1990) Insights into Hormonal Control of Messenger RNA Stability, Mol. Endo. 4(7):953–957.

Perreault, J. et al. (1990) Mixed deoxyribo–and ribo–oligonucleotides with catalytic activity. Nature 344:565–567.

Proudfoot, N.J. and Brownlee, G.G. (1976) 3' Non–coding Region Sequences in Eukaryotic Messenger RNA. Nature 263:211–214.

Ross, H.J. et al. (1991) Cytokine Messenger RNA Stability is Enhanced in Tumor Cells, Blood 77(8):1787–1795.

Rossi, J.J. et al. (1992) Ribozymes as Anti–HIV–1 Therapeutic Agents: Principles, Applications, and Problems. AIDS Research and Human Retroviruses 8(2):183–189.

Saini, K.S. et al. (1990) Molecular Events Regulating Messenger RNA Stability in Eukaryotes. Mol. and Cell. Biochem. 96:15–23.

Untranslated Region of GM–CSF mRNA Mediates Selective mRNA Degradation. Cell 46:659–667.

Sioud, M. and Drlica, K. (1991) Prevention of Human Immunodeficiency Virus Type I Integrase Expression in *Escherichia coli* by a Ribozyme. Proc. Natl. Acad. Sci. U.S.A. 88:7303–7307.

Sioud, M. et al. (1992) Preformed Ribozyme Destroys Tumor Necrosis Factor mRNA in Human Cells, J. Mol. Biol. 223:831–835; and.

Zaret, K.S. and Sherman, F. (1984) Mutationally Altered 3' Ends of Yeast CYC1 mRNA Affect Transcript Stability and Translational Efficiency. Mol. Biol. 176:107–135.

*Primary Examiner*—George C. Elliott
*Assistant Examiner*—Sean M. Garry
*Attorney, Agent, or Firm*—John P. White; Cooper & Dunham LLP

[57] ABSTRACT

This invention describes compounds active against TNF-α mRNA. It further describes RNA molecules capable of conferring stability to RNA in vivo through an endogenous ribozyme binding protein(s). Possible mRNA molecules to be stabilized include ribozymes, antisense molecules and mRNA encoding polypeptides useful for protein production. The ribozymes and antisense molecules described herein are useful in mammals and plants, particularly suited for viral diseases. Methods of production and methods of use are also described.

5 Claims, 51 Drawing Sheets

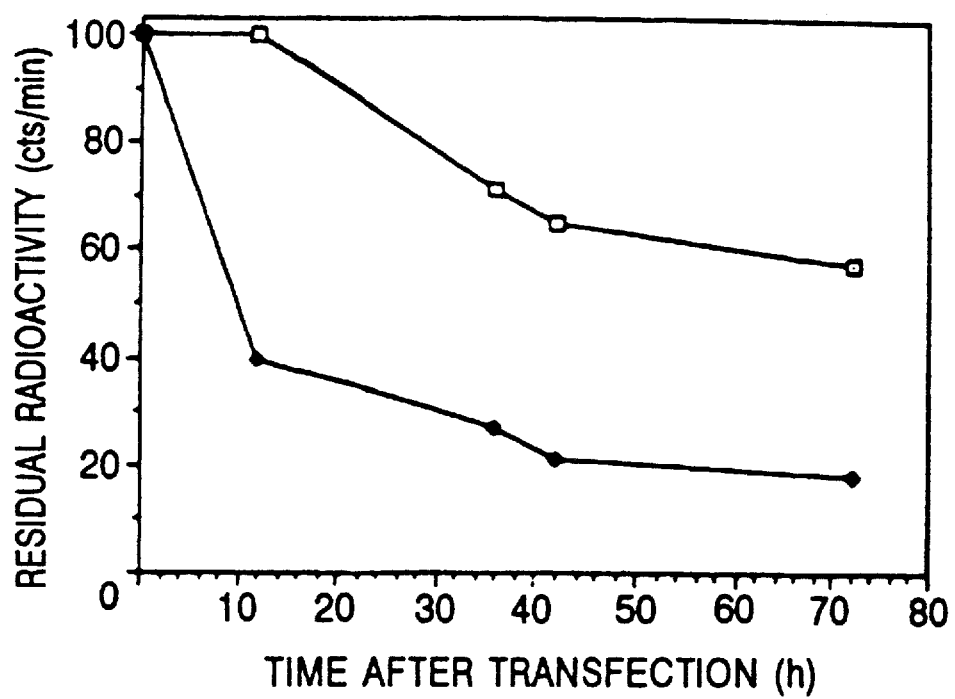

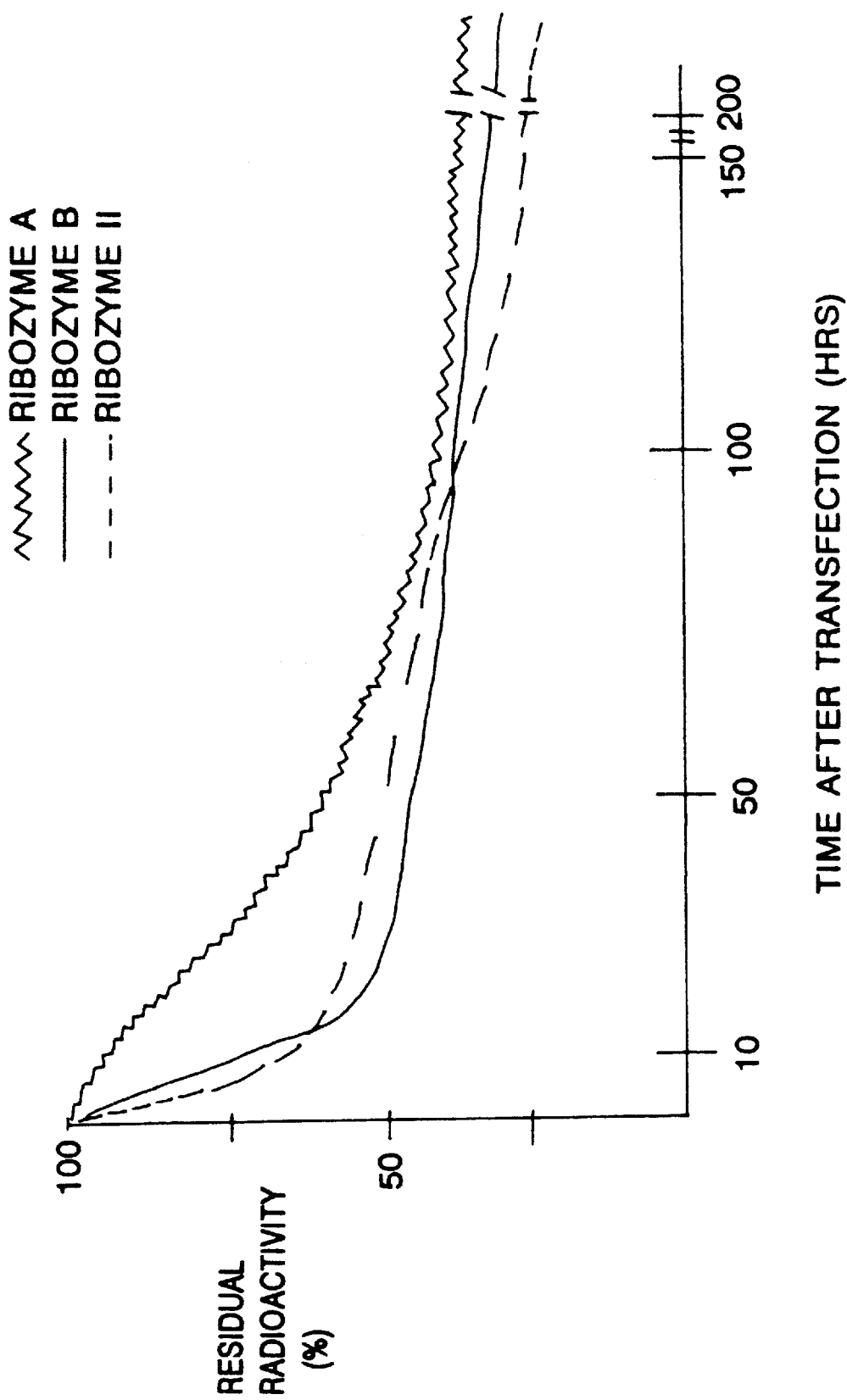

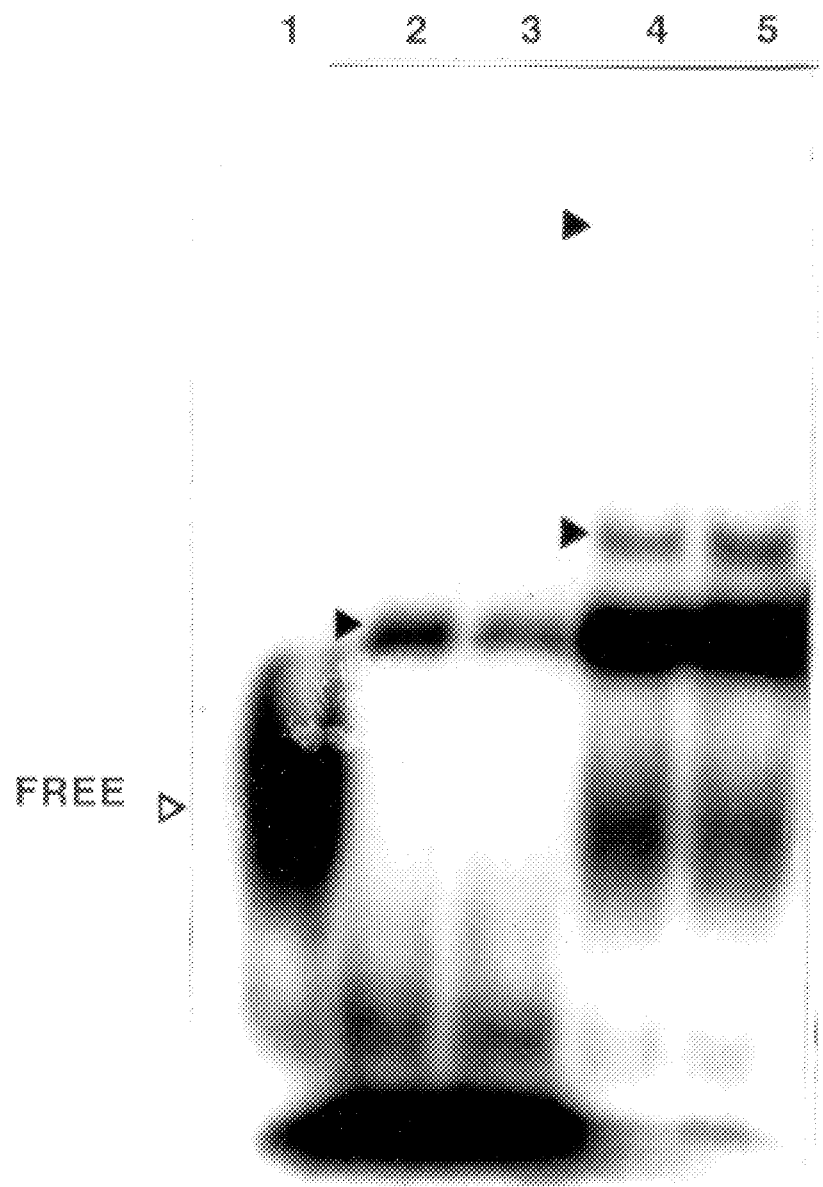

INTERLEUKIN 2
RIBOZYME (IL2R)

IL2R LINKED
TO TNFα R

IL2R LINKED TO
TNFα ANTISENSE

FIGURE 12A
FIGURE 12B
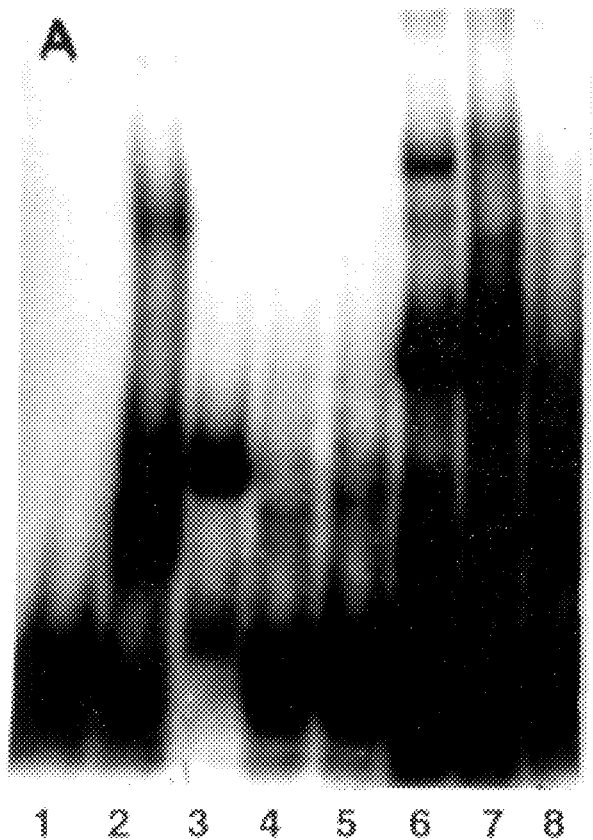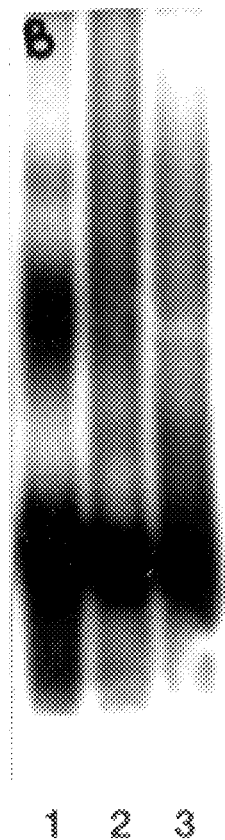

FIGURE 13A

```
        10                  20
GUAAGAUGAUCUCUGAUGA         G
                       GUCC  U
                       CAGG  G
- - - - - - - - - UUAAGUUUU  A
                 90        30
                                   40          50          60
                            GAAACUGCCUGGUACU                    CU
                                        AACCCCUUGGGGCCU  A
                                        UUGGGGAGUUCUGGG  A
                            - - - - - - - - - - - - - - -      CA
                                             80         70
```

FIGURE 13B

```
        10          20          30
GUAAGAUGAUCUCUGAUG   C           ACGA
                AGU  CGUG  AGG
                UUA  GUAC  UCC      A
- - - - - - - - - -       A        GUCA
                 90        40
                                    50          60
                                         CAGC      ACG
                               GGUACUGAAGC    UCC
                                    *
                               UCGUGACUUUCG    AGG    U
                                          UACU   CCC
                                          80      70
```

FIGURE 14A
FIGURE 14B
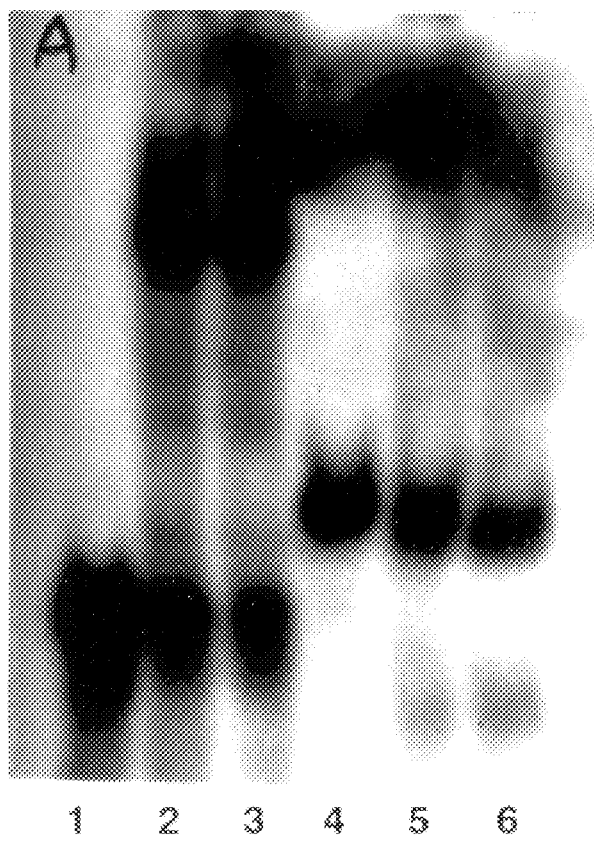
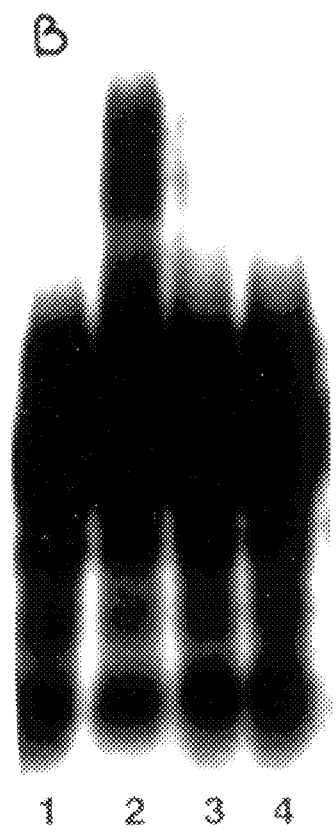

FIGURE 15A

```
          10             20            30
GACUUAGUGCAA        GA    ---A      G
         UGCAACU  UG       GUCC  U
         GCGUUGA  AC       CAGG  G
--------UUAA        GG    AAAG      A
              50             40
```

FIGURE 15B

```
          10
GUAAGA     A    -    AUG
       UG UCUC UG
       GC GGAG GC     A
--UUAA     A    U    CUG
       30            20

40
AAAC        -    -      AUGA
      UGC CUG GU         A
      ACG GAU CA         A
----        U    U      GAAA
            60           50

70            80
          A        GA   ---A      G
       UGCAACU  UG       GUCC  U
       GCGUUGA  AC       CAGG  G
       -          GG    AAAG      A
              100           90
```

FIGURE 17A

```
              10              20
   GCU    -G   -    -UG   GAC
      GAU    AGU CCG    AG
      UUA    UCA GGU    UC    G
   ---    AA    U    CCG   AAA
      40            30
```

FIGURE 17B

```
           10           20
  GUAAGAUGAUC    GAUGA       G
             UCU        GUCC  U
             AGA        CAGG  G
  --------UUA    ---AG       A
                          30
```

---- THE POTENTIAL BINDING SITE FOR THE PROTEIN(S)

IL2: IL2 RIBOZYME

IL2-TNFα: IL2 RIBOZYME LINKED TO
3' END OF TNFα RIBOZYME

R2 = TNFα RIBOZYME
RA = ANTISENSE LINKED TO TNFα RIBOZYME

C = CONTROL
R2 = TNFα RIBOZYME
RA = ANTISENSE LINKED TO TNFα RIBOZYME

FIGURE 25A
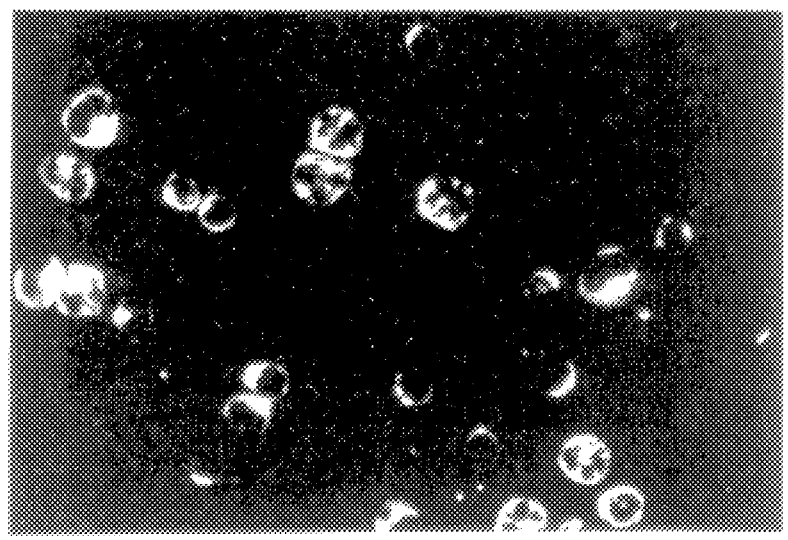
FIGURE 25B

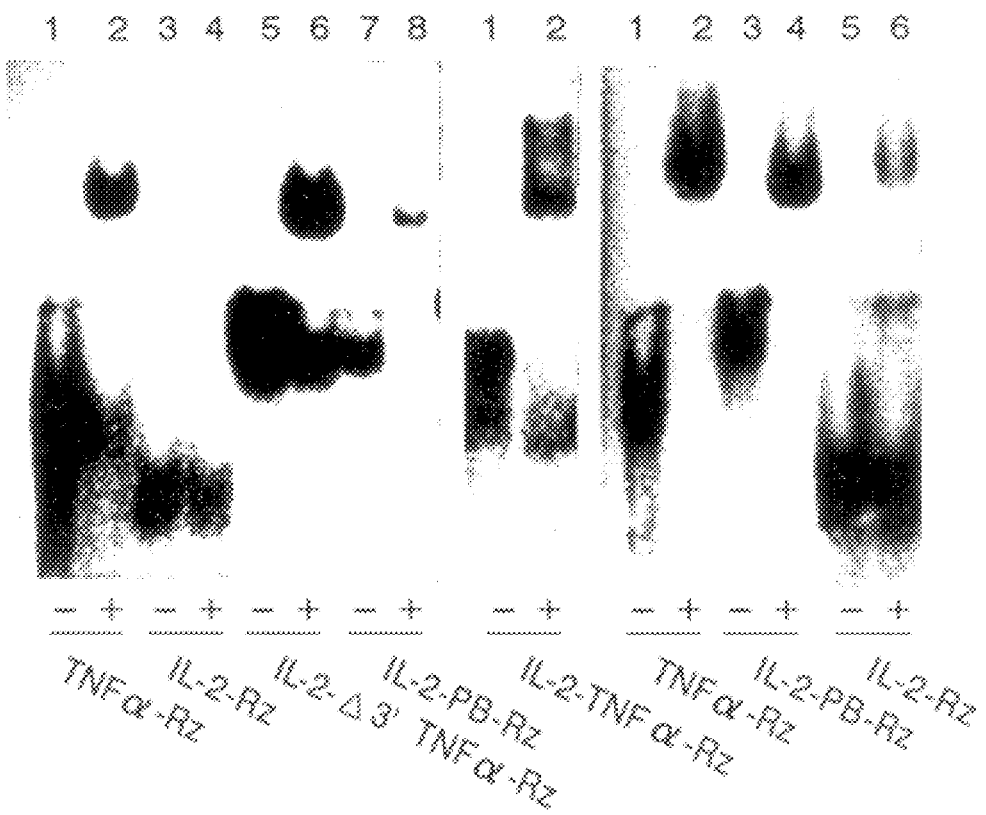

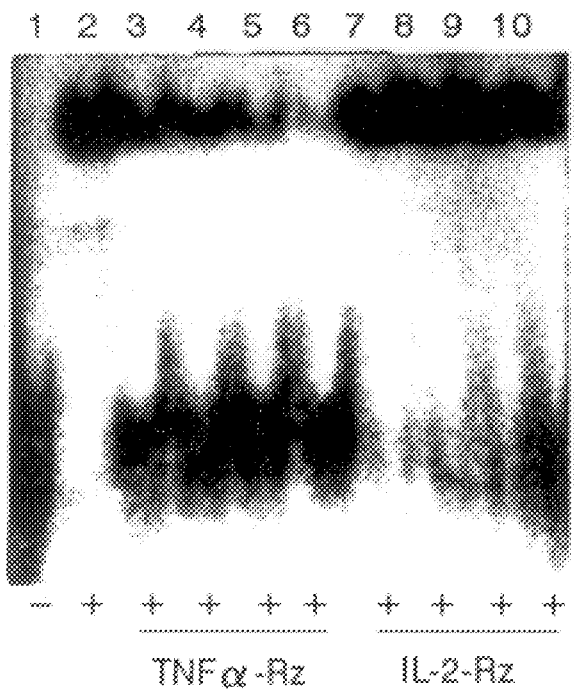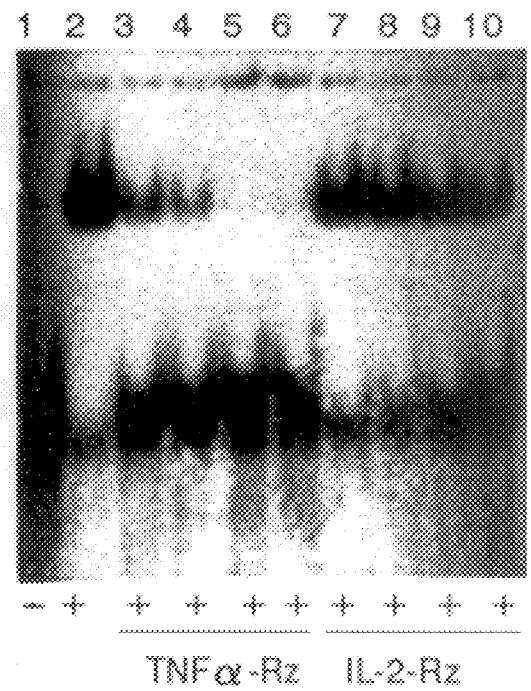

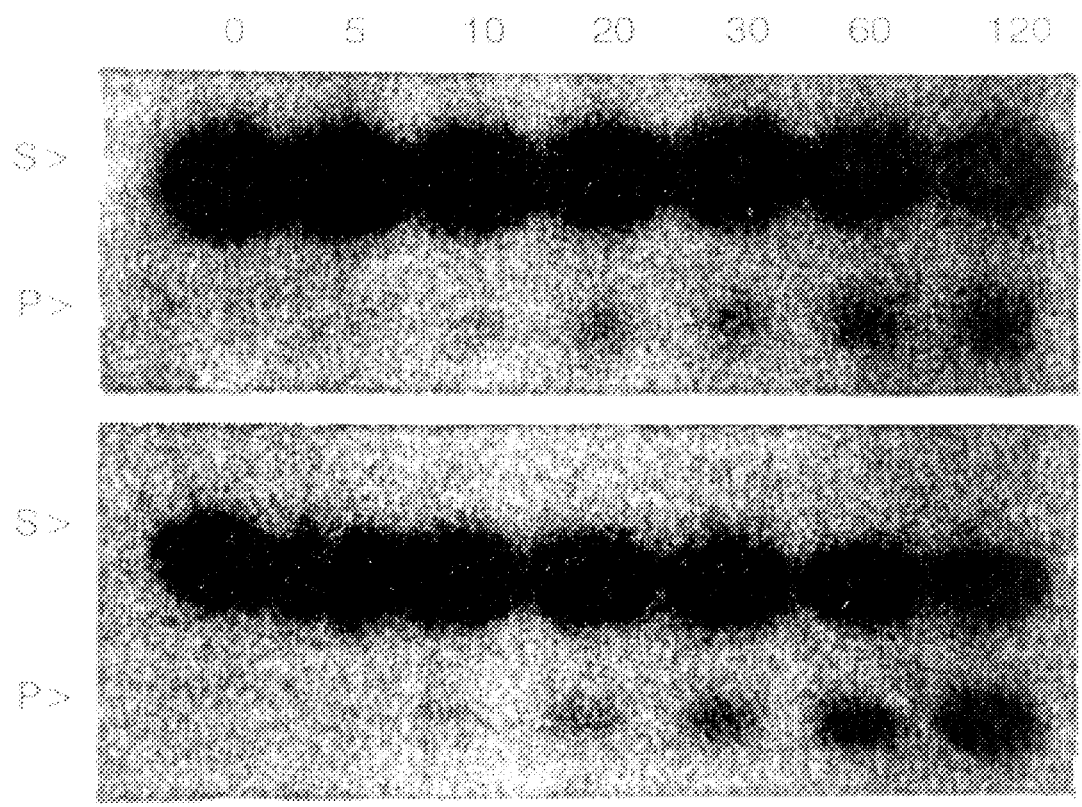

```
5' GGUGCAAUGCAA    AUGA     G
              CUG      GUCC U
              GAC      CAGG G   IL-2-Rz1
3' -----UUAAGAG    AAAG     A
```

```
5' GGUGCAA          GA  ---A     G
          UGCAACU  UG      GUCC U
          GCGUUGA  AC      CAGG G   IL-2-Rz2
3' ---UUAA          GG      AAAG     A
```

```
5' GACUUAGUGCAA       GA  ---A     G
             UGCAACU UG      GUCC U
             GCGUUGA AC      CAGG G   IL-2-Rz3
3' --------UUAA       GG      AAAG     A
```

- - - - DNA part

IL-2-PB-Rz

FIGURE 35A
```
            CC      A        AU
          AGGC  GUCAG
          UCCG  CAGUC    C
          --      A        UA
```

FIGURE 35B
1     2     3     4
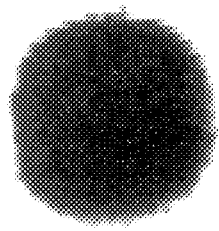 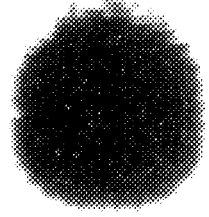 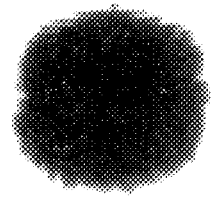 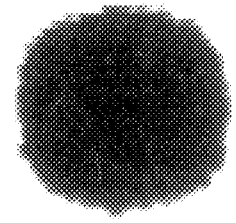
  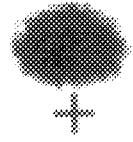
             −       +       +

DEGRADATION RESISTANT MRNA DERIVATIVES LINKED TO TNF-α RIBOZYMES

This application is a continuation-in-part of U.S. Ser. No. 08/428,252, filed Jun. 22, 1995, which corresponds to International Application No. PCT/AU 93/00567, filed Nov. 3, 1993 which is a continuation-in-part of U.S. Ser. No. 07/971,058, filed Nov. 3, 1992 and now abandoned.

BACKGROUND OF THE INVENTION

Throughout this application, various publications are referred to within brackets. The disclosures for these publications in their entireties are hereby incorporated by reference into this application to more fully describe the state of the art to which this invention pertains.

The discovery of catalytic RNA molecules that possess enzymatic, self-cleaving activity (ribozymes) has provided a new way to artificially control gene expression (Foster & Symons, (1987) Cell, 49:585–591). Ribozymes have been designed that contain sequences required for the cleavage of particular RNA sequences. For the hammerhead type of ribozyme, the target RNA needs to contain only the sequence XUX with cleavage occurring 3' from XUX (Haseloff & Gerlach, (1988) Nature, (London) 334:585–591; Perriman et al., Gene (1992) 113:157–163). High specificity and limited target requirement give these catalytic RNA molecules the potential to inhibit viral pathogens and to regulate specific gene expression by interfering with transcription in a highly specific manner (Uhlenbeck, (1987) Nature (London) 328:596–600; Haseloff & Gerlach, (1988) Nature, (London) 334:585–591).

Several reports indicate that a hammerhead type of ribozyme functions in living cells. Cotten & Birnstiel (1989, EMBO J., 8:3861–3866) and Cameron & Jennings (1989, Proc. Natl. Acad. Sci., USA 86:9139–9143) have reported ribozy-memediated destruction and an inhibition of specific gene expression in *Xenopus laevis* oocytes and monkey (COS1) cells. Sarver et al. (1990, Science, 247:1222–1225) showed that a ribozyme directed against HIV-1 gag RNA reduced p24 antigen expression in CD4$^+$ HeLa cells. Recently, this line of study was extended to bacterial cells by showing that a ribozyme designed to cleave the integrase gene of HIV-1 is effective when transcribed from a plasmid in *Escherichia coli*. Integrase RNA was eliminated and integrase protein synthesis was blocked (Sioud & Drlica, (1991) Proc. Natl. Acad. Sci., USA 88:7303–7307). Since ribozymes are effective in vivo, problems of ribozyme stability and delivery may now be addressed.

To interfere with tumor necrosis factor-α (TNF-α) gene expression we have used cationic liposome-mediated transfection (Malone et al., (1989) Proc. Natl. Acad. Sci., USA 86:6077–6081) to deliver a ribozyme directed against TNF-α into human promyelocytic leukaemia cells (HL60) and peripheral blood mononuclear cells (PBMNC). TNF-α plays an important role in many inflammatory rheumatic diseases (Shinmei et al., (1989) Sem. Arth. Rheum. 18 (suppl. 1) 27–32), and it modulates the expression of several proteins, including the Class I antigens of the major histocompatibility complex (MHC) and cytokines such as interleukin-1 and interleukin-6 (Beutler & Cerami, (1988) Annu. Rev. Biochem. 57:505–518 and (1989) Annu. Rev. Immunol. 7:625–655). TNF-α also appears to be necessary for normal immune responses, however large quantities of it can produce destructive effects such as rheumatoid arthritis (Brennan et al., (1989) Lancet ii 244–247). TNF-α is the cytokine responsible for the induction of HIV-1 expression in ACH-2 cells (Rosenberg & Fauci, (1990) Immunol. Today 11:176–180). TNF-α induces the production of cellular factors that bind to the NF-KB enhancer elements within the viral long terminal repeat sequences and thereby activates HIV-1 expression.

The effectiveness of catalytic RNA molecules is dependent on the stability of the mRNA in vivo. Compared to the current knowledge of DNA structural elements, relatively little is known about mRNA stability elements. mRNA half-lives range from less than 30 minutes for fibroblast interferon and c-fos to greater than 17 hours for β-globin MRNA. Most eukaryotic mRNAs are protected from exonuclease attack by the 5' cap structure and the 3'poly(A) tail and poly(A) binding proteins. Eukaryotic mRNAs have both 5' and 3' non-coding regions on either side of the coding region. The 5' non-coding region is involved in the rate of initiation of translation of the mRNA to protein. The 3' non-coding region serves to initiate the formation of the poly(A) and can act to stabilize mRNA (Baralle, F. E., Int. Rev. of Cytology (1983) 81:71–106). In particular, 3' non-coding iron-responsive elements have been identified that can modulate mRNA stability in the presence of iron. Another characterized motif is the AUUUA element responsible for the rapid degradation of some cellular mRNAs, particularly cytokine mRNAs. (Saini, K. S. et al., Mol. Cel. Biochem. (1990) 96:15–23; Ross, H. J. et al., Blood (1991) 77:1787–1795). Some have postulated that an initial endonuclease attack is required before rapid degradation can take place (Nielson, D. A. and Shapiro, D. J., Mol. Endocrinology (1990) 4:953–957).

There is a need for a method to extend the half-life of particular mRNAs in vivo and increase protein levels as well as to control and reduce gene expression with oligonucleotides (e.g., antisense and triple helix) in plants and animals. The stabilization of mRNA elements can be effected through the use of ribozymes as well as antisense oligonucleotides.

SUMMARY OF THE INVENTION

This invention describes compounds active against TNF-α mRNA. It further describes RNA molecules capable of conferring stability to RNA in vivo through an endogenous protein(s) Possible target RNA molecules to be stabilized include ribozymes, antisense molecules, mRNA encoding polypeptides useful for protein production and other cellular RNA. The ribozymes and antisense molecules described herein are useful in mammals and plants, particularly suited for viral diseases. Methods of production and methods of use are also described.

Ribozyme A is composed of a conserved ribozyme sequence as described by Haseloff & Gerlach (1988). The 5' and 3' flanking sequences are complementary to the TNF-α RNA nucleotides 374 and 393 (see Pennica et al., (Nature (1984) 312:724–729) for numbering) and bacteriophage T7 transcription terminator with CU mispair (C) (Rosenberg et al., Gene (1987) 56:125–135). Ribozyme B is identical to A except that it lacks the T7 transcription terminator. Ribozyme II is a shortened version of ribozyme B with 9 and 11 basepair hybridizing arms. Antisense RNA is identical to ribozyme A except that it has a single guanosine nucleotide in place of the catalytic domain. The anti-TNF-α hammerhead catalytic gene and antisense RNA control were made as described by Sioud & Drlica ((1991) Proc. Natl. Acad. Sci., USA 88:7303–7307). Briefly, two overlapping half oligonucleotides containing the sequences of a bacteriophage T7 RNA polymerase promoter, the 5' and 3' recognition sequences of the ribozyme, the catalytic domain and the T7 transcription terminator were synthesized (an XbaI restriction site was introduced between the T7 terminator and the 3' end of the ribozyme, and PvuII and XhoI sites at the 5' and 3' ends of the ribozyme sequences, respectively), hybridized and then extended with the Klenow fragment of DNA polymerase. Following the extension, DNA was extracted with phenol, precipitated with ethanol, gel purified and then cloned into a SmaI cleaved pUC 18 vector. The sequences of the overlapping primers (Public Health Research Institute, New York 10016, N.Y.) were used as follows:

(1) Ribozyme primers (SEQ ID NO:19–22):

5'AACAGCTGTAATACGACTCACTATAGAG-TACTAAGATGATCTCTGATGAGTCCGTG AGGAC-GAAACTGC3' and

5'TTCTCGAGAAAAAACCCTCAAGAC-CCGTTTAGAGGCCCCAAGGGGTTATGTCTAGA CCAGGCAGTTTCGTCC3'

(2) Antisense primers:

5'AACAGCTGTAATACGACTCACTATAGAG-TACTAAGATGATCTGACTGCCTGGTCTA G3' and

5'TTCTCGAGAAAAAACCCTCAAGAC-CCGTTTAGAGGCCCCAAGGGGTTATGTCTAGA CCAGCA3'.

The underlined sequences in the figure indicate the presence of restriction sites in the DNA template. Ribozyme II, unlike ribozyme A and B, lacks these sequences. Therefore, the restriction sequences are not required for stability. All three of these ribozymes are stable in vivo and bind protein.

Figure 2A:
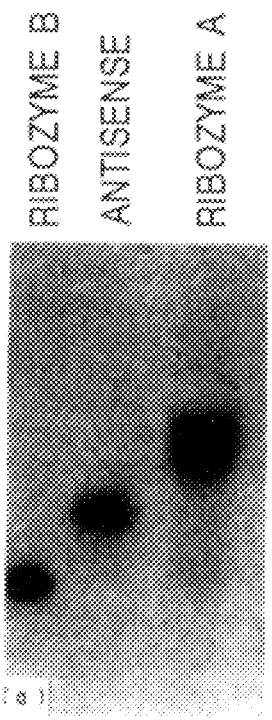
Figure 2B:
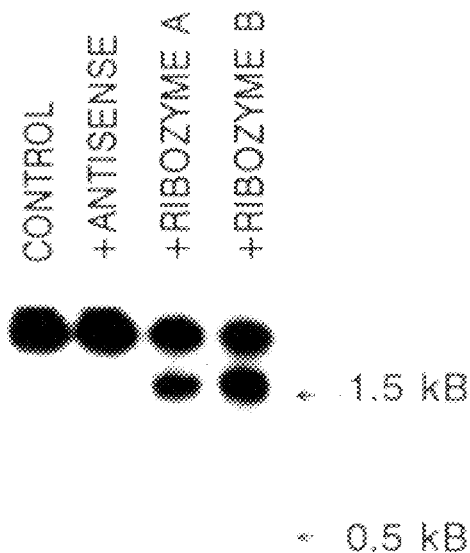

FIG. 2A–2B: (A) In vitro RNA transcripts and (B) In vitro activity

FIG. 2(A) In vitro transcription of ribozymes A, B and TNF-α antisense. Ribozymes and antisense RNA were transcribed with T7 RNA polymerase from PAGE-purified template DNA fragments cleaved from recombinant plasmids as described by (Uhlenbeck, O., Nature (1987) 328:596–600). RNA was labelled internally with [α$^{32}$P]CTP during transcription. Transcription was primed with 7-methyl guanosine (5') triphospho (5') guanosine in all cases. Transcripts were treated with DNAse (RNAse-free), extracted with phenol, precipitated with ethanol and then analyzed by electrophoresis in a 15% polyacrylamide gel containing 7M-urea. The lengths of ribozymes A, B and antisense are 97, 49 and 76 nucleotides, respectively. FIG. 2(B) Cleavage of TNF-α RNA in vitro. PBMNC cells were stimulated with PMA and Con-A to express TNF-α protein. Whole cell RNA was extracted and the RNA (20 μg) was incubated with 1 μg of either ribozyme or antisense RNA for 60 min at 50° C. RNA species were then separated by gel electrophoresis and TNF-α RNA was identified by Northern blotting (kb=10$^3$ bases).

Figure 3A:
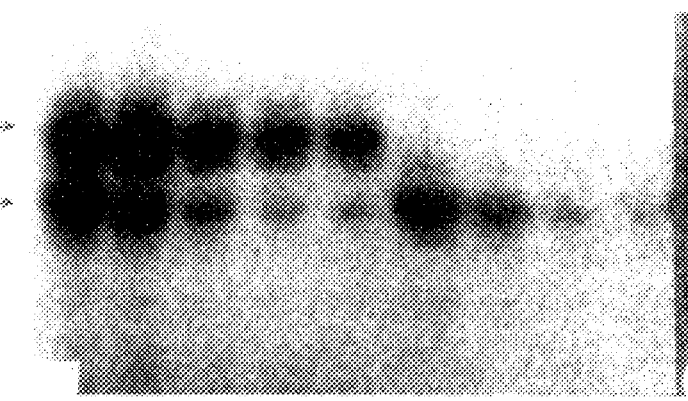
Figure 3B:

FIG. 3A–3C: Ribozyme stability following transfection.

The effect of bacteriophage T7 transcription terminator on RNA stability was analyzed by cotransfecting HL60 cells with ribozymes A and B. Total RNA was extracted and analyzed by electrophoresis in 15% (w/v) polyacrylamide gels containing 7M-urea. While ribozyme A could be detected more than 72 hours post transfection, the amount of ribozyme B progressively declined (FIG. 3A). The radioactivity contained in each band was then determined, and the results were expressed as the percentage of the radioactivity at zero time. FIG. 3C shows that ribozyme B decays more rapidly than ribozyme A. The residual radioactivity for ribozymes A and B, 72 hours post transfection, was 57% and 18% respectively. The stability of the antisense RNA control (ribozyme A lacking the catalytic domain) is similar to ribozyme A (data not shown). Thus, the addition of a bacteriophage T7 terminator to the 3' end of a ribozyme increases it stability.

The compartmentalisation of ribozyme A in HL60 cells was also studied by analysis of cytoplasmic and nuclear RNAs. As shown in FIG. 3B (lanes N and C), ribozyme A is preferentially localized to the nucleus.

Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 μl) of serum free medium was added to polystyrene tubes followed by 35 μg of lipofectin (Bethesda Research Laboratories), 10 μg of carrier RNA (E. coli. tRNA), 3×10$^6$ disints/min of $^{32}$P-labelled capped ribozyme A, B or antisense RNA (5 μg). The tubes were immediately mixed. The cells were resuspended in a mixture of serum-free medium lipofectin/RNA/carrier RNA and returned to the incubator for 20 h. Following transfection, cells were washed 3 times with Hank's buffered saline solution and then returned to the incubator with RPMI supplemented with 20% FCS. Cells (10$^6$) were harvested at the times indicated above each lane, and total RNA was prepared and analyzed by 15% polyacrylamide gel with 7M-urea. The RNA samples used for transfection are indicated at the top of FIG. 3. Ribozyme B alone serves as a marker to indicate its position in co-transfection experiments. (B) Analysis of nuclear (N) and cytoplasmic (C) RNA. A sample (50 μM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris-HCl (pH 7.5), 5 mM-KCl, 140 mM-NaCl, 5 mM-dithiothreitol and 0.49% (w/v) Nonidet P40 for 10 min at 4° C. and the nuclei were collected by centrifugation at 800 g for 5 min. RNA in the supernatant fluid was precipitated and saved as the cytoplasmic fraction. The nuclei were processed as described by Chomezynski & Sacchi (1987, Anal. Biochem. 162:156–160) for total RNA preparation. The arrow indicates the position of ribozyme A monomer. (C) One experiment showing RNA quantification. The run amount of radioactivity in the ribozyme bands shown in (A) was determined and expressed as a percentage of the radioactivity present immediately after 20 h transfection time. (□ Ribozyme A: ◆ ribozyme B.)

FIG. 4: Stability of ribozyme A, B and II in HL60 cells.

The results shown are derived from the mean of more than 50 experiments. Ribozymes were introduced to the cells using DOTMA cationic liposome-mediated transfection. Following transfection, cells were washed and resuspended in complete media. Cells contained in 1 ml culture were harvested at various times. Total RNA was prepared and then analyzed by 15% polyacrylamide gel containing 7M urea. The amount of ribozyme radioactivity was normalized to actin mRNA or ribosomal RNA and then expressed as a percentage of the radioactivity present after 16 hours post-transfection time. These experiments were repeated 50 times for certain time points. FIG. 3C depicts a single experiment. Reexamination of FIG. 3C shows parallel curves for ribozyme A and B indicating similar stability for ribozyme B.

Figure 5A:
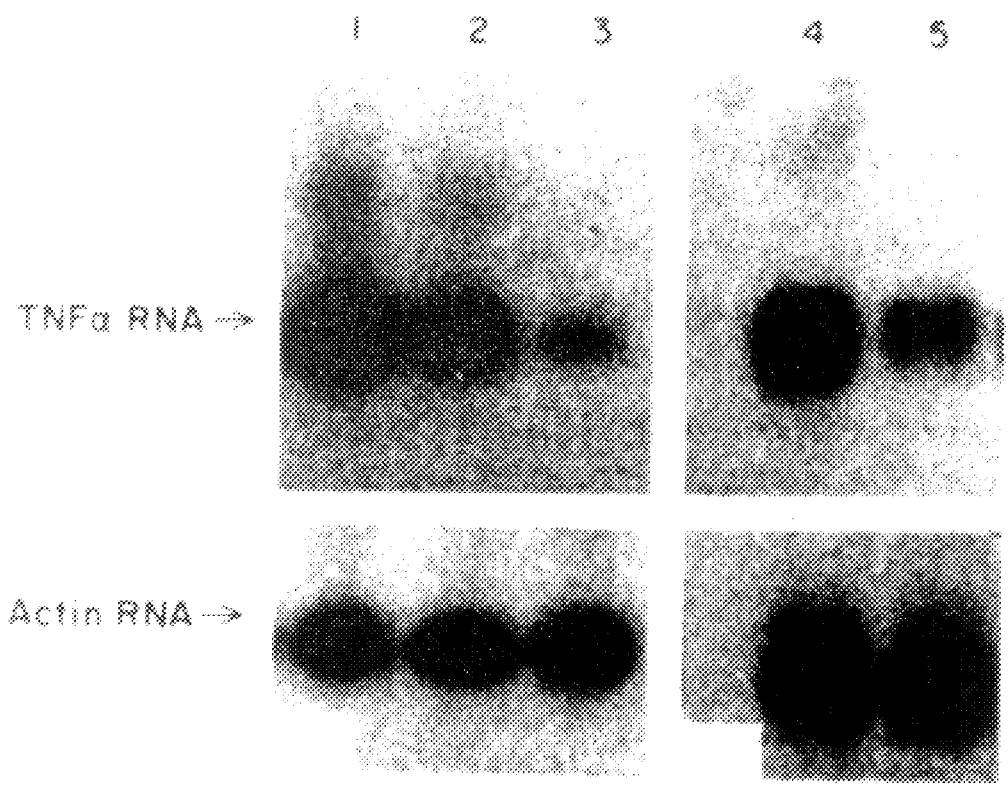
Figure 5B:
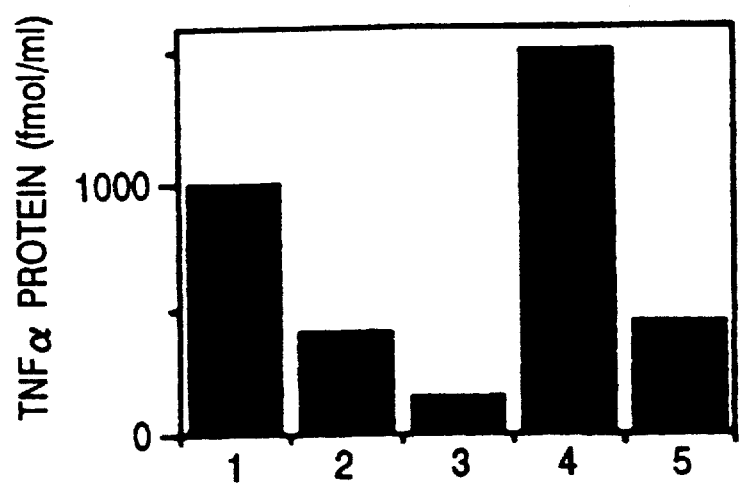

FIG. 5A–5B. Ribozyme activity in vivo.

FIG. 5A shows ribozymes and antisense RNA activities in HL60 cells were analyzed after a transfection period (20 h). Following transfection with ribozyme A or antisense RNA, cells were stimulated for 6 h to express TNF-α. RNA was extracted, separated by gel electrophoresis through a 1–2% (w/v) agarose formaldehyde gel, and detected by Northern blotting with a radioactive probe for the TNF-α gene. After hybridization with TNF-α probe, the filter was stripped and then rehybridized with an actin probe (British Biotechnology Limited), in the case of peripheral blood mononuclear cells PBMNC. Cells were separated (Sioud et al., 1990) and washed 4 times with Hank's buffered saline solution and 3 times with serum-free medium. Cells ($10^6$) were transfected and processed as HL60 cells. Lanes 1 and 4, controls (transfected only with carrier RNA 1 μg E. Coli tRNA); lane 2, antisense RNA; lanes 3 and 5, ribozyme A. This autoradiogram was overexposed to display the TNF-α signal in ribozyme A lanes. FIG. 5(B) Radioimmunoassay to TNF-α protein. Ionomycin was used during stimulation to release the TNF-α protein into the medium. The amount of TNF-α protein present in the media was determined using the TNF-α [($^{125}$I)] assay system (Amersham). Lanes 1 to 5 correspond to lanes 1 to 5 in FIG. 5A and 5B, respectively.

Figure 6A:
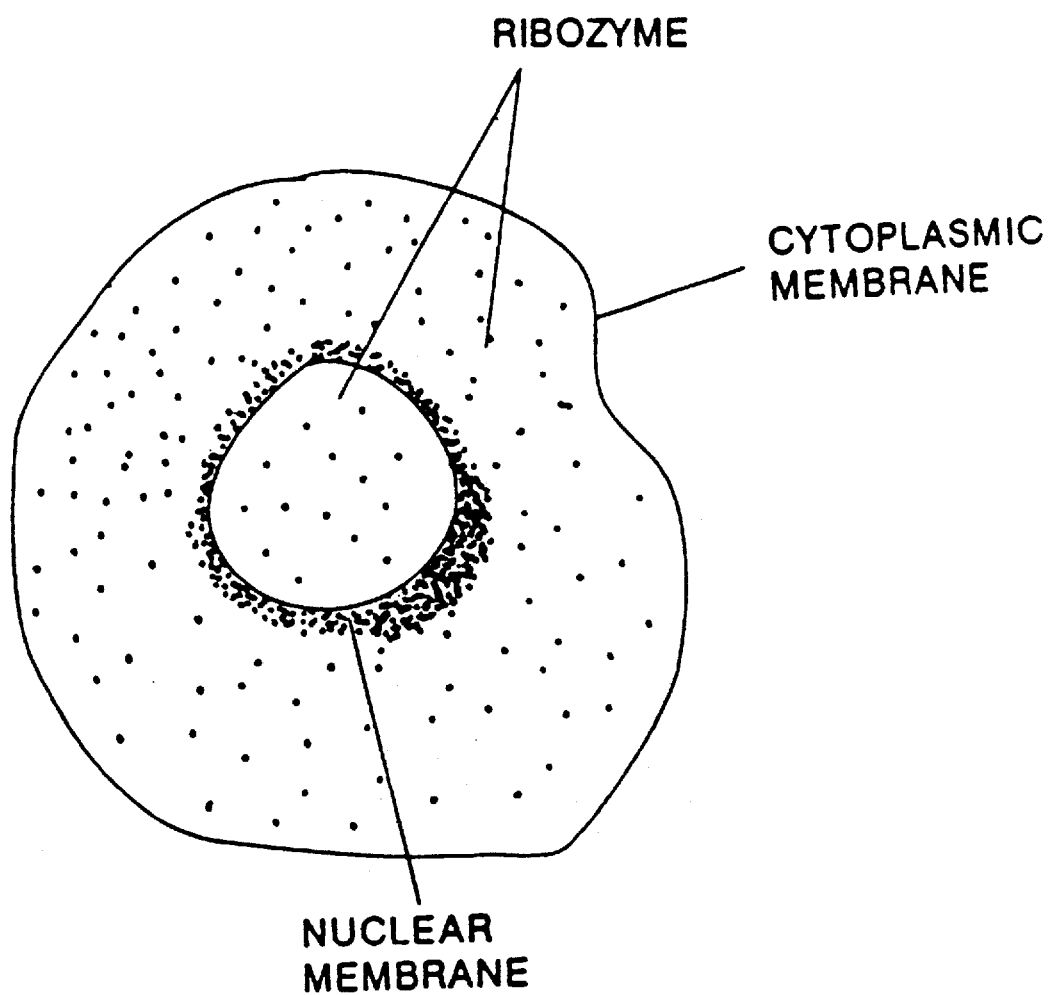
Figure 6B:
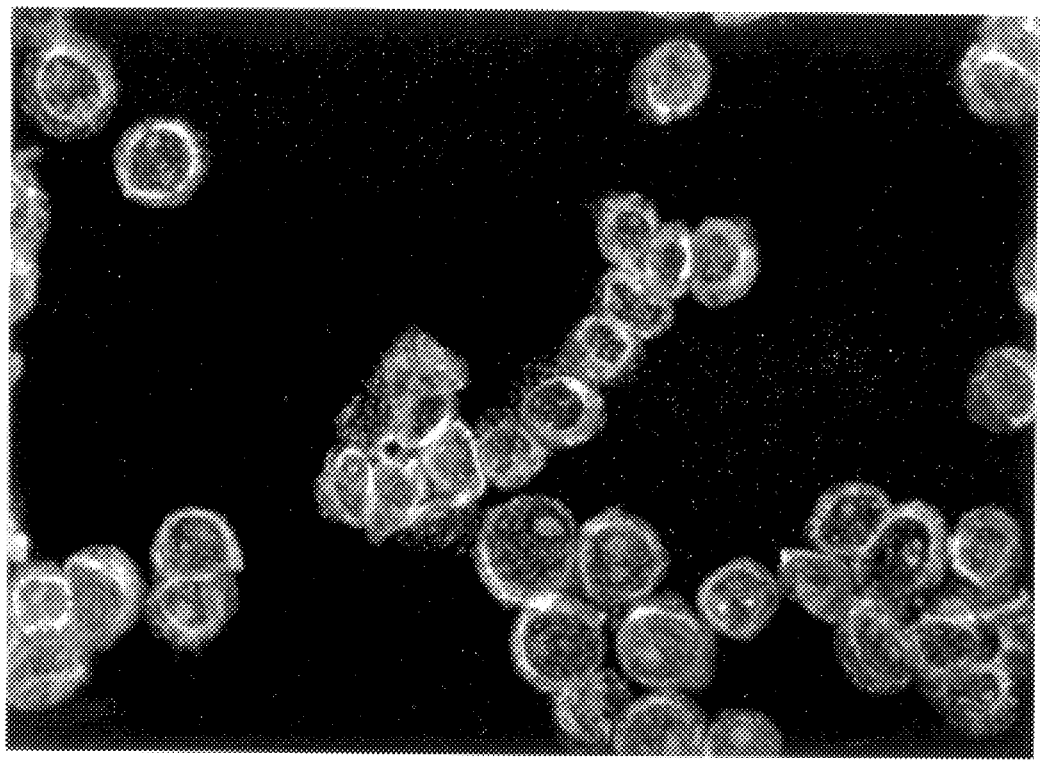

FIG. 6A–6B: Immunostaining of the ribozyme B and II in HL60 cells.

Digoxigenin conjugated uridine was incorporated into the ribozymes during transcription. Cells were transfected with digoxigenin-conjugated ribozymes. Following transfection microscope slides were prepared and the ribozyme inside the cells was detected with anti-digoxigen-fluorescein Fab conjugate. FIG. 6A is a schematic drawing. A micrograph of the fluorescent cells is shown in FIG. 6B.

Figure 7B:
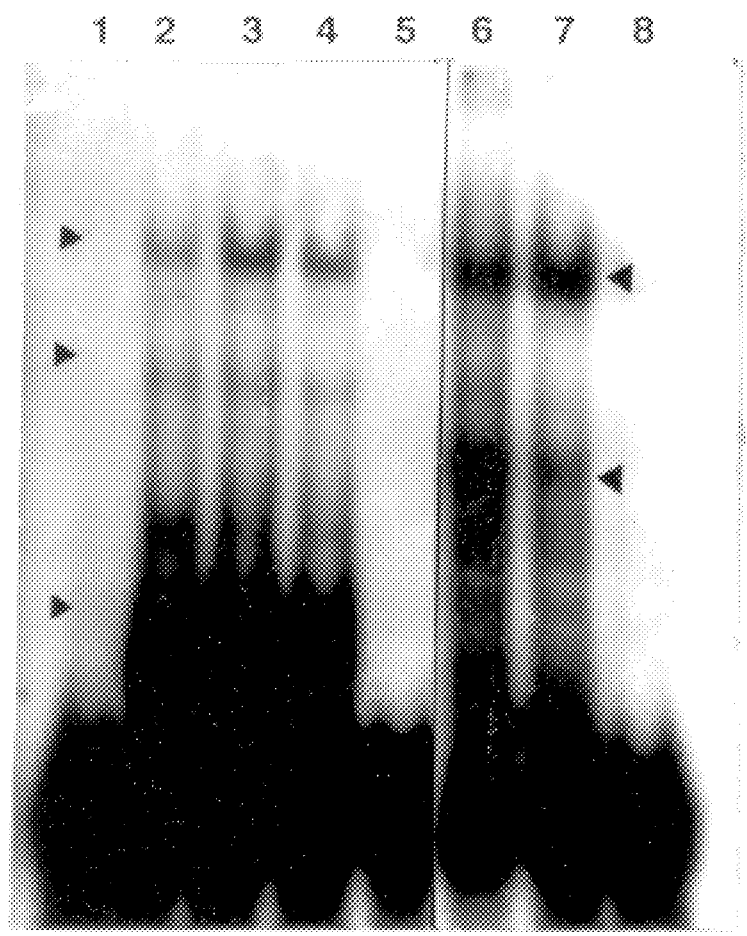
Figure 7C:
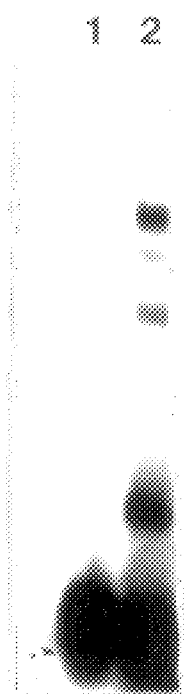

FIG. 7A–7C: Gel retardation assay of cytoplasmic extracts from HL60 cells and PBMNC with TNF-α ribozymes II and B.

FIG. 7(A) Ribozyme II was incubated at RT for 25–30 min (lanes 2, 3, 4 and 5) (see below) or not (lane 1) with extract proteins and then analyzed by electrophoresis (25 μg oligo +5 μg cytoplasmic extract (CE)). Lanes 4 and 5 are as lanes 2 and 3 respectively, but with 20 units of RNAsin added. All complexes seen in lanes 4 and 5 could be seen in lanes 2 and 3 (original film). FIG. 7(B) 25 ng of TNF-α ribozyme II was generated by in vitro transcription as described previously (Sioud, et al., 1992) and incubated at room temperature for 25 minutes with cytoplasmic extracts (CE) prepared from HL60 or PBMN cells. Following incubation, the protein ribozyme complexes were separated by 4% polyacrylamide native gel electrophoresis. Lane 1: control without CE; lane 2: +5 ug CE from HL60 cells; lane 3: as lane 2, but with the addition of 1ug of tRNA; lane 4 as lane 3, but with the addition of 10 units of Rnase inhibitor; lane 5 as lane 4, but before electrophoresis the sample was treated with proteinase k; lane 6 as lane 1, but 5 ug of the CE from PBMN cells was added; lane 7 as lane 6, but an additional 1 ug of tRNA was added; lane 8 contains the ribozyme RNA recovered from the high molecular weight complex. The complex was excised from one preparative gel, the materials were eluted and then phenol extracted. FIG. 7(C) Gel retardation with ribozyme B. As in panel A, ribozyme B was incubated (lane 2) with 5 ug of CE prepared from HL60 cells.

Figure 8:
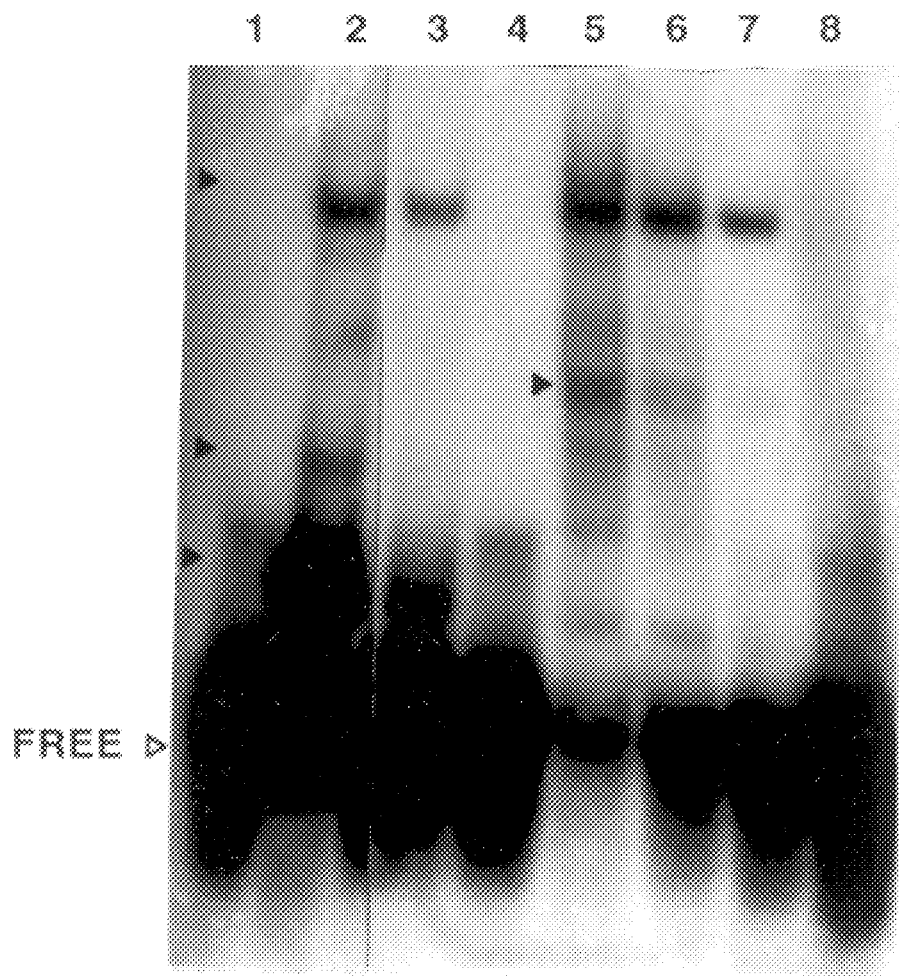

FIG. 8: Competition assays 25 ng of ribozyme II was incubated with 5 ug of cytoplasmic protein from HL60 cells or PBMN as described in FIG. 5. Lane 1 control without CE, lane 2 as lane 1, but both 5 ug of CE from HL60 cells and 2500 ng of poly-dCdI were added; lane 3 as lane 2, but instead of poly-dCdI, 2500 ng of cold ribozyme was added; lane 4 as lane 3, but 500-fold excess of cold ribozyme was added; lane 5 as lane 1, but 5 μg of CE from PEMN cells was added; lanes 6, 7, 8 as lane 5, but 300, 400 or 500 ng of cold ribozyme was added, respectively.

Figure 9A:
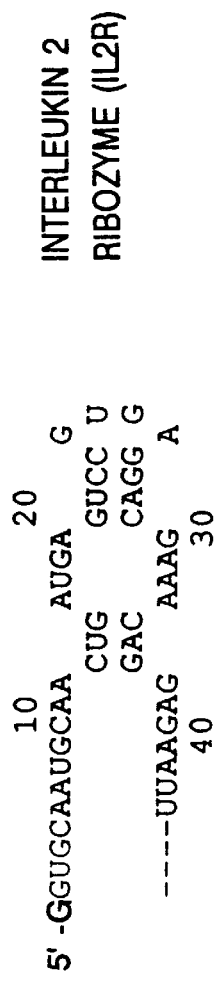
Figure 9B:
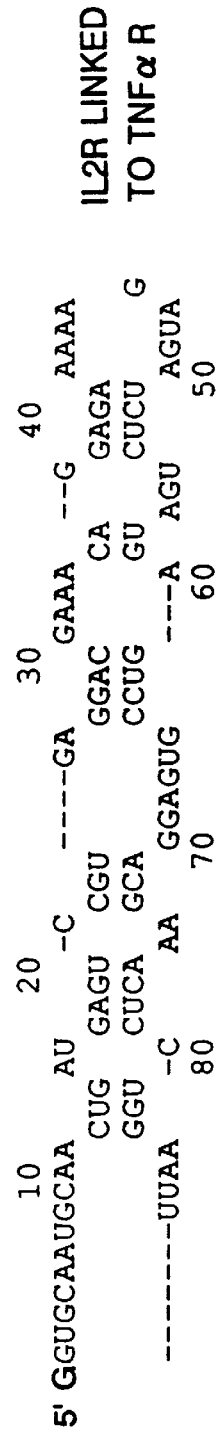
Figure 9C:
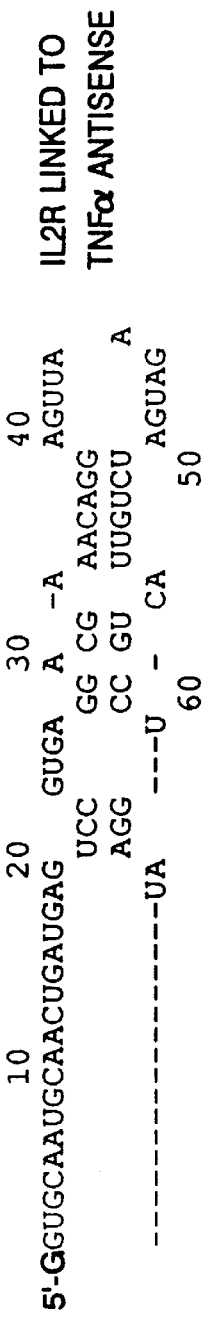

FIGS. 9A–9C: Predicted secondary structure of interleukin-2 (IL-2) ribozyme and IL-2 ribozyme linked to the 5'end of TNF-α ribozyme or antisense (SEQ ID NO:23–25), respectively.

Figures 10A, 10B:
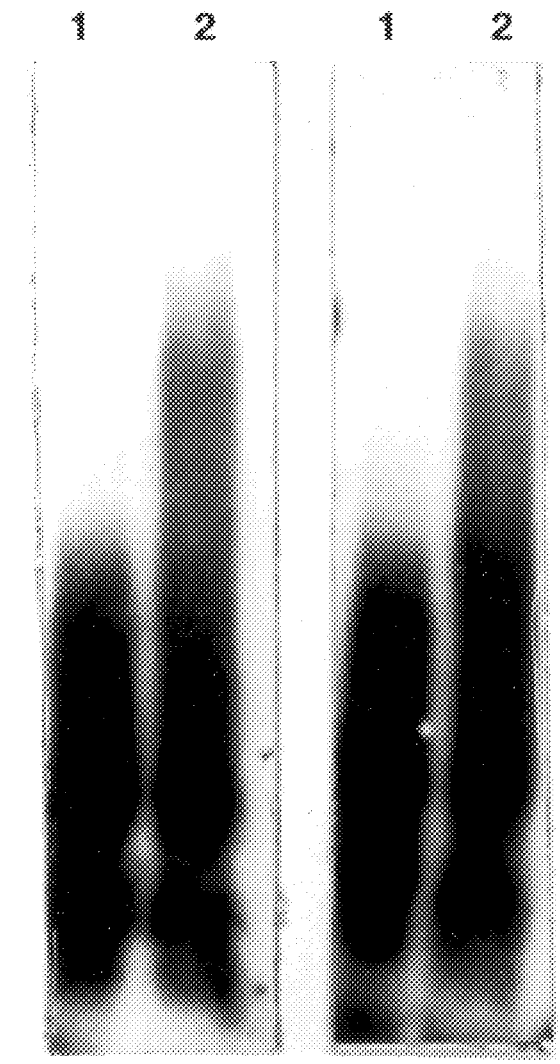

FIG. 10A–10B: Gel retardation assay of cytoplasmic extract with IL-2 ribozymes.

FIG. 10(A) 25 ng of IL-2 ribozyme generated by in vitro transcription was incubated with CE from HL60 cells. Lane 1, control without CE; lane 2, with CE from HL60 cells. FIG. 10(B) IL-2 ribozyme was incubated with CE from PBNM cells (lane 2).

Figure 11A:
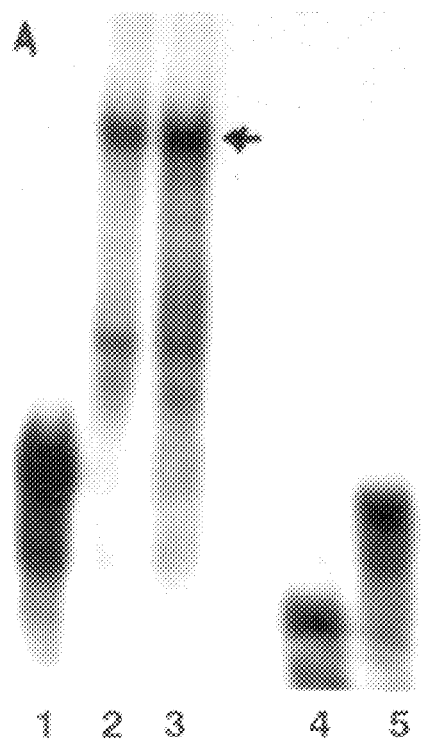
Figure 11B:
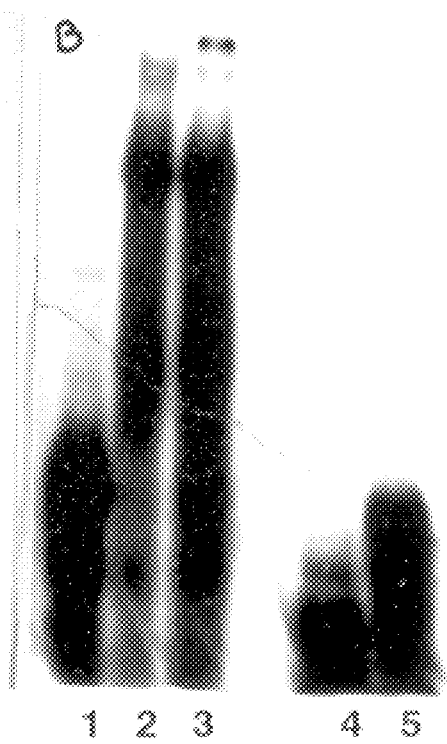
Figure 11C:
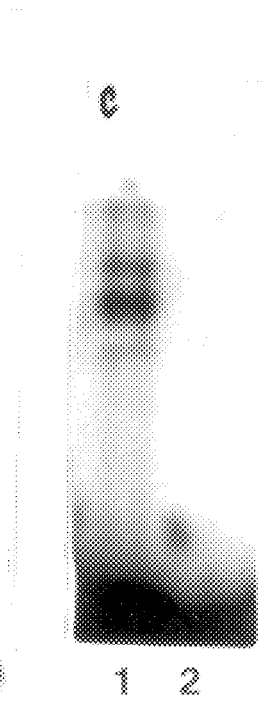

FIG. 11A–11C: Gel retardation and UV crosslinking experiments.

FIG. 11(A) 50 ng of TNF-60 ribozyme II generated by in vitro transcription was incubated at room temperature for 25 minutes with cytoplasmic extracts (CE) prepared from PBMN cells. Following incubation the protein-ribozyme complexes were separated by 6% polyacrylamide native gel electrophoresis. Lane 1, control without CE; lane 2, +5 μg CE1 from PBMN cells; lane 3, +5 μg CE2 from PBMN cells. Lanes 4 and 5, as lanes 2 and 3 respectively, but treated with proteinase-K for 15 min prior to electrophoresis. CE1 and CE2 correspond to two different cytoplasmic protein preparations. FIG. 11(B) The same panel as A, but overexposed. FIG. 11(C) The region of the gel containing the complex as indicated by arrow was cut from the native gel, exposed to UV light for 30 min, soaked in Tris buffer, treated with ribonuclease T1 and analyzed on a 10% SDS polyacrylamide gel.

FIG. 12A: Gel retardation with IL-2 ribozyme, IL-2 linked ribozyme linked to the 5' of TNF-α ribozyme.

50 ng of TNF-α ribozyme, IL-2 ribozyme, IL-2 linked ribozyme to the 5' of TNF-α ribozyme or IL-2 linked to the 5' TNF-α antisense were incubated at room temperature with two different cytoplasmic extracts (CE1 and CE2) prepared from PBMN cells. Lane 1, TNF-α ribozyme–CE as control; lane 2, TNF-α ribozyme+CE; lane 3, IL-2 ribozyme–CE as control; lane 4, IL-2 ribozyme+CE; lane 5, IL-2 ribozyme+CE2; lane 6, IL-2 ribozyme linked to the 5' end of the TNF-α ribozyme–CE; lane 7, IL-2 ribozyme linked to the 5' end of the TNF-α ribozyme+CE1; lane 8, IL-2 ribozyme linked to the 5' end of the TNF-α ribozyme+CE2.

FIG. 12B: Gel retardation with IL-2 linked to the 5' TNF-α antisense.

Lane 1, IL-2 ribozyme linked to the TNF-α antisense–CE; lanes 2 and 3, IL-2 ribozyme linked to the TNF antisense+2 μg CE1 or 5 μg CE respectively.

FIG. 13A–13B: Secondary Structures

FIG. 13(A) Predicted secondary structure of T7 terminator linked to TNF-α ribozyme. FIG. 12(B) TNFα antisense linked to the 3' end of the TNF-α ribozyme (SEQ ID NO 26–27). In order to obtain the folding for the antisense molecule two As were added at the junction.

FIG. 14A: Gel retardation using TNF-α ribozyme or TNF antisense linked to TNF-α ribozyme.

50 ng of TNF-α ribozyme II or TNF antisense linked to TNF ribozyme generated by in vitro transcription were incubated at room temperature for 25 min with cytoplasmic extracts (CE) prepared from PBMN cells. Lane 1, TNF-α–CE as control; lane 2, TNF-α+CE; lane 4, TNF antisense linked to TNF-α ribozyme–CE as control; lane 5 and 6, as lane 4, but incubated with CE1 and CE2 respectively.

FIG. 14B: Competition experiments.

Lane 1, control–CE; lane 2, +CE; lane 3, as lane 2, but 300 excess of cold TNF-60 ribozyme was added to the reaction; lane 4, as lane w, but 500 ng of cold TNF-α ribozyme was added to the reaction.

FIG. 15A–15B: FIG. 15A) Predicted secondary structure of the IL-2 ribozyme and FIG. 15B) IL-2 ribozyme linked to the 3' end of the TNF-α ribozyme (SEQ ID NO 28–29).

Figure 16:
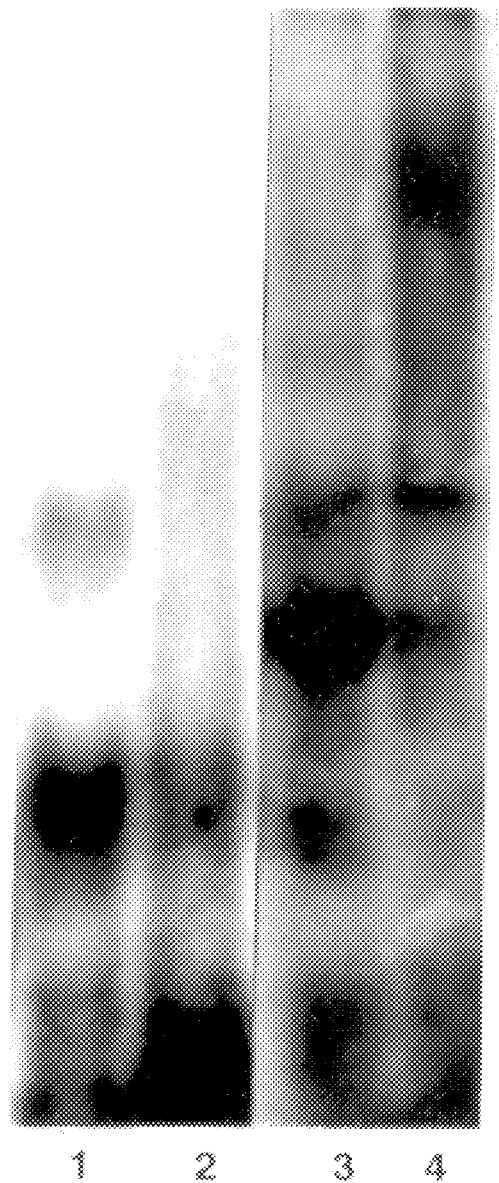

FIG. 16: Gel retardation using IL-2 ribozyme or IL-2 ribozyme linked to the 3' of TNF-α ribozyme.

50 ng of IL-2 ribozyme and IL-2 ribozyme linked to the 3' of TNF-α ribozyme generated by in vitro transcription were incubated with or without cytoplasmic extract for 25 min at room temperature. Lane 1, IL-2 ribozyme–CE as control; lane 2, as lane 1, but+CE; lane 3, IL-2 Ribozyme linked to the 3' end of TNF-α ribozyme–CE as control; lane 4, as lane 3 but+CE. The electrophoresis mobility of the IL-2 ribozyme and IL-2 linked to TNF-α was not reproducible, presumably due to intramolecular interactions.

FIG. 17A–17B: FIG. 17A) Predicted secondary structure of the TNF-α ribozyme truncated at the 5' end and FIG. 17B) the TNF-α ribozyme truncated at the 3' end (SEQ ID NO 30–31).

FIG. 18A–18D: Gel retardation assay using TNF-α ribozyme, the 3' or 5' truncated TNF-α ribozyme and the integrase ribozyme.

Figures 18A, 18B:
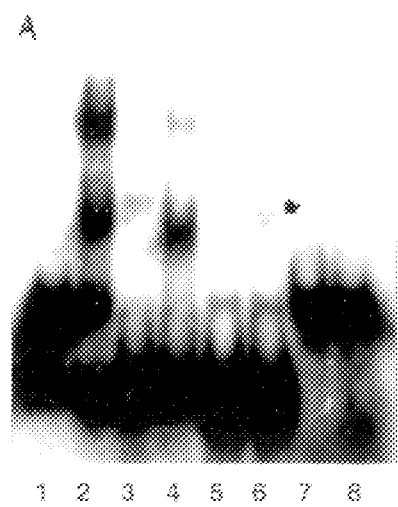
Figure 18C:
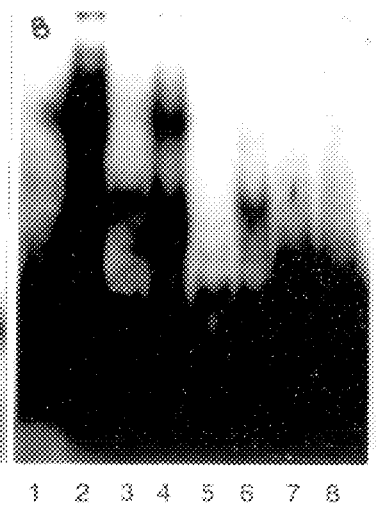
Figure 18D:
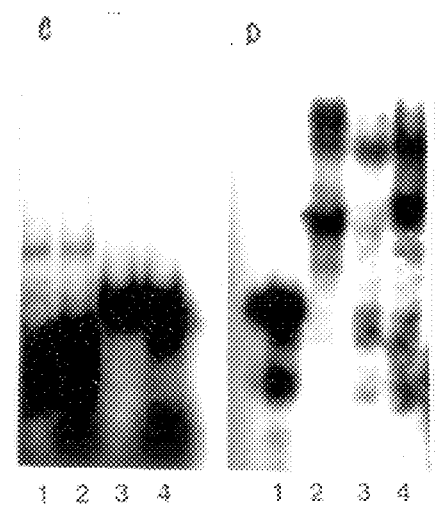

FIG. 18(A) 50 ng of TNF-α ribozyme, the 3' or 5' truncated TNF-α ribozyme and the integrase ribozyme generated by in vitro transcription were incubated at room temperature for 25 min with cytoplasmic extracts (CE) prepared from PEMN cells. Lane 1, TNF-α ribozyme–CE; lane 2, TNF-α ribozyme+CE; lane 3, a 3' truncated TNF-α ribozyme–CE as control; lane 4, as lane 3 but+CE; lane 5, a 5' truncated TNF-α ribozyme–CE as control; lane 6, as lane 5, but+CE; lane 7, integrase ribozyme–CE as control; lane 8, as lane 7, but+CE. FIG. 18(B) As panel A, but overexposed. FIG. 18(C) Lane 1, the 5' truncated TNF-α ribozyme–CE as control; lane 2, as lane 1, but+CE; lane 3, integrase ribozyme–CE as control; lane 4, as lane 3, but+CE. FIG. 18(D) 25 ng of the 3' truncated TNF-α ribozyme generated by in vitro transcription was incubated at room temperature for 25 min with cytoplasmic extracts prepared from different cell types. Lane 1,–CE as control; lane 2, as lane 1, but incubated with CE prepared from PBMN cells; lane 3, as lane 1, but incubated with CE prepared from HL60 cells; lane 4, as lane 1 but+CE prepared from WH164 cells.

Figure 19A:
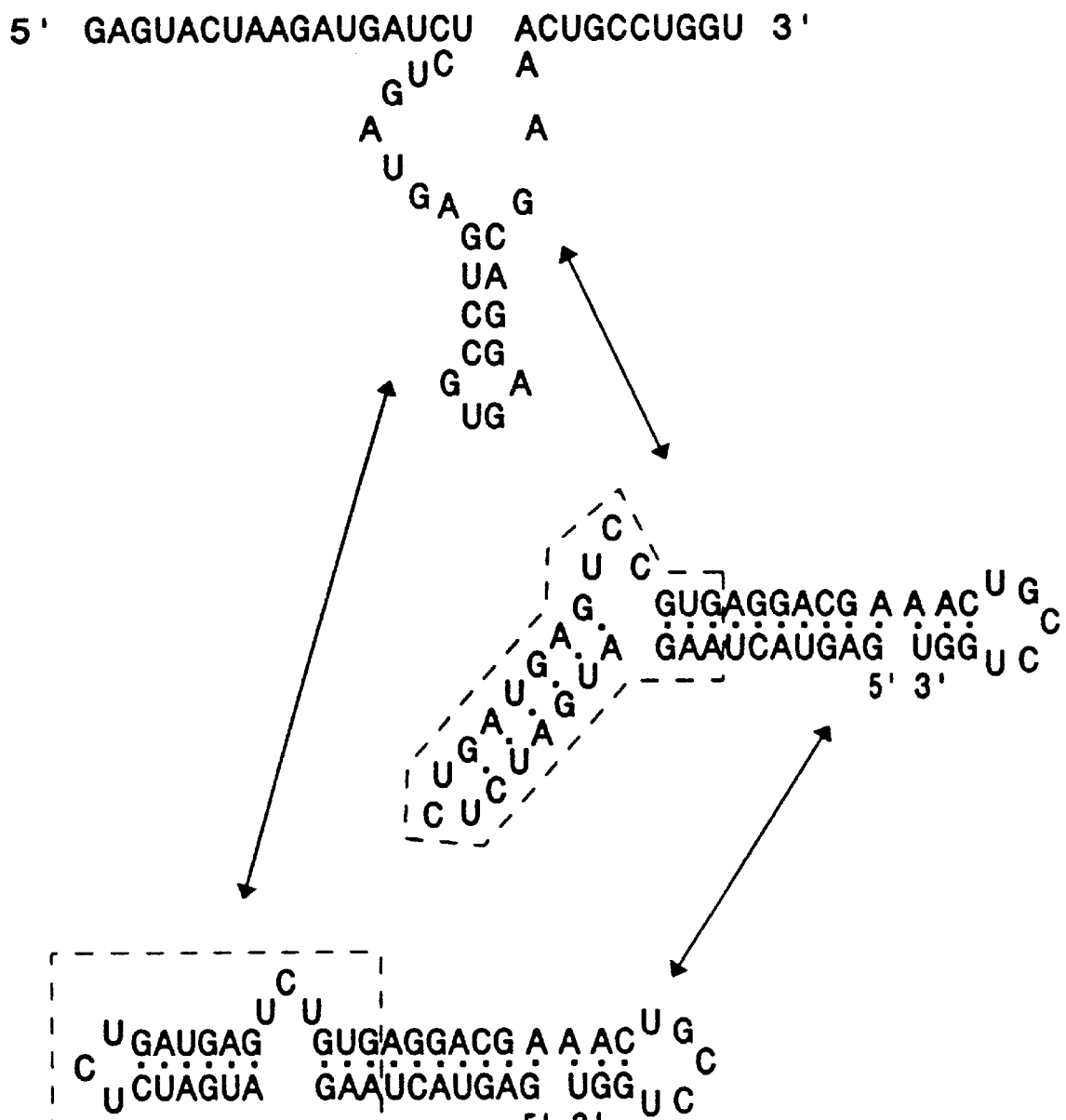
Figure 19B:
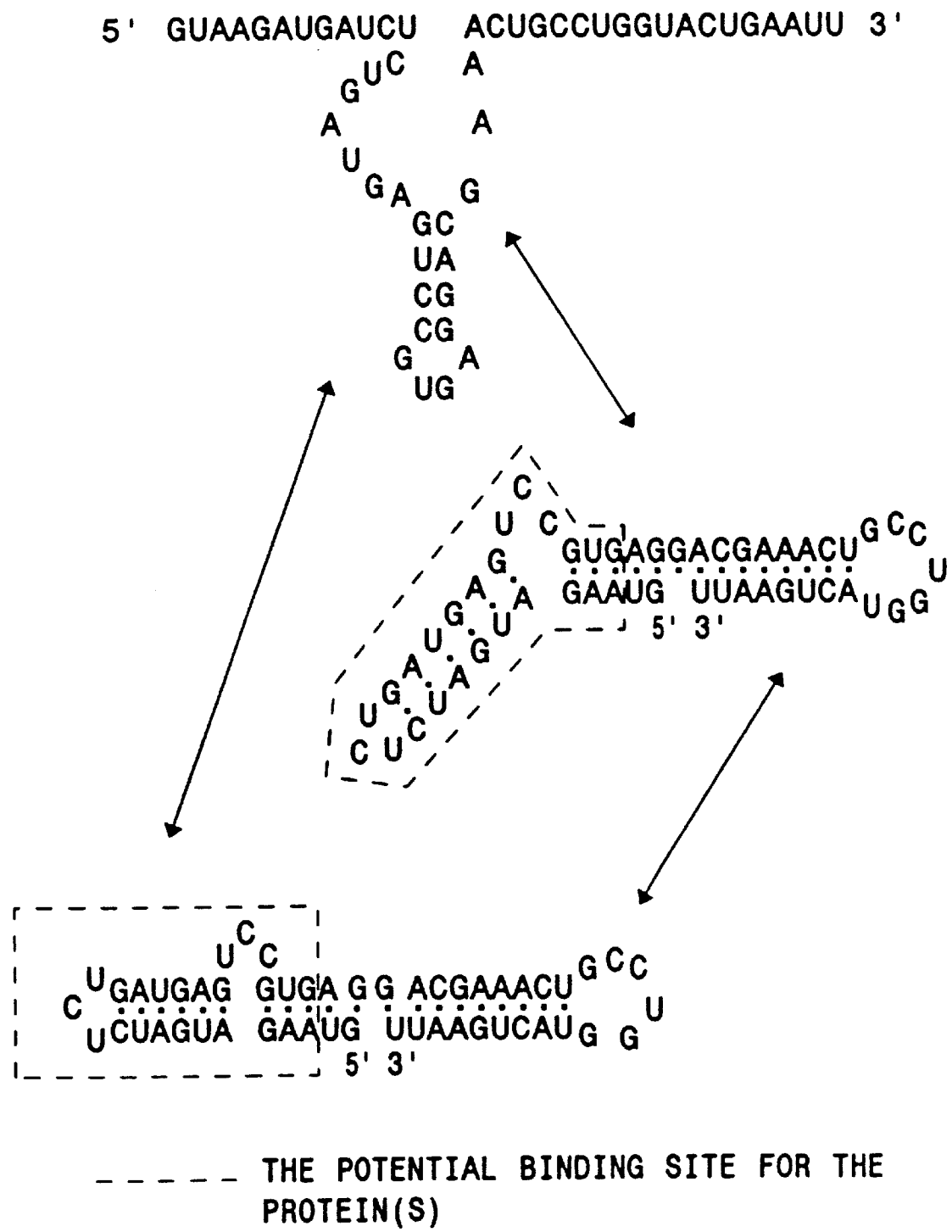

FIGS. 19A–19B: Potential binding sites for protein on TNF-α ribozyme B is shown in FIG. 19A and TNF-α ribozyme II is shown in FIG. 19B.

Figure 20:
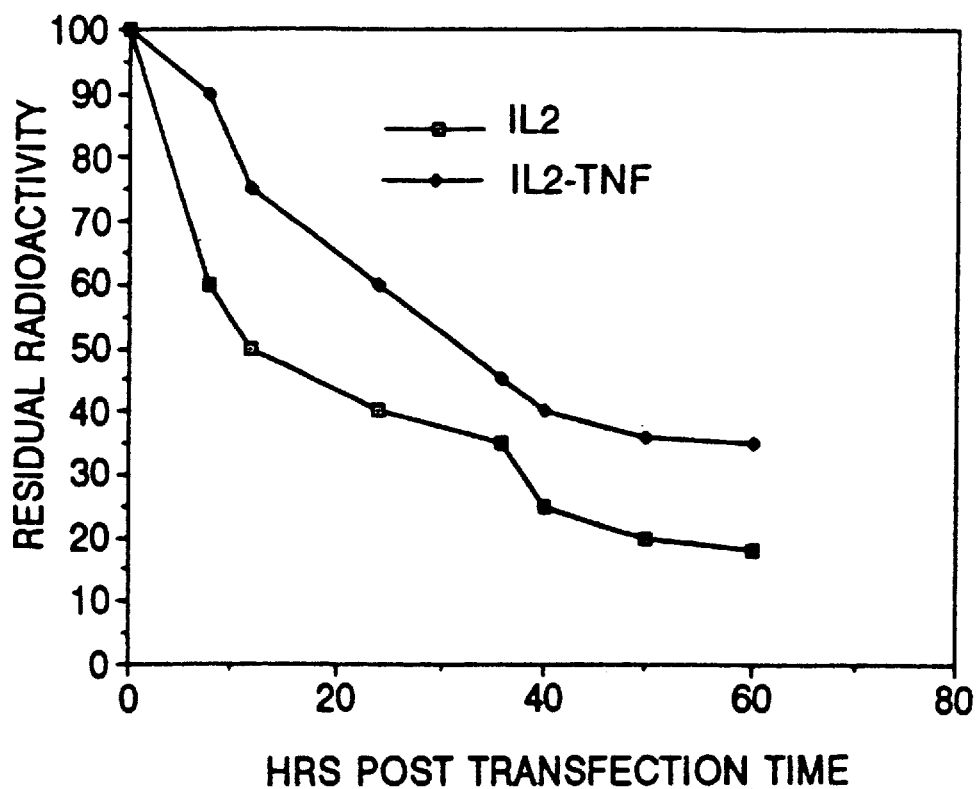

FIG. 20: In vivo activity of IL-2 ribozyme and IL-2 ribozyme linked to the 3' end of the TNF-α ribozyme.

Figure 21A:
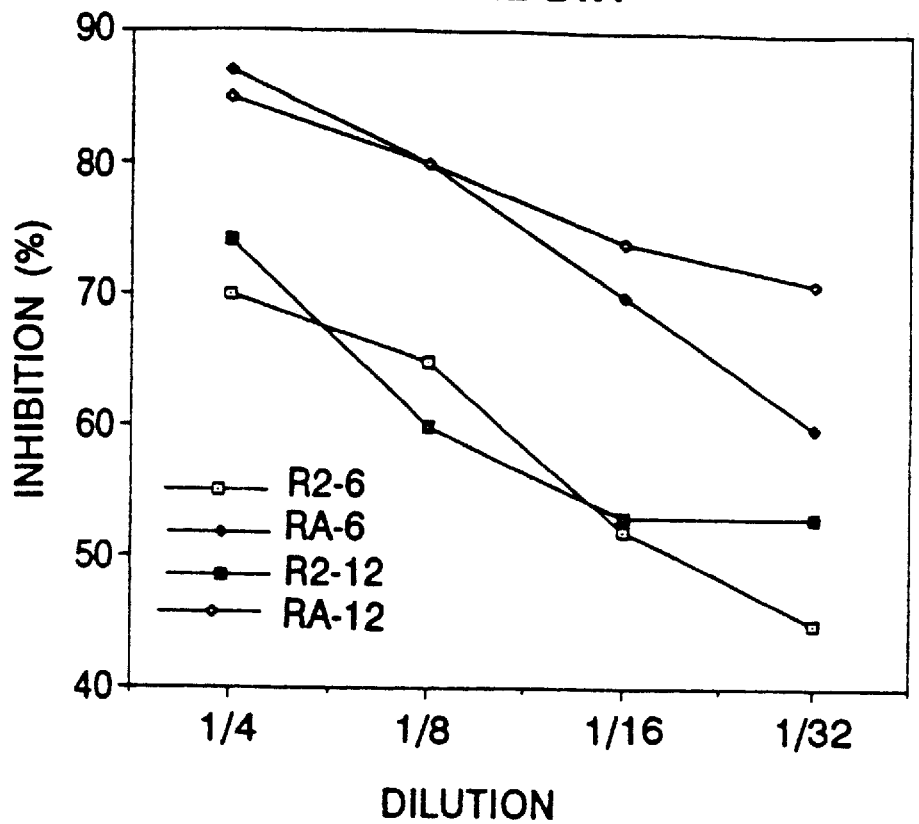
Figure 21B:
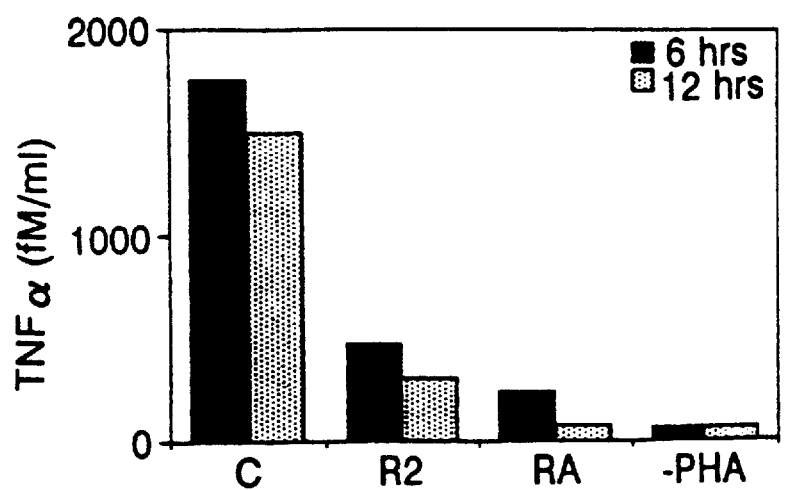

FIG. 21A–21B: In vivo activity of the TNF-α ribozyme and the TNF-α antisense linked to the 3' end of the TNF-α ribozyme.

FIG. 21(A) Cytotoxicity assay at 6 and 12 hrs transfection time. FIG. 21B(B) Quantification of the TNF-α levels by radioimmunoassay.

Figure 22:
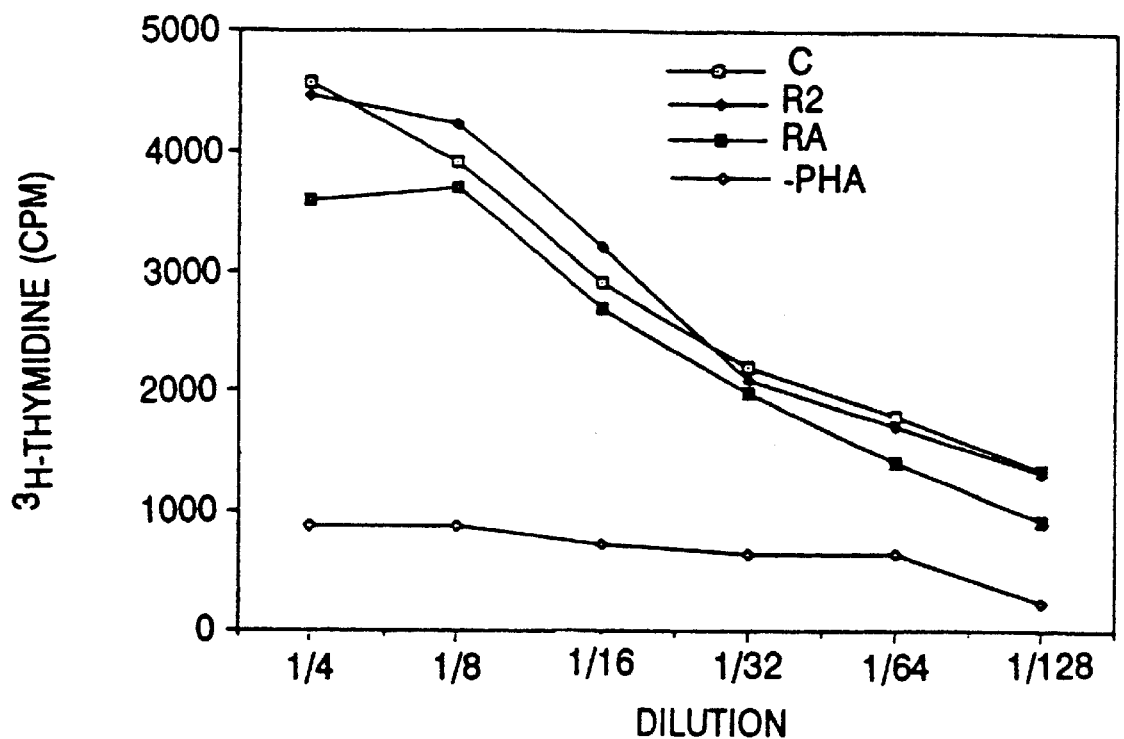

FIG. 22: Quantification of in vivo levels of IL-2 by CTLL2 assay (see text).

Figure 23:
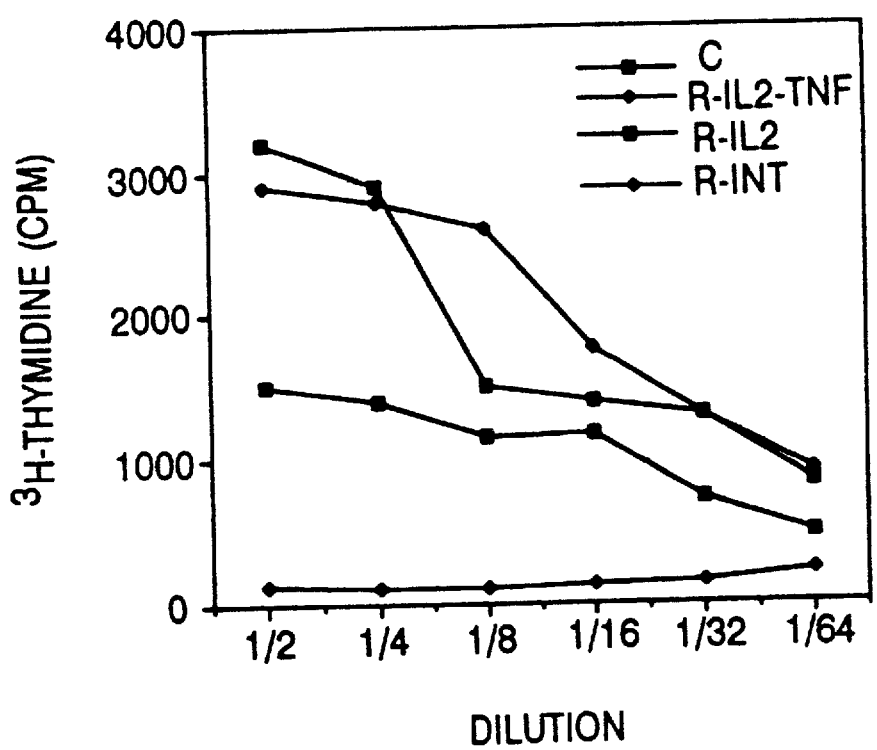

FIG. 23: Effect of TNF-α ribozyme and antisense on IL-2 gene expression.

Figure 24A:
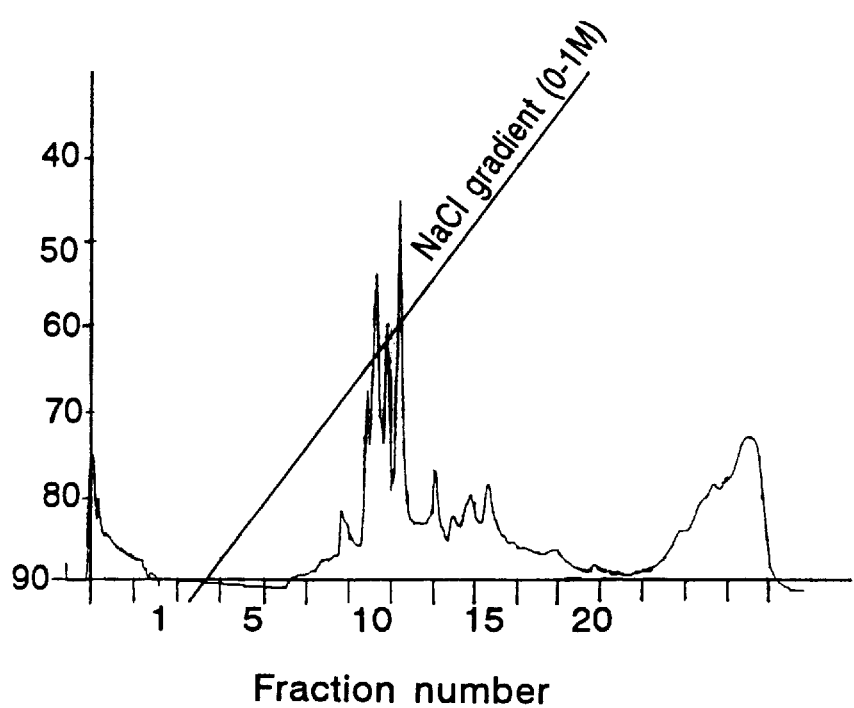
Figure 24B:
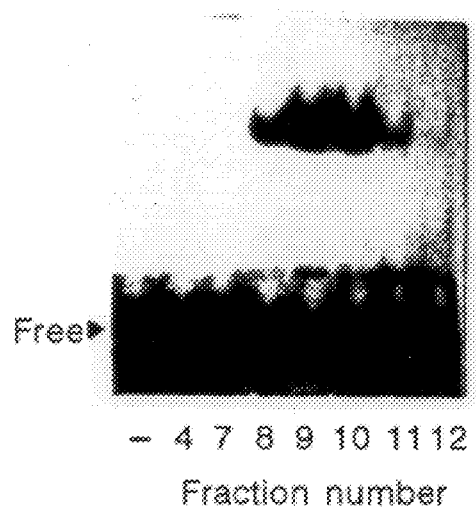
Figure 24C:
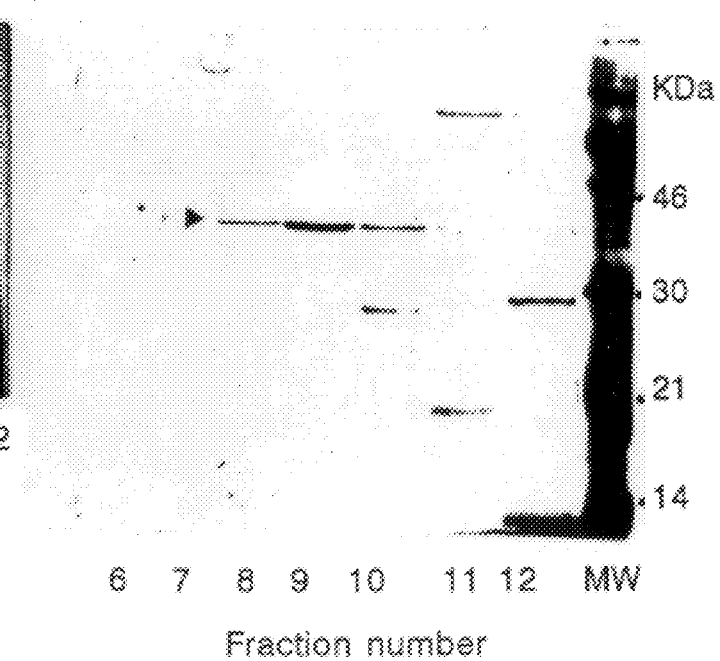

FIG. 24A, 24B and 24C: Identification of the ribozyme binding protein in PBMN cells.

FIG. 24(A) Protein profile. Cytoplasmic crude extract from PBMN cells (5 mg) was fractionated by Mono Q column with a linear salt gradient ranging from 0 to 1M. FIG. 24(B) Gel retardation assay. Proteins contained in 10 μl of dialyzed fractions were tested for the binding to TNF-α-Rz and FIG. 24(C) analyzed by 10% SDS polyacrylamide gel and silver stained. No detectable TNF-α-Rz binding activity was found in the other fractions.

FIG. 25A–25B: Localization of GAPDH in PBMN cells by indirect immuno-fluorescence.

FIG. 25(A) Cells incubated with rabbit preimmune serum and FIG. 25(B) cells incubated with the immune rabbit serum raised against the 37 kDa pure protein.

FIG. 26A, 26B and 26C: Binding of the 37 kDa protein and commercial GAPDH to hammerhead ribozymes.

FIG. 26(A) and FIG. 26(B) represent the binding activity of the purified 37 kDa protein to ribozymes. The test molecules, as indicated on the bottom of each lane were incubated with (+) or without (–) 0.1 μg of the purified protein. Following incubation the samples were analyzed by gel retardation assay. FIG. 26(C) Binding activity of commercial GAPDH (Sigma). 0.1 μg of GAPDH was incubated with the test molecules as indicated in the bottom of each line and then analyzed as in panel A.

FIG. 27A–27B: Competition assays.

FIG. 27(A) 0.2 μg of the 37 kDa purified protein was incubated with (+) 5 ng of internally [$^{32}$P]-labelled TNFα ribozyme in the presence of cold TNFα-Rz (lanes 3–6) or E. coli tRNA (lanes 7–10), and then analyzed by gel retardation. Lanes 3, 4, 5 and 6 are the same as lane 2, but contain 10, 25, 50 and 100 fold excess of cold TNFα-Rz. Lanes 7, 8, 9 and 10 are the same as lane 2, but contain 40, 80, 160 and 240 fold excess of cold E. coli tRNA, respectively. FIG. 27(B) 0.1 μg of commercial GAPDH (Sigma) was incubated (+) with 5 ng of internally [$^{32}$P]-labelled TNFα-Rz in the presence of cold TNFα-Rz (lanes 3–6) or IL2-Rz (lanes 7–10), and then analyzed as in panel A. Lanes 3, 4, 5 and 6 are the same as lane 2, but contain 10, 25, 50 and 100 fold excess of cold TNFα-Rz. Lanes 7, 8, 9 and 10 are as lane 2, but contain 10, 25, 50 and 100 fold excess of cold IL2-Rz, respectively.

Figure 28:
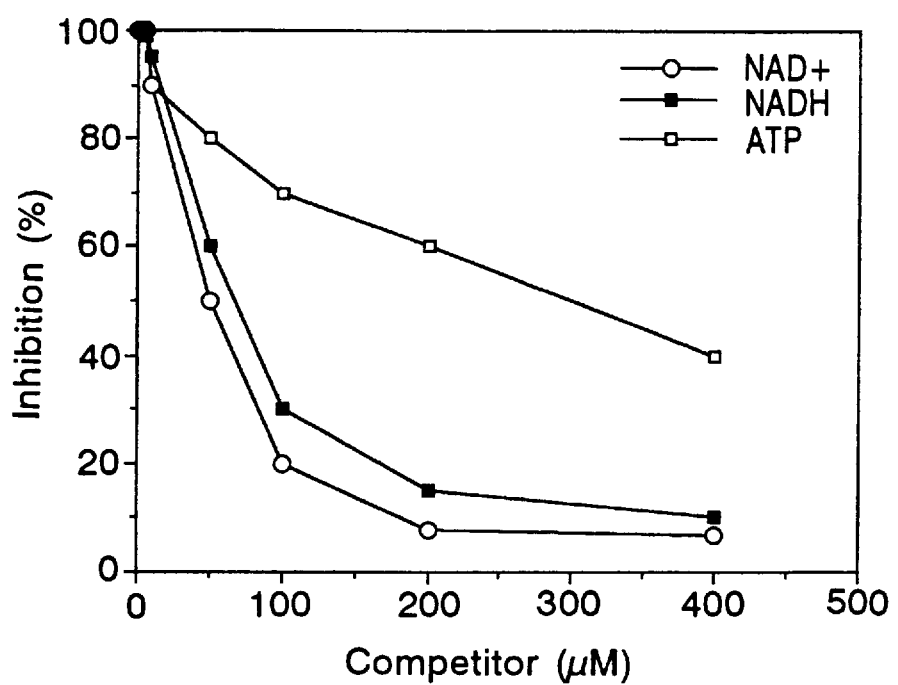

FIG. 28: Competition assay with NAD+, NADH and ATP

Commercial GAPDH (0.2 μg) was incubated with (+) 5 ng in 20 μl reaction solution of internally [$^{32}$P]-labelled TNFα-Rz in the presence of different concentration of NAD$^+$ and then analyzed by gel retardation. The radioactivity in each complex was quantified by Phospho-Imager (FUJIX BAS 1000), and expressed as a percent of total radioactivity present in the ribozyme-GAPDH complex without competitor.

FIG. 29A, 29B, 29C and 29D: In vitro cleavage activity of the TNF-α-Rz in the presence of purified protein.

Figure 29A:
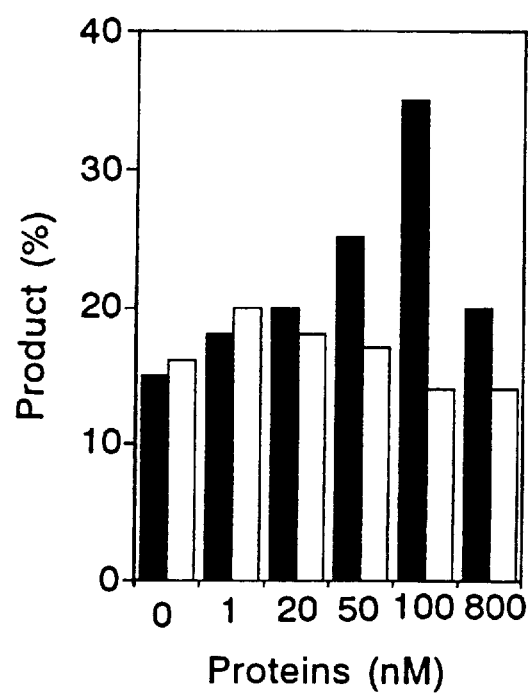

FIG. 29(A) Ribozymes (2 nM) and the [$\gamma^{32}$P]-labelled 20-mer target RNA (50 nM) were incubated at 37° C. in the presence or absence of different concentrations of purified protein (Filled rectangle) or lactate dehydrogenase (open rectangle) as unspecific protein in a reaction buffer containing 50 mM Tris-HCl pH 7.5 and 1 mM MgCl$_2$. Following incubation the substrate and the 5'end-labelled product were separated by electrophoresis on a 15% polyacrylamide-7M urea. The radioactivity contained in each 5' end was quantified by Phospho-Imager. (B and C) An example of autoradiogram of a denaturing PAGE gel (15%) used to separate products (P) from the substrate (S) following multiple turnover reactions of TNF-α-Rz in the absence FIG. 29(B) or the presence of 150 ng/ul GAPDH FIG. 29(C). Appropriate time (min) is indicated on the top of each lane. The radioactivity containing in each 5' end-labelled product was quantified and expressed as percentage of radioactivity present in the substrate FIG. 29(D).

Figure 30:
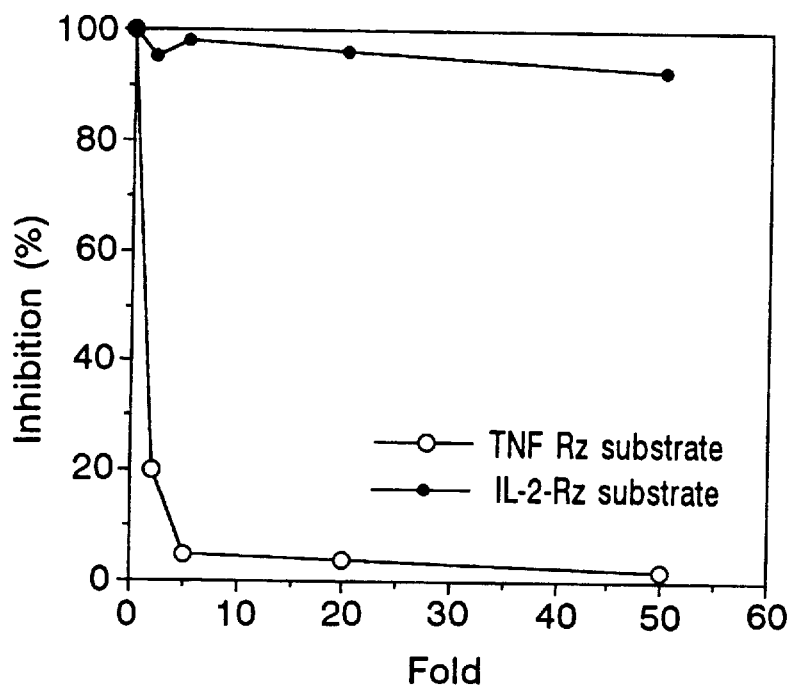

FIG. 30: Inhibition of the ribozyme to bind GAPDH by its substrate

In these experiments the [$^{32}$P]-labelled TNFα-Rz was incubated at 37° C. with different concentrations of TNF-α substrate or IL-2 substrate for 10 minutes prior to addition of GAPDH and further incubation for 25 minutes. Following incubation the protein ribozyme complexes and the free ribozyme were separated by gel retardation assay. The radioactivity in each complex was quantified by Phospho-Imager and expressed as percent of total radioactivity present in the ribozyme-GAPDH complex without competitor.

Figures 31A, 31B:
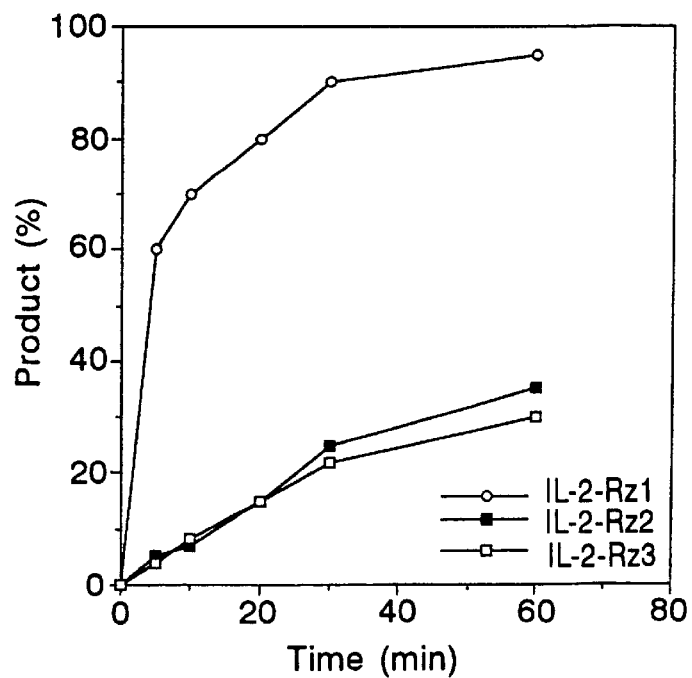

FIG. 31A and 31B: Cleavage rates of IL-2 ribozymes.

FIG. 31(A) Secondary structure of IL-2-Rz1 (SEQ ID NO: 35), IL-2-Rz2 (SEQ ID NO: 36) and IL-2-RZ3 (SEQ ID NO: 37). FIG. 31(B) Cleavage activity. 0.5 μM of IL-2-Rz1. IL-2-Rz2 or IL-2-Rz3 were mixed with 0.2 μM of labelled 15-mer substrate in a reaction mixtures containing 50 nM Tris-HCl pH 7.5 and 10 mM MgCl$_2$ at 37° C. At appropriate times, a 10 μl aliquot was removed from the reaction and added to 10 μl quenching solution containing 80% formamide, 20 mM ETDA, and dye. The samples were analysed by electrophoresis on denaturing PAGE gel (15%), and then the radioactivity containing in each cleavage product was quantified by Phospho-Imager.

FIG. 32A, 32B, 32C, 32D and 32E: GAPDH stimulates the cleavage rate of IL-2-Rz-2

Figure 32A:
Figure 32B:
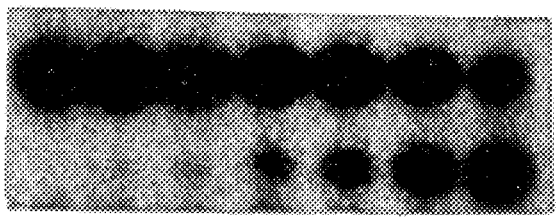
Figure 32C:
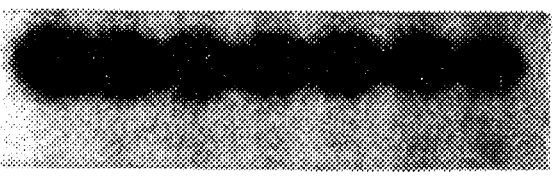
Figure 32D:
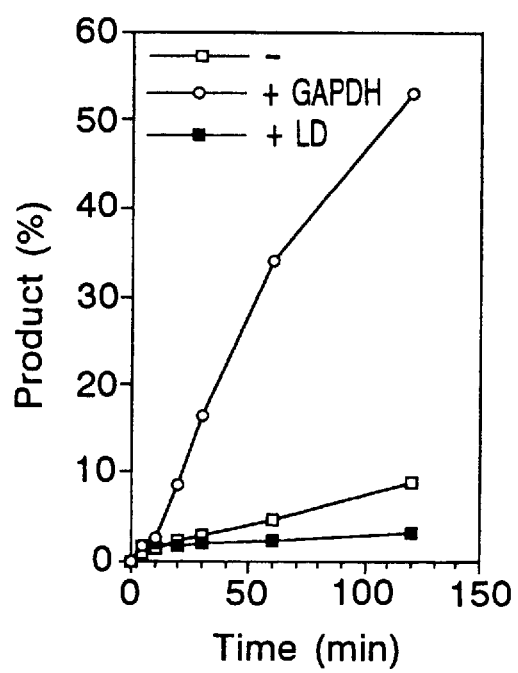
Figure 32E:
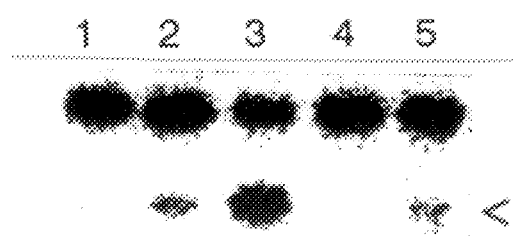

Autoradiogram of denaturing gels of multiple turnover reactions in the absence FIG. 32(A) or in the presence of GAPDH FIG. 32(B) as well as in the presence of LD as unspecific protein FIG. 32(C). 5 nM of the ribozyme and 50 nM of $^{65}$ATP-labelled 15-mer substrate were incubated in a reaction mixture containing 50 mM Tris-HCl pH 7.5 and 5 mM MgCl$_2$ at 37° C. in the absence or presence of proteins (150 ng/μl) and then processed as described below. FIG. 32(D) Quantification of the data shown in A, B and C by Phospho-Imager. Appropriate time (min) is indicated on the top of each lane. FIG. 32(E) Control experiments. A Phospho-Imager printout is shown following separation of the products by 15% PAGE gel. No cleavage activity was seen upon addition of GAPDH in absence of Mg$^{++}$ (lane 4). The cleavage rate of the ribozyme (lane 2) is enhanced by the addition of GAPDH (Lane 3). This cleavage enhancement is shut down by phenol treatment of the GAPDH preparation prior to addition (lane 5). Arrows indicated the cleavage products.

Figure 33A:
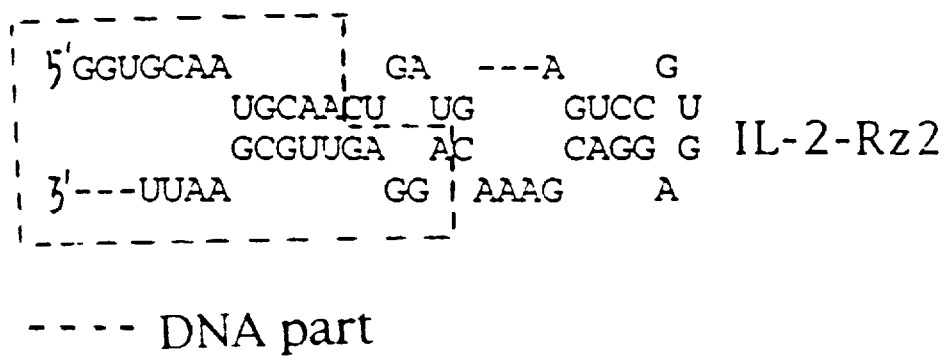
Figure 33B:
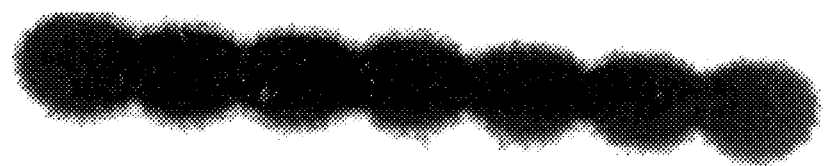
Figure 33C:

FIG. 33A, 33B and 33C: Effect of GAPDH on IL2-Rz2 DNA-armed ribozyme

FIG. 33(A) Secondary structure of the ribozyme illustrating the portion which is DNA. FIGS. 33(B and C) A Phospho-Imager printout is shown following separation of the products by 15% PAGE gels. 5 nM of IL-2-PB-Rz DNA armed ribozyme and 50 nM of $^\gamma$ATP-labelled 15-mer substrate were incubated in a reaction mixture containing 50 mM Tris-HCl pH 7.5 and 5 mM MgCl$_2$ at 37° C. in the absence FIG. 33(B) and the presence of GAPDH FIG. 33(C) at times (in min) which are indicated on the top of each lane.

Figure 34A:
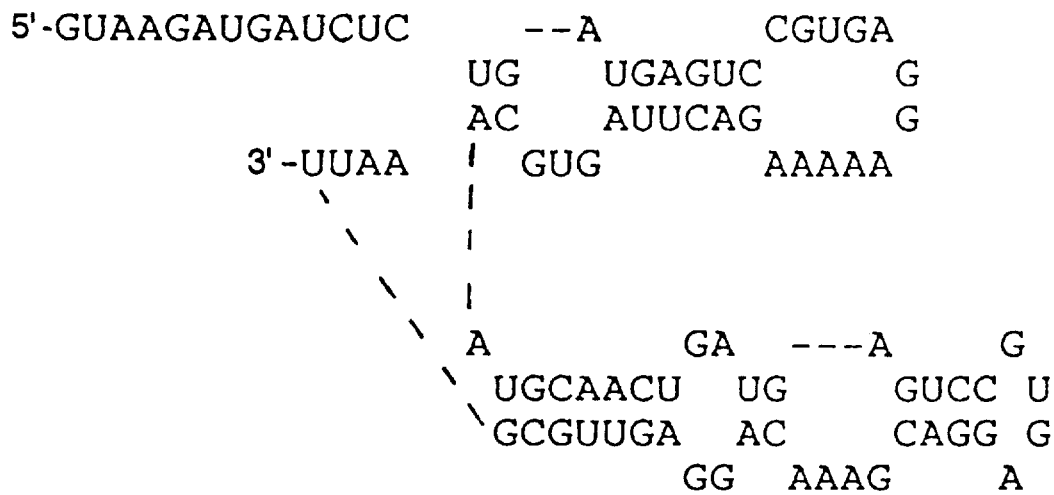
Figure 34B:
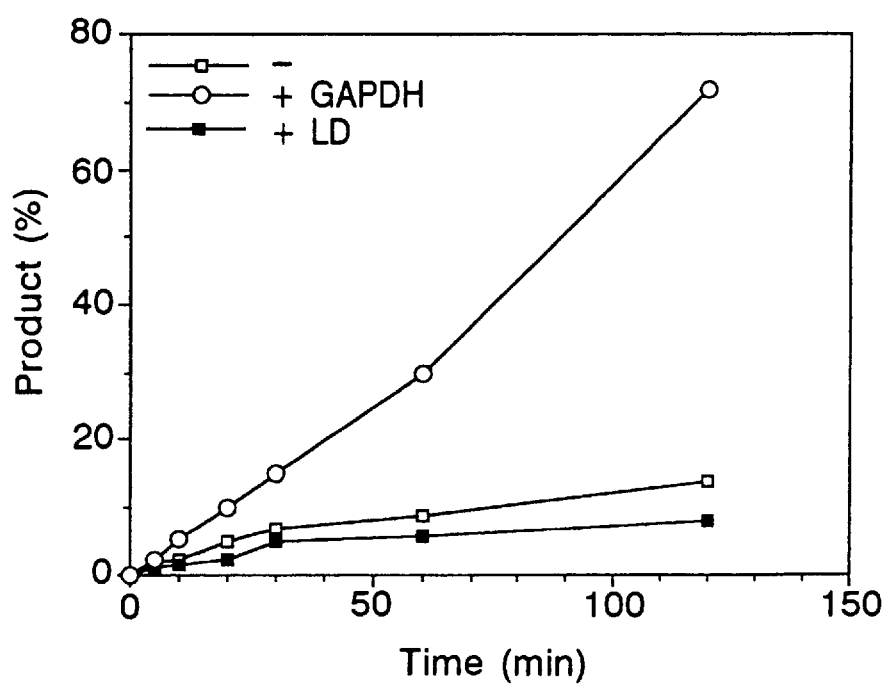

FIG. 34A–34B: Effect of GAPDH on IL2-Rz2 DNA-armed ribozyme (A) Secondary structure of the ribozyme. (B) Quantification of the rate of cleavage of the ribozyme in the absence and presence of GAPDH or LD. Conditions for cleavage are as in FIG. 32.

Figure 35A:
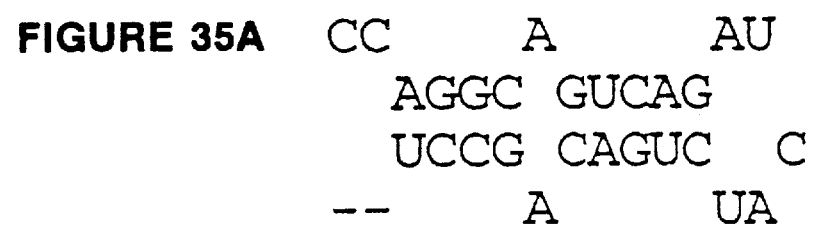

FIG. 35A–35B: GAPDH destabilizes a stable RNA duplex within a 27-mer TNFα-Rz substrate.

FIG. 35(A) Secondary structure of the substrate. FIG. 35(B) A Phospho-Imager printout. TNFα-Rz and δ-ATP-labelled 27-mer substrate were incubated in cleavage reactions in the absence (–) or in the presence of 100 or 200 ng/μl GAPDH for 120 minutes and then analyzed by 15% denaturing gel electrophoresis.

Figure 36:
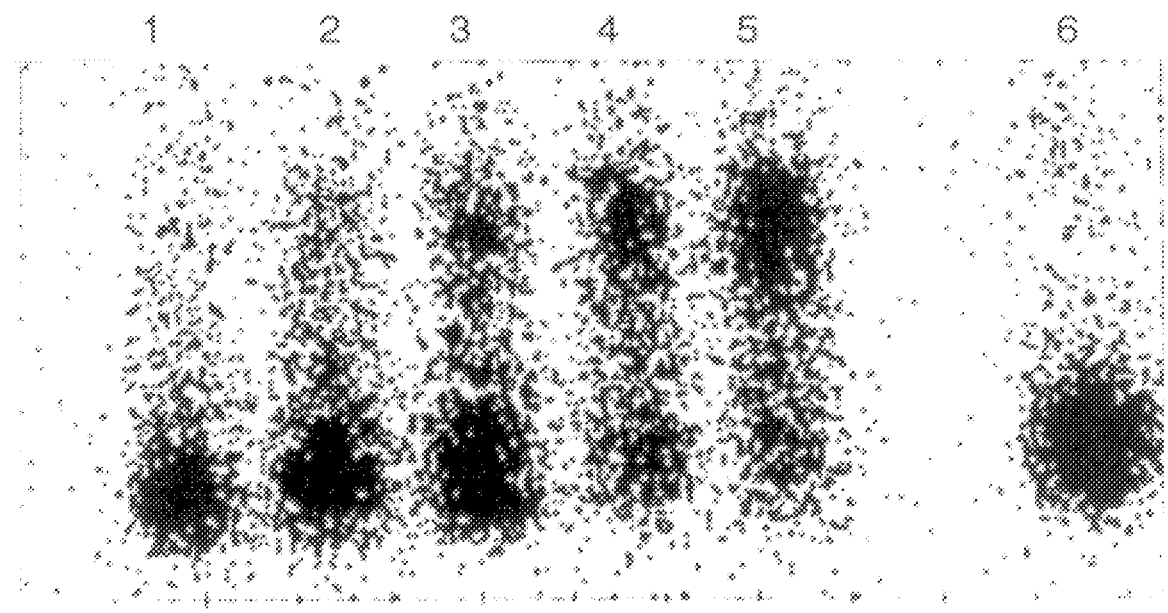

FIG. 36: GAPDH enhances the dissociation products from the ribozyme

Equilibrium binding of the 5'end cleavage product to IL-2-Rz1. A Phospho-Imager printout of $^{32}$P-UCCUGUC cleavage product binding to increasing concentrations of IL-2-Rz (Lane 1 to 5). The bound products as shown in lane 5 were dissociated by the addition of 200 ng/μl of GAPDH (lane 6).

Figure 37:
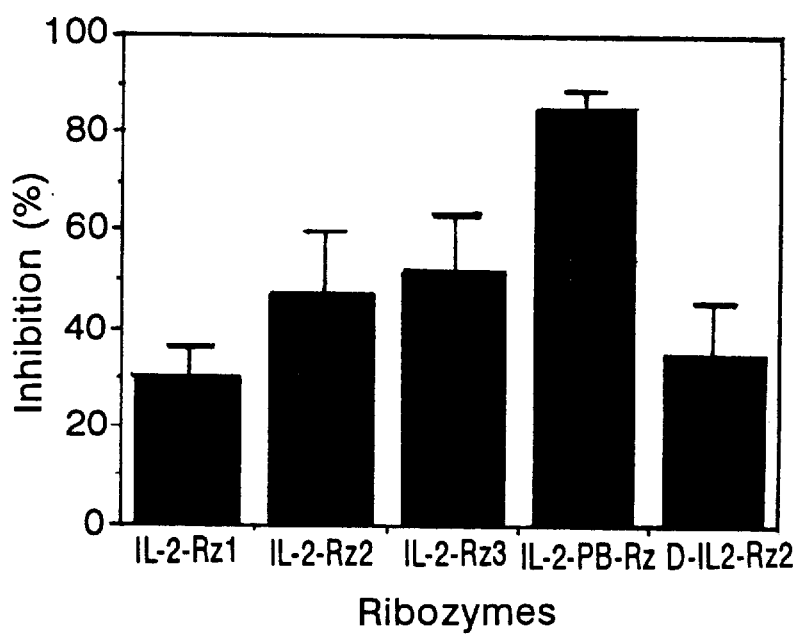

FIG. 37: In vivo activity of IL-2 ribozymes on IL-2 protein synthesis by PHA activated T cells An enriched population of PB T cells were transfected with the test molecules (5 μM) for 20 hrs. Following transfection, the cells were stimulated with PHA (5 μg/ml) for a period of 12 hrs, and the IL-2 protein secreted by the cells was assayed by CTLL-2 bio-assay. D=DNA armed ribozyme.

DETAILED DESCRIPTION OF THE INVENTION

The invention described herein relates to TNF-α ribozymes or compounds having the structure (SEQ ID NO:1):

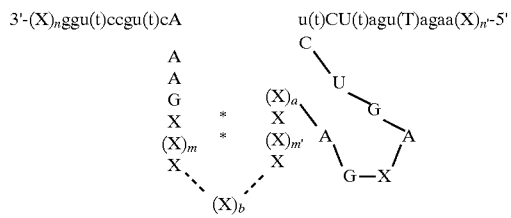

wherein each X represents a ribonucleotide or a deoxyribonucleotide which is the same or different and may be modified or substituted in its sugar, phosphate or base; wherein each of A, C, U, and G represents a ribonucleotide and a, c, u(t), and g represents a ribonucleotide or deoxyribonucleotide which may be unmodified or modified or substituted in its sugar, phosphate or base; wherein each of $(X)_n$ and $(X)_{n'}$ represents an oligonucleotide having a predetermined sequence; wherein each of n and n' represents an integer from 0 to 100; wherein each * represents base pairing between the nucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1 and typically less than 100; wherein each of the dashed lines independently represents either a chemical linkage providing covalent bonds between the nucleotides located on either side thereof or the absence of any such chemical linkage; and wherein $(X)_b$ represents an oligonucleotide which may be present or absent with the proviso that b represents an integer which is greater than or equal to 2 if $(X)_b$ is present.

Such compounds are targeted for cleaving the TNF-α mRNA in vivo. Site directed mutagenesis in the hybridizing arms ggu(t)ccgu(t)cA and u(t)cu(t)agu(t)agaa (SEQ ID NO:2) is possible provided that sufficient complementarily is maintained so that the compound hybridizes to the TNF-α mRNA in vivo. All RNA compounds are also part of the invention along with compounds with DNA arms and an RNA catalytic region.

Also part of the invention are compounds in which $(X)_n$ or $(X)_{n'}$ is absent. One form of the compound described above has the structure below (SEQ ID NO:3):

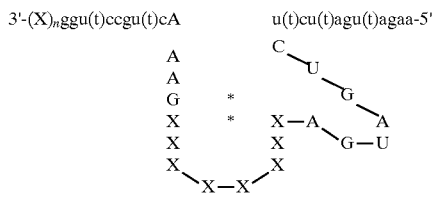

where the nucleotides are defined as above. An all RNA version of the compound is also described. Further the compound may have the structure (SEQ ID NO:4):

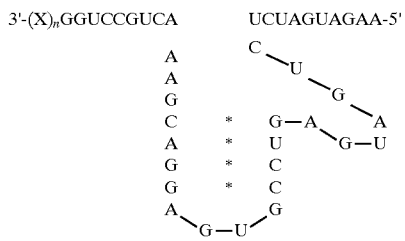

wherein $(X)_n$ represents an oligoribonucleotide.

Further the compound may have the structure (SEQ ID NO:27) where the 3' end is a TNF-α antisense molecule targeted for a different target on the TNF-α gene.

3'-UUAAGUACUCGUGACUUUCGUAC-

-UAGGCCCUGCACCUCGACCGGAA-

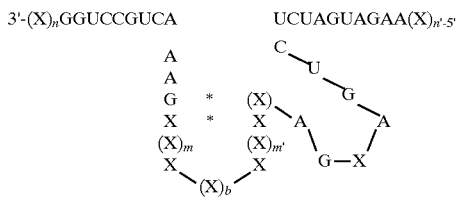

The invention further includes a compound that is a multiple ribozyme having the structure:

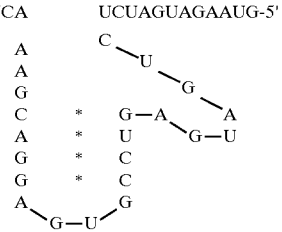

wherein each Q represents the compounds above which may be the same or different; wherein each Z represents a ribonucleotide or a deoxyribonucleotide which is the same or different and may be modified or substituted in its sugar, phosphate or base; wherein each of r and s represents an integer which may be greater than or equal to 0; and wherein z represents an integer greater than or equal to 1.

Further, this invention relates to compounds and methods for increasing protein production by increasing the steady state level of mRNA and by decreasing the rate of intracellular degradation of an mRNA of interest. Such compounds and methods are useful for increasing the stability, and therefore the effectiveness of MRNA using ribozymes and antisense RNA. The compounds and methods of this invention also can be utilized to increase the production of proteins by increasing the quantity of mRNA available to be transcribed.

Ribozymes are RNAs capable of catalyzing RNA cleavage reactions. The simplest and most commonly used type of ribozyme is the hammerhead ribozyme which contains a conserved catalytic domain and flanking sequences that hybridize with the substrate RNA (Haseloff et al. PCT International Publication No WO 89/05852). Hammerhead ribozymes can be targeted against any RNA sequence that contains an XUX triplet amenable for cleavage. Several studies have demonstrated the ability of these ribozymes to cleave a target RNA in vivo and suppress protein expression. Other classes of ribozymes are tetrahymena IVS (Group I Intron) (Cech et al. U.S. Pat. No. 4,740,463, issued Apr. 26, 1988), RNAse P (Altman et al. PCT International Publication No WO 92/03566), hepatitis delta ribozymes (e.g. Blumenfeld et al. PCT International Application No. WO/90/05157) and hairpin ribozymes (European Patent Application No. EP 360,257, Hampel et al. Nuc. Acids Res. (1990) 18:299–304).

The stabilized mRNAs of the claimed invention may be further stabilized using methods described in the literature for example the use of transcription terminators on the 3' end such as the T7 terminator, ρ-independent terminator, cry element (Gelfand et al. U.S. Pat. No. 4,666,848, issued May 19, 1987) or the TrpE terminator. Furthermore, sequences such as the poly(A) addition signal AATAAA may be added and strategies involving changing the length of the 3' non-coding region may be used (see Gillies, U.S. Pat. No. 5,149,635, issued Sep. 22, 1992.) These techniques can be used to stabilize mRNA for ribozyme, antisense, or protein production purposes.

Specifically, this invention encompasses RNA molecules capable of conferring stability on single stranded RNA represented by the $(X)_n$ and $(X)_{n'}$ of interest which have the structure (SEQ ID NO:5):

wherein each X represents a ribonucleotide which may be the same or different; wherein each of $(X)_n$ and $(X)_{n'}$ represents an oligonucleotide having a predetermined sequence; wherein each of n and n' represents an integer from 0 to 1000; wherein each * represents base pairing between the ribonucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

Another embodiment of the invention is an RNA molecule having the structure (SEQ ID NO:6):

3'—(X)nGGUCCGUCAG*UCUAGUAGAA(X)n'—5' wherein each X represents a ribonucleotide which may be the same or different; wherein G* may be present or absent; and $(X)_n$ and $(X)_{n'}$ are as defined above.

As described above site directed mutagenesis is possible in the GGUCCGUCA and UCUAGUAGAA (SEQ ID NO:7) respectively in either the TNF-α ribozyme or the TNF-α antisense structure. Variations in the arms binding the RNA in vivo considerable are possible. Compounds missing either the 3' or the 5' arm are also encompassed within the invention described herein. Preferably, the 5' arm is missing. Also preferably the compounds are linked to the 3' end of the TNF-α ribozyme. In one embodiment multiple versions of the 3' end of the TNF-α ribozyme are used as stabilizing elements.

In one embodiment of the invention $(X)_n$ or $(X)_{n'}$ encodes at least one ribozyme. The ribozyme may be a hairpin ribozyme, RNAase P, or more preferably a hammerhead ribozyme. In the case wherein $(X)_n$ or $(X)_{n'}$ encodes at least one hammerhead ribozyme it may have the structure (SEQ ID NO:8):

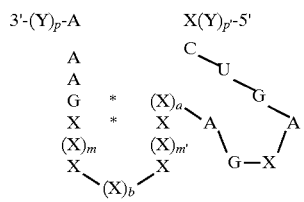

wherein each of X and Y represents a ribonucleotide which may be the same or different; wherein each of $(Y)_p$ and $(Y)_{p'}$ represents an oligonucleotide having a predetermined sequence which is capable of hybridizing with an RNA target sequence to be cleaved; wherein each of p and p' represents an integer which defines the number of ribonucleotides in the oligonucleotide with the proviso that the sum of p+p' is sufficient to allow the ribozyme to hybridize with the RNA target sequence; wherein each * represents base pairing between the ribonucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

In one embodiment of the invention the RNA molecule may have the following structures (SEQ ID NO:9,10):

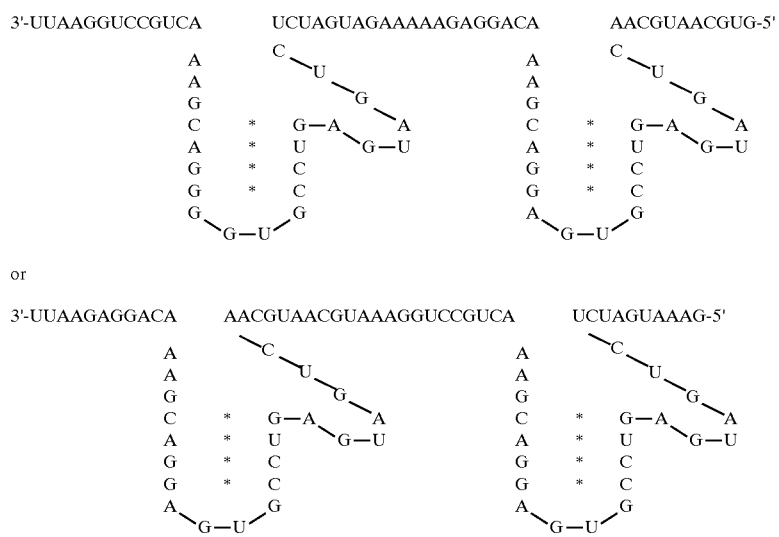

Additional embodiments of the invention may have the following structures (SEQ ID NO:11–13):

or

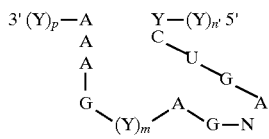

For the specific IL-2 ribozymes above one with skill in the art will recognize that one can change the AAA linker.

Alternatively, $(X)_n$ or $(X)_{n'}$ may have the structure:

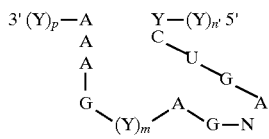

wherein each Y represents a ribonucleotide or a deoxyribonucleotide which is the same or different and may be modified or substituted in its sugar, phosphate or base; wherein $(Y)_n$ and $(Y)_{n'}$ represent oligonucleotides in which n and n' are integers which define the number of nucleotides in the oligonucleotides, such oligonucleotides having predetermined sequences, sufficiently complementary to a predefined RNA target sequence to be cleaved, to allow hybridization to the RNA target sequence, such predefined RNA target sequence not being present within the compound; wherein N may be adenine, guanine, cytosine or uracil; wherein each solid line represents a chemical linkage providing covalent bonds between the nucleotides located on either side thereof; wherein M represents an integer from 2 to 20; and wherein none of the nucleotides $(Y)_m$ are Watson-Crick base-paired to any other nucleotide within the compound.

Another embodiment of the claimed invention is the RNA molecule described above which may also be used to stabilize an mRNA which encodes a polypeptide. Particularly, the RNA compounds are useful for the production of proteins of industrial of commercial significance. Many such proteins are either already available commercially or are under commercial development. Examples of such proteins include human and animal growth hormones, immunomodulators, growth factors, blood proteins, inhibitors, enzymes and vaccines. These mRNAs may include mRNA encoding tissue plasminogen activators, erythropoietin, and factor VIII, factor VII, human serum albumin, hemoglobin, antithrombin III, von Willebrand factor, t-PA, urokinase, streptokinase, hirudin, protein C, apolipopropteins, Mullerian inhibiting substance, lysozyme, interferon-α, interferon-β, interferon-δ, IL-1, IL-2, IL-3, IL-6, TNF, G-CSF, M-CSF, GM-CSF, FGF, EGF, PDGF, EPO, fibronectin, somatostatin, insulin, β-endorphin, Hepatitis B protein, Whooping cough protein and malaria proteins.

The invention may be employed to improve the production of such protein in cell culture, particularly in animal cell culture such as in CHO cells grown in culture and thereby reduce the substantial costs involved in commercial production of such proteins.

In another embodiment of the invention, $(X)_n$ or $(X)_{n'}$ is a ribozyme capable of cleaving targets. Alternatively, $(X)_n$ or $(X)_{n'}$ is an antisense sequence capable of hybridizing to an RNA indigenous to a mammal or plant and thereby deactivating it (for plants see Shewmaker et al. U.S. Pat. No. 5,107,065, issued Apr. 21, 1992). Diseases or infections which may be treated in plants with ribozymes of this invention include fungal infection, bacterial infections (such as Crown-Gall disease) and disease associated with plant viral infection. Of particular interest would be compounds targeting genes associated with male gametophyte development. Examples include PCT International Publication No. WO 92/18625, entitled "Male-Sterile Plants, Method For Obtaining Male-Sterile Plants And Recombinant DNA For Use Therein"; U.S. Pat. No. 5,254,802, entitled "Male Sterile Brassica Plants," S. Hoekstra et al.; PCT International Publication No. WO 93/25695, entitled "Maintenance of Male-Sterile Plants," M. Williams et al., claiming the priority of U.S. Ser. Nos. 07/970,840 and 07/899,072; PCT International Publication No. WO 94/25593, entitled "Method For Obtaining Male-Sterile Plants" Stiekema et al.; PCT International Publication No. WO 94/29465, entitled "Process For Generating Male Sterile Plants" Dirks et al.

Another embodiment of this invention is a plant nucleic acid expression sequence that includes a gene sequence flanked by promoter and terminator sequences at its 5'- and 3'-ends respectively wherein the genetic sequence on expression provides a ribozyme RNA. The nucleic acid sequence may further be part of a DNA transfer vector suitable for transfer into a plant cell and insertion into a plant genome. In a most preferred embodiment of the present invention, the nucleic acid sequence is carried by a broad host range plasmid and which is capable of transformation into plant cells using Agrobacterium comprising Ti DNA on the left and right borders, a selectable marker for prokaryotes, a selectable marker for eukaryotes, a bacterial origin of replication and optional plant promoters and terminators such as pGA470. The present invention also includes other means of transfer such as genetic bullets (e.g. DNA-coated tungsten particles, high-velocity micro projectile bombardment) and electroporation among others [Maliga, P. (1993) Towards plastid transformation in flowering plants. Tibtech 11:101–106; Bryant, J. (1992) Transgenic wheat plants: the end of the beginning. Tibtech 10:342–343; Shimamoto, K., et al. (1989) Fertile transgenic rice plants regenerated from transformed protoplasts. Nature 338:274–276.

The present invention is also directed to a transgenic plant resistant to a virus, its genome containing a sequence which gives rise, on transcription, to the nucleic acid molecule mentioned above. This transgenic plant, including fruits, and seeds thereof, may be from alfalfa, apple, arabidopsis, barley, bean, canola (oilseed rape), cantaloupe, carnation, cassava, clover, corn, cotton, courgette, cucumber, grape, melon, papaya, pepper, potato, rice, rose, snap dragon, soybean, squash, strawberry, sunflower, sweet pepper, tobacco, tomato, walnut, wheat or zucchini. Also included are the plant cells transformed by the above-mentioned transfer vector, as well as a prokaryotic, eukaryotic or yeast cell, plant or animal, comprising a nucleotide sequence which is, or on transcription gives rise to, the nucleic acid molecule.

Further, the targets for the ribozyme or antisense sequence may be a viral gene including viral targets such as cytomegalovirus, hepatitis, herpes, HIV, EBV, papilloma virus, cytomegalovirus, rhinovirus, influenza virus, varicella-zoster virus, parainfluenza virus, mumps virus, respiratory syncytial virus, adenovirus, measles virus, rubella virus, human parvovirus, poliovirus, rotavirus, echovirus, arbovirus, human T cell leukemia-lymphoma virus.

One embodiment of this invention is a tissue specific expression system in which catalytic mRNA is delivered specifically to one or more tissues. Viral genes are often expressed in a tissue specific manner, thus, these specific viral promoters may be utilized in a viral vector expression construct to direct gene expression to specific tissues. Examples of tissue specific viral promoters include the Hepatitis B promoter directed to the liver, the rabies promoter directed to the brain, and the Herpes simplex and zoster promoter directed to the nerves.

The invention also embodies methods of production of the compounds and RNA molecules described above comprising the steps of: (a) ligating into a transfer vector comprised of DNA, RNA or a combination thereof a nucleotide sequence corresponding to said compound; (b) transcribing the nucleotide sequence of step (a) with RNA polymerase; and (c) recovering the compound. The invention also includes transfer vectors, bacterial or phage, comprised of RNA or DNA or a combination thereof containing a nucleotide sequence which on transcription gives rise to the compounds or RNA molecules described above.

Further, many methods have been developed for introducing cloned eukaryotic DNAs into cultured mammalian cells (Sambrook et al. Molecular Cloning: A Laboratory Manual 2ed. Cold Spring Harbor Laboratory Press 1989): Calcium phosphate or DEAE-dextran-mediated transfection; Polybrene; Protoplast fusion; Electroporation; and Direct microinjection into nuclei.

The invention provides a method of treating a disorder associated with over expression of TNF-α which comprises administering to a subject an effective amount of the TNF-α ribozyme so as to reduce the overexpression of TNF-α and thereby treat the disorder. Such disorders include rheumatic arthritis, AIDS, septic shock, graft versus host disease, the cachexia associated with cancer and autoimmune diseases. The invention also provides a method of treating other disorders which would require the overexpression of a certain RNA molecule including an mRNA molecule, a ribozyme molecule or an antisense RNA molecule. Such disorders include, immunodeficiency syndromes, adenosine deaminase deficiency, sickle cell anemia, thalassemia, hemophilia, diabetes, a-antitrypsin deficiency, Alzheimer's Disease, psoriasis, inflammatory diseases, restenosis, hypertension, osteoarthritis, asthma, neoplastic disorders, leukemias, Burkitt's lymphoma, colon carcinomas, neuroblastoma, lung cancer and metabolic disorders affecting cholesterol metabolism and growth hormone metabolism (See U.S. Pat. No. 5,399,346, Anderson, F. et al., entitled "Gene Therapy", Mar. 21, 1995; PCT International Publication No. WO 94/02595, Sullivan, S. M. and Draper, K. G., entitled "Method and Reagent for Treatment of Animal Diseases", filed Jul. 2, 1993; PCT International Publication No. WO 93/23057, Thompson, J. D. and Draper, K. G., entitled "Method and Reagent for Inhibiting Cancer Development", filed May 13, 1993).

The invention also provides a method of cleavage or deactivation of a specific RNA target sequence using the RNA molecules described above. Such RNA sequences may be indigenous to a mammal or a plant. It is particularly suited for targeting viral genes such as HIV (see Goodchild et al. U.S. Pat. No. 4,806,463, issued Feb. 21, 1989).

Optimization of the expression of the therapeutic RNA molecules may require tissue specific promoters to be incorporated into an expression vector. Brain specific promoters include neuron specific enolase promoter, human β-actin gene promoter, human platelet derived growth factor B chain gene promoter, sodium channel gene promoter, and myelin basic protein gene promoter. Skin specific promoters include keratin promoters, and collagen promoters. Cardiovascular specific promoters include angiotensin converting enzyme promoter.

Another embodiment of this invention is a stabilized RNA composition which includes an isolated ribozyme, mRNA or antisense RNA molecule and glyceraldehyde-3-phosphate dehydrogenase (GAPDH) polypeptide or a portion thereof which is capable of binding a TNF-α ribozyme motif. This composition may contain a TNF-α ribozyme. A peptide derived from GAPDH has been shown to bind to and stabilize RNA and may be useful in the stabilization of therapeutic RNA molecules in a cell. The GAPDH peptide has been shown to enhance the cleavage activity of a ribozyme and therefore would increase the effectiveness of any one ribozyme molecule delivered to a cell.

Another embodiment of this invention is a method for enhancing the activity of an RNA molecule in a cell. In this method, a nucleic acid molecule encoding GAPDH polypeptide or a portion thereof and the RNA molecule are delivered into the cell such that the nucleic acid molecule is expressed and stabilizes the RNA molecule and enhances the activity of the RNA molecule. The RNA molecule may be an mRNA molecule, a ribozyme or an antisense RNA molecule. In this method, the RNA molecule may be a therapeutic RNA molecule.

Another embodiment of this invention is a method to stabilize an RNA molecule which may be an mRNA molecule, a ribozyme or an antisense RNA molecule, wherein a nucleic acid molecule encoding GAPDH polypeptide or a portion thereof and the RNA molecule are delivered into a cell such that the nucleic acid molecule is expressed and stabilizes the RNA molecule. This stabilization may be useful in certain gene therapy protocols in which RNA is delivered into a target cell and the therapeutic value of the RNA is dependent upon its stability.

In the compounds and methods described herein the respective 5' and 3' termini of the groups $(X)_n$ and $(X)_{n'}$ may be modified to stabilize the endonuclease from degradation.

For example, blocking groups may be added to prevent terminal nuclease attack, in particular 3'–5' progressive exonuclease activity. By way of example, blocking groups may be selected from optionally substituted alkyl, optionally substituted phenyl, optionally substituted alkanoyl. Optional substituents may be selected from C1–C5 alkoxy and the like. Alternatively, nucleotide analogues such as phosphothioates, methylphosphonates or phosphoramidates or nucleoside derivatives (such as α-anomers of the ribose moiety) which are resistant to nuclease attack may be employed as terminal blocking groups.

Alternatively, non-nucleic acid groups which alter the susceptibility of the endonuclease molecule to other nucleases may be inserted into the 3' and/or 5' end of the endonuclease. For example, 9-amino-acridine attached to the endonuclease may act as a terminal blocking group to generate resistance to nuclease attack on the endonuclease molecules and/or as an intercalating agent to aid endonucleolytic activity. It will be readily appreciated that a variety of other chemical groups, e.g. spermine or spermidine could be used in a related manner.

Endonucleases of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the endonucleases of the present invention may be associated with RNA binding peptides or proteins which may assist in bringing the endonuclease into juxtaposition with a target nucleic acid such that hybridization and cleavage of the target sequence may take place. Nucleotide sequences may be incorporated into the 5' and 3' ends of the groups $(X)_n$ and $(X)_{n'}$ to increase affinity for substrates. Such additional nucleotide sequences may form triple helices with target sequences (Strobel, S. A., et al., (1991) Nature 350:172–174 and references therein which are incorporated by reference) which may enable interaction with intramolecularly folded substrate. Alternatively, modified bases (non-natural or modified bases as described in Principles of Nucleic Acid Structure, Supra) bases within the additional nucleotide sequences may be used that will associate with either single stranded or duplex DNA generating base pair, triplet, or quadruplet, interactions with nucleotides in the substrate. Suitable bases would include inosine, 5'-methylcytosine, 5' -bromouracil and other such bases as are well known in the art, as described, for example, in Principles of Nucleic Acid Structure, Supra.

Synthetic preparations of mRNA are well known (see Sambrook et al. Molecular Cloning: A Laboratory Manual 2ed. Cold Spring Harbor Laboratory Press 1989). Mixed DNA-RNA oligomers with modified base pairs for the TNF-α ribozyme can be prepared by commercially available DNA synthesizers such as those produced by Applied Biosystems, Biosearch, or Milligen (see, e.g., Perrault et al., Nature, 344:565–567 (1990, for derivatives Uhlmann, E. and Peyman, A. Chemical Reviews (1990) 90:543–584, H-phosphonate monomers see Agrawal et al. U.S. Pat. No. 5,149,798).

The proteins which bind the conserved TNF-α motif may serve to increase the rate and specificity of the ribozyme reaction. Recently, Tsuchihashi et al. reported that the p7 nucleocapsid (NC) protein accelerates the rate of cleavage of a hammerhead ribozyme by 10–20 fold (Science (1993) 262:99–102). Accordingly, the protein which binds the TNF-α motif may have a similar effect.

An "effective amount" as used herein refers to that amount which provides a desired effect in a mammal having given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the oligonucleotide, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils) . Also comprehended by the invention are particulate compositions coated with polymers (e.g., polyoxamers or polyoxamines) and oligonucleotides coupled to antibodies directed against tissue-specific receptors, ligands or antigens or coupled to ligands of tissue-specific receptors. Further, specific nucleotide sequences may be added to target the oligonucleotides of this invention to the nucleus, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, a aerosols, or other inhalants. The oligonucleotides may be encapsulated in a wafer, wax, film or solid carrier, including chewing gums. Permeation enhancers to aid in transport to movement across the epithelial layer are also known in the art and include, but are not limited to, dimethyl sulfoxide and glycols.

This invention is illustrated in the Experimental Detail sections which follow. These sections are set forth to aid in an understanding of the invention but are not intended to, and should not be construed to, limit in any way the invention as set forth in the claims which follow thereafter.

EXPERIMENTAL DETAILS

Example 1: Targeted ribozymes cut TNF-α RNA in vitro

Three hammerhead ribozymes (Haseloff & Gerlach, 1988) designed to cleave the TNF-α RNA is shown in FIG.

1. Their in vitro activities were studied using as target total RNA extracted from PBMNC after stimulation of TNF-α gene transcription by phorbol 12-myristate 13-acetate (PMA) and concanavalin A (Con-A) as described by English et al. (1991). Ribozyme A contained a bacteriophage T7 terminator at its 3' end while ribozyme B did not. Ribozyme II lacked the underlined restriction sites. FIG. 2 shows ribozyme-mediated RNA cleavage was assayed by gel electrophoresis and Northern blot hybridization using TNF-α probe. The TNF-α RNA fragments cut by ribozyme cleaved the approximately 1800 nucleotide-long target RNA into fragments of 1420 and 380 nucleotides. The sizes of the TNF-α fragments of the TNF-α fragments produced by the ribozymes were consistent with the location of predicted site for cleavage. Thus, ribozymes A and B cleave the TNF-α target in vitro in the presence of unrelated RNAs.

Stability of ribozymes A, B, and II in living cells

Stability of ribozyme A, B and II in living cells is shown in FIGS. 3 and 4. Since the cell membrane presents a substantial barrier to the entry of highly charged, high molecular weight molecules, delivering such molecules to the cytoplasm is a major task. To overcome this, transfection techniques such as cationic liposome-mediated transfection (Malone et al., (1989) Proc. Natl. Acad. Sci., USA 86:6077–6081), electroporation (Callis et al., (1987) Nucl. Acids. Res. 15:5823–5831) and microinjection (Rosa et al., (1989) J. Cell. Biol. 109:17–34) have been developed. Since the liposome-based method appears to be the most versatile, its ability to deliver enough functional ribozyme to successfully cleave TNF-α RNA was tested.

The efficiency of RNA transfection was first measured in HL60 cells, as determined by the measurement of cell-associated intact $^{32}$P-labelled RNA. Following transfection with ribozymes, cells were washed with Hank's buffered salt solution (GIBCO). Total RNA was prepared from cells and the RNA species were separated by gel electrophoresis. The radioactivity contained in the ribozyme RNA was then determined. The results indicate that the radioactive bands varied from 2 to 4% of the initial RNA added to the liposomes during the transfection period of between 8 and 20 hours. This corresponds to a delivery of approximately 300,000 molecules of ribozyme A per cell.

FIG. 4 shows stability of ribozymes A, B, and II. Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 μl) of serum free medium was added to polystyrene tubes followed by 35 μg of lipofectin (Bethesda Research Laboratories), 10 μg of carrier RNA (*E. coli.* tRNA), 3×10$^6$ disints min of $^{32}$P-labelled capped ribozyme A, B or II (5 μg). The tubes were immediately mixed. The cells were resuspended in a mixture of serum-free medium lipofectin/RNA/carrier RNA and returned to the incubator for 20 h. Following transfection cells were washed 3 times with Hank's buffered saline solution and then returned to the incubator with RPMI supplemented with 20% FCS. Cells (10$^6$) were harvested at the times indicated above each lane, and total RNA was prepared and analyzed by 15% polyacrylamide gel with 7M-urea. The RNA samples used for transfection are indicated at the top of FIG. 4. A sample (50 μM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris-HCl (pH 7.5), 5 mM-KCl, 140 mM-NaCl, 5 mM-dithiothreitol and 04% (w/v) Nonidet P40 for 10 min at 4° C. and the nuclei were collected by centrifugation at 800 g for 5 min. RNA in the supernatant fluid was precipitated and saved as the cytoplasmic fraction. The nuclei were processed as described by Chomezynski & Sacchi (Anal. Biochem (1987) 162:156–160) for total RNA preparation. The arrow indicates the position of ribozyme A monomer. The amount of radioactivity in the ribozyme bands shown in FIG. 4A was determined and expressed as a percentage of the radioactivity present immediately after 20 h transfection time.

FIG. 5: Activity of ribozymes in vivo

Ribozymes and antisense RNA activities in HL60 cells (FIG. 5A) were analyzed after a transfection period (20 h). Following transfection with ribozyme A or antisense RNA, cells were stimulated for 6 h to express TNF-α. RNA was extracted, separated by gel electrophoresis through a 1–2% (w/v) agarose formaldehyde gel, and detected by Northern blotting with radioactive probe for the TNF-α gene. After hybridization with RNAα probe, the filter was stripped and then rehybridized with an actin probe (British Biotechnology Limited). In the case of PBMNC (FIG. 5B) cells were separated (Sioud et al., Scand. J. Immunol. (1990 31:415–421) and washed 4 times with Hank's buffered saline solution and 3 times with serum-free medium. Cells (10$^6$) were transfected and processed as HL60 cells. Lanes 1 and 4, controls (transfected only with carrier RNA) ; lane 2, antisense RNA; lanes 3 and 5, ribozyme A. This autoradiogram was overexposed to display the TNF-α signal in ribozyme A lanes. FIG. 5C shows a radioimmunoassay to TNF-α protein. The amount of TNF-α protein present in the media was determined using the TNF-α [$^{125}$I) assay system (Amersham). Lanes 1 to 5 correspond to lanes 1 to 5 in FIG. 5A and 5B, respectively.

Destruction of endogenous TNF-α RNA in vivo by ribozymes

Experiments were performed to determine if ribozyme A could eliminate its target following RNA transfection. A preliminary time-course study of TNF-α RNA synthesis in HL60 cells indicated that TNF-α RNA could be detected after two hours of stimulation by PMA and Con-A, reaching maximal expression after 4–6 hrs. Cells were transfected with ribozymes, stimulated with PMA and Con-A for 6 hrs, and total RNA was extracted and analyzed by Northern blotting using a TNF-α probe. Since the TNF-α and actin mRNA have approximately the same electrophoretic mobility, the same blot was rehybridized with the actin probe after stripping. Data derived from densitometric scans of underexposed film indicated that the TNF-α signal was reduced by 40% (FIG. 5A, antisense lane) and 90% (FIG. 3A, ribozyme A lane). In addition, a radioimmunoassay was used to measure TNF-α protein in the culture medium. This system has major advantages over bio-assays in that it is specific for TNF-α. The data indicates that HL60 stimulated with PMA and Con-A secrete as much as 1000 fmol of TNF-α per ml but only 150 and 400 when cells are transfected with ribozyme A and antisense, respectively (FIG. 5B).

Since the effect of antisense RNA is less than that of ribozyme A and since both ribozyme A and the antisense RNA were present inside the cells at similar concentrations (data not shown), we suggest that part of the activity of ribozyme A is due to its ability to cleave RNA. Ribozyme-mediated RNA cleavage in vivo has been observed in eukaryotic cells (Saxena & Ackerman, J. Biol. Chem. (1990) 265:17106–17109).

In this case, no cleavage products were seen. As suggested previously (Cotten & Birnstiel, 1989; Sarver et al., 1990; Sioud & Drlica, 1991) the products of ribozyme-mediated cleavage are probably degraded by cellular nucleases (the 5' fragment, although capped at its 5' end, is expected to be rapidly degraded by 3'→5' exonucleases).

The same conditions were used to deliver ribozyme A to PBMNC. As can be seen from FIG. 5A and 5B, ribozyme A reduced the amount of TNF-α RNA by 80% and the TNF-α protein by 70% raising the possibility that liposome-mediated RNA transfection offers a way to deliver ribozymes to wide variety of cell types. During analysis, ribozyme B appeared to induce a similar reduction in TNF-α mRNA as ribozyme A (data not shown). Thus, the addition of T7 transcription terminator may decrease the specific activity of ribozyme A.

FIG. 6: Cellular distribution of TNF-α ribozymes

Figure 1A:
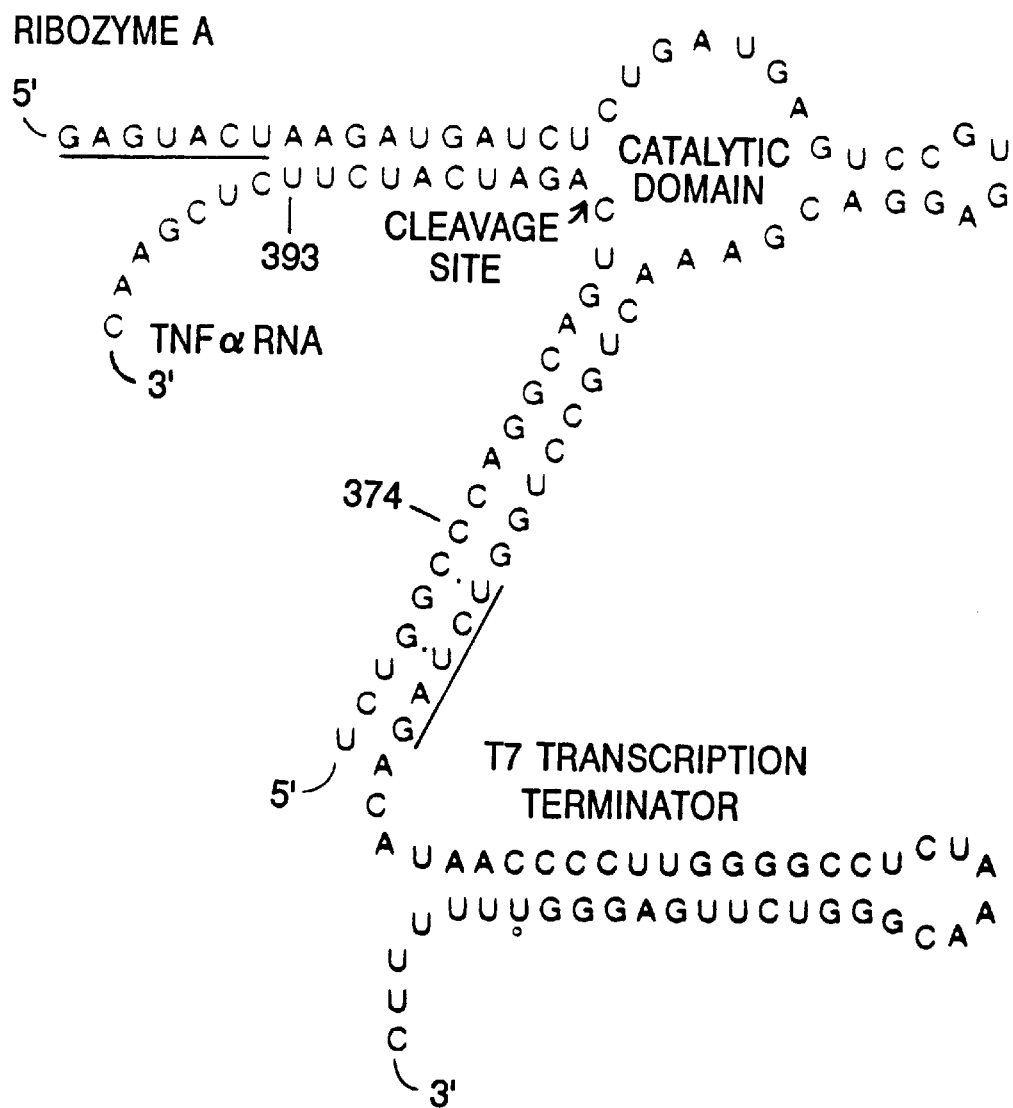
FIGS. 1A–1C shows base-pairing of ribozyme A, B and II with TNF-α RNA template (SEQ ID NO:15–18), respectively.
Figure 1B:
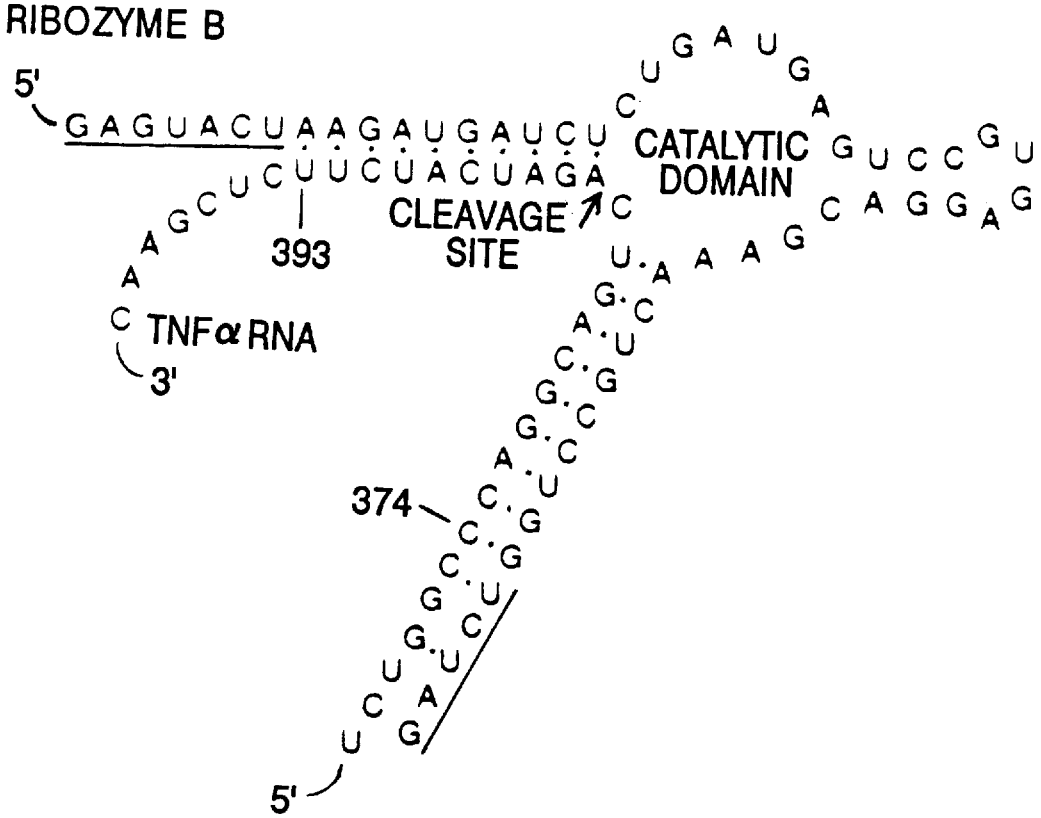
Figure 1C:
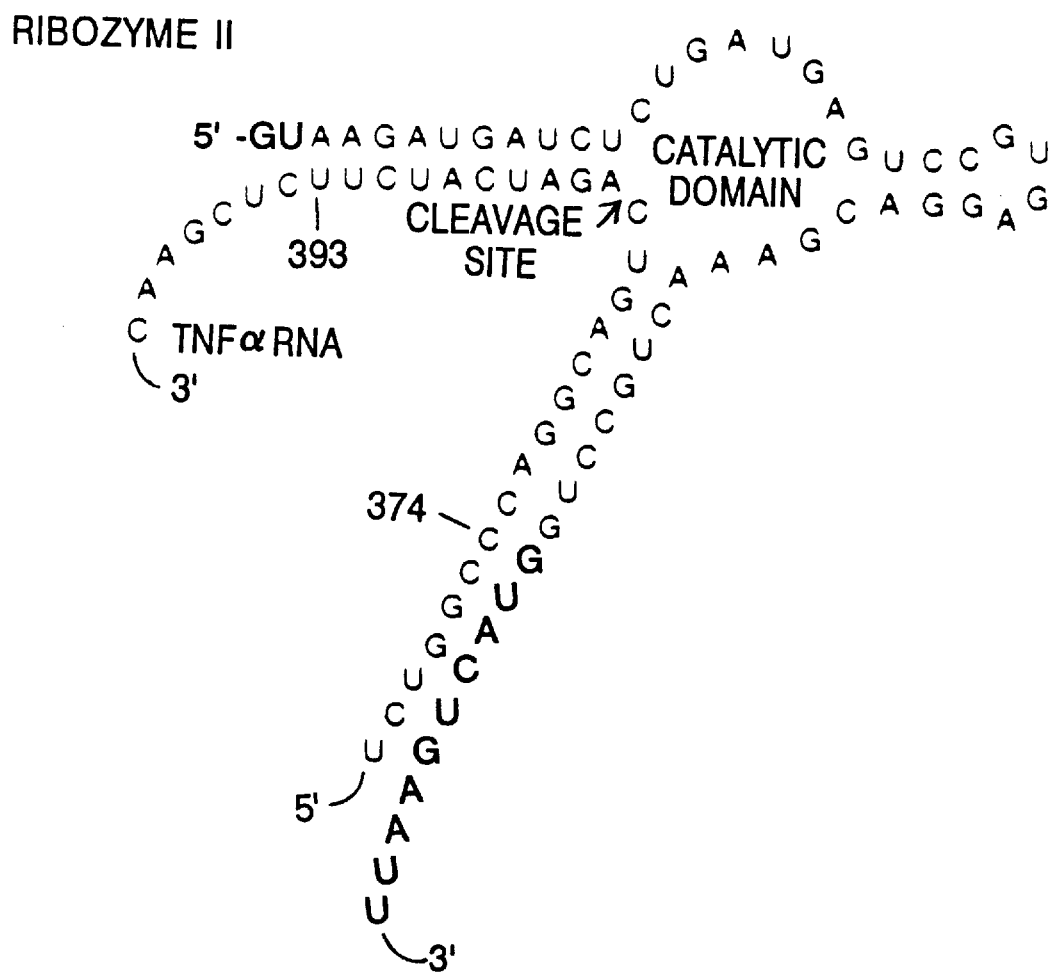

The TNF-α ribozymes (FIG. 1) were unusually stable. They could be detected inside human cells for 7 days, while normally, the ribozymes are unstable in human cells see FIG. 4. Although a cell fractionation study indicated that TNF-α ribozymes can be recovered from the cell, it did not address the possibility that a major portion of the ribozyme was sequestered in places inaccessible to cellular nucleases. To address this question cells were transfected with digoxigenin labelled ribozymes. After 72 hrs post transfection, microscope slides were prepared and the presence of ribozymes was detected by anti-digoxigenin-fluorescein-Fab conjugate. Data presented in FIG. 5A and B indicated that the stabilization effect was not due to any cellular compartmentalization, because upon immunofluorescence staining of the ribozyme, the whole cell acquired the fluorescence. See FIG. 6A and FIG. 6B.

FIG. 7: Electrophoretic mobility shift analysis of TNF-α ribozymes with cellular extracts Our initial hypothesis was that the ribozyme directed against this particular site of tumor necrosis factor is protected by certain cellular factors such as proteins. If proteins were binding to the ribozymes and protecting them from degradation, mobility shift experiments should have detected them. Initial experiments with HL60 cytoplasmic proteins revealed that the complex formation was not inhibited by the presence of poly-(dC) (dI) or by tRNA in the reaction mixture. In these experiments there was still considerable degradation of the ribozyme due to the nucleases present in the extract. When RNAsin was added to the incubation mixture to lower the effect of ribonuclease, a much greater portion of the input RNA was captured in the major complex (FIG. 7B lanes 2, 3 and 4). When cytoplasmic extracts from PBMN cells were used, a complex with low electrophoretic mobility was also detectable (FIG. 7B lanes 6, 7), suggesting that the protein that binds to the ribozyme is a common protein to all cell types. The complexes formed in the presence or absence of RNasin had identical mobilities which suggests that the proteins bind to the full length. Furthermore, the ribozyme that was recovered from the complex following phenol extraction corresponds to the full length ribozyme (FIG. 7B, lane 8).

Complex formation is specific for TNF-α ribozymes

Adding tRNA to the reaction did not diminish the amount of complex formed, suggesting some specific binding to the ribozyme. This specificity of binding was confirmed by the competition assays (FIG. 8). In contrast to tRNA and poly (dCdI), cold ribozymes compete with labelled ribozymes for complex formation. Interestingly, complex formation was not observed with hammerhead ribozymes directed to mRNA of IL-2 or to integrase of HIV. This indicates that the binding was not due to the catalytic domain of TNF-α ribozymes. IL-2 ribozyme is not as stable inside the cell as TNF-α ribozyme and does not exhibit this binding phenomenon. Thus, it is possible that this binding is responsible for the in vivo stability of the TNF-α ribozymes.

TNF-α ribozyme confers stability to other ribozymes

Prior to characterizing the RNA element(s) that protects the TNF-α from degradation, we tested whether this RNA element could be linked to other RNAs and stabilize them. The TNF-α ribozyme was linked to the 3'end of IL-2 ribozyme (FIG. 9) which was unstable alone. As shown in FIG. 10A and B, the IL-2 ribozyme did not form complexes on its own with any cellular factor under our conditions.

The in vivo activity of protected and unprotected IL-2 ribozymes

We know that the inhibition of TNF-α gene expression by its antisense or ribozyme does not significantly effect the IL-2 gene expression. Therefore, the effect of the double ribozyme (IL-2 ribozyme linked to TNF-α ribozyme) on IL-2 gene expression could be investigated precisely.

The ribozyme directed against TNF-α was protected by certain cellular factors which could enhance the stability and/or activity of the ribozyme beyond structural stabilization. Such factor(s) or related compounds may be combined with the ribozyme in an overall gene therapy approach.

Mobility shift experiments have been used to demonstrate successfully that protein(s) do bind to TNF-α ribozyme (see FIGS. 8, 7 and 9). Pretreatment of the complex with proteinase K prior to electrophoresis eliminates the complex (FIG. 11 A, lanes 4 and 5) confirming that the cofactor is of a proteinaceous nature. The degradation of the ribozyme seen in lane 4 is due to the excess of ribonucleases present in this particular cytoplasmic extract (CE). Furthermore UV crosslinking analysis of proteins binding to the TNF-α ribozyme reveal a major ribozyme binding protein as can be seen in FIG. 11C, lane 1.

Similar complex formation was not observed with an integrase ribozyme, thus the protein is specific for TNF-α ribozyme which suggests that the difference in in vivo stability between the integrase ribozyme and TNF-α ribozyme may be due to the protein(s).

We wanted to test whether the linkage of the TNF-α ribozyme to other RNA molecules conferred the protein binding and the in vitro and in vivo stability. In order to answer this question, the following minigenes were constructed:

1) IL-2 ribozyme linked to 5' region of TNF-α ribozyme

Since the TNF-α ribozyme and the integrase or IL-2 ribozyme differ only in the nucleotide sequence complementary to their RNA target, that RNA region is likely to be responsible for the complex formation.

2) IL-2 ribozyme linked to the antisense TNF-α RNA (see FIG. 9)

The genes coding for these molecules were cloned and transcribed in vitro. The radiolabelled RNA molecules were used in gel retardation assays.

Although weak complexes have been detected in some experiments, our data indicate that neither IL-2 linked to the 5' region of TNF-α ribozyme nor the IL-2 ribozyme linked to the antisense bind to protein (For structure see FIG. 9). (FIG. 12A, lanes 4, 5, 7 and 8 and FIG. 12B, lanes 2 and 3). As can be seen from FIG. 12A, degradation of the IL-2 ribozyme and the chimeric molecules in the presence of CE was seen in all the lanes, indicating that the complex formation protects the ribozyme against degradation.

This data suggests that the binding of the protein requires a secondary structure. Since the T7 terminator linked at the 3' end of the TNF-α ribozyme did not affect the binding, it was thought that the ribozyme binding site could be formed between the 5' flanking sequence of TNF-α ribozyme and its catalytic domain. In addition, attempts were made to mimic the secondary structure of TNF-α ribozyme linked to T7 terminator (FIG. 13A).

TNF-α Antisense linked to 3' end of TNF-α ribozyme

The 3' end of the TNF-α ribozyme linked to an antisense molecule was directed against a different target on the TNF-α (FIG. 13B). The antisense molecule has a hairpin structure (keesing loop). Both genes were cloned and transcribed in vitro. The radiolabelled RNA molecules were used in gel retardation assays.

The results (FIG. 14A, lanes 5 and 6) indicate that the antisense linked to 3' end of TNF-α ribozyme binds to protein(s). In addition competition experiments demonstrate that the same protein(s) are responsible for the complex formation, since unlabelled TNF-α ribozyme competes with the chimeric ribozyme for complex formation (FIG. 14B: lanes 3 and 4).

In the second set of experiments the IL-2 ribozyme was linked to the 3' end of TNF-α ribozyme (FIG. 15B). The flanking sequences of IL-2 ribozyme were extended in the construct in order to prevent intramolecular interaction.

The RNA generated from this chimeric ribozyme binds to protein(s) as TNF-α ribozyme (FIG. 16, lane 4). The experimental data suggests that the 5' flanking sequence of TNF-α ribozyme is involved in the binding.

Truncated TNF-α Ribozymes

To test the involvement of the flanking sequences, TNF-α ribozymes truncated at the 5' or 3' flanking sequence (FIG. 17A and 17B, respectively) were constructed.

The genes coding for these ribozymes were cloned and transcribed in vitro. The radioactive RNA molecules were used in gel retardation assays. As can be seen from FIG. 18A lane 4, the 3' end truncated ribozyme binds to proteins. In contrast the 5' truncated TNF-α ribozyme does not form a protein complex (FIG. 18A, lane 6). The weak complex as indicated by * is not always detected as can be seen in FIG. 18C, lane 2. This is probably due to the intramolecular conformation of the ribozyme.

Gel retardation assays were used in order to see whether the 3' end truncated ribozyme binds to proteins from other cell types. As can be seen from FIG. 18D, lanes 2, 3, and 4, the truncated ribozymes bind to proteins from PBMN, HL60 and WH164 cells. Taken together, our experimental data indicate that endogenous proteins from many cell types bind to the 3' truncated TNF-α ribozyme. Thus, the capacity of any ribozyme to bind to protein(s) would depend on its 5' and perhaps 3' base composition.

A possible secondary structure for the TNF-α ribozyme B and II and the putative binding site of the protein are proposed in FIG. 19. Such a structure may or may not include the 5' GU and the AGG on the 3' end.

During this analysis, it was observed that in vitro complex formation protects the ribozyme against degradation (see FIG. 21A). Endogenous protein could be responsible for the unexpected stability of TNF-α ribozymes. Furthermore such endogenous protein(s) may enhance the in vivo ribozyme activity by helping to prevent and resolve misfolded ribozymes.

In vivo stability of IL-2, and IL-2 linked to the 3' end of TNF-α ribozyme.

The stability of IL-2 ribozyme and the IL-2 ribozyme linked to the 3' end of TNF-α ribozyme was investigated. Briefly, HL60 cells growing in log phase in RPMI supplemented with 20% fetal calf sera were transfected with IL-2 ribozyme or IL-2 linked to TNF-α using DOTAP as transfection agent. Following transfection, cells were washed 3 times with Hank's buffered saline solution then returned to the incubator with RPMI supplemented with 20% FCS. Cells contained in 1 ml cultures were harvested at different times. Total RNA was prepared and analyzed by 15% polyacrylamide gel with 7M urea. The radioactivity in the ribozyme bands was determined and expressed as a percentage of the radioactivity present immediately after transfection time (FIG. 20). The data indicate that the chimeric ribozyme is more stable than the IL-2 ribozyme alone.

In vivo activity and cytotoxicity TNF-α ribozyme and TNF-α antisense linked to TNF-α ribozyme The in vivo activity of TNF-α ribozyme, the antisense and the antisense linked to TNF-α ribozyme was investigated using the cytotoxicity assay and radioimmunoassay. In these experiments the cellular internalization of the ribozymes was done by cationic liposome (DOTAP). A 36 nt long antisense complementary to the TNF-α sequence ranging from 56 to 91 (see Pennica et al., 1984, Nature 312:724 for numbering) was linked to the TNF-α ribozyme.

Approximately 100,000 PBMN cells were transfected with the ribozyme for 6 hrs or 12 hrs. The expression of TNF-α was induced with 10 μg of PHA for 16 hrs, and the secreted TNF-α in the media was measured by cytotoxicity assay using L929 cells. TNF-α inhibits growth of L929 cells. A high radioactive count (high level of incorporated $^3$H-thymidine) indicated a low level of TNF-α and hence effective ribozymes in PBMN cells. The level of TNF-α was considerably reduced when the peripheral blood was transfected with ribozymes. In addition, a radioimmunoassay was used to measure TNF-α in the culture medium. This system has a major advantage over bioassay in that it is specific for TNF-α.

The data presented in FIG. 21 indicate that all molecules are active in vivo. As may be expected, the antisense linked to the TNF-α ribozyme has a synergic effect.

One of the major problems when designing treatment is specificity and cytotoxicity. Thus the effects of TNF-α ribozyme and the TNF-α antisense linked to TNF-α ribozyme were investigated on interleukin-2 gene expression to check the specificity and cytotoxicity.

The molecules were delivered to the cells by cationic liposomes. Approximately 100,000 peripheral blood mononuclear cells were transfected with the test molecules for 5 hrs. Following transfection, the cells were stimulated with 5 μg/ml PHA for 16 hours and then the quantity of interleukin-2 secreted in the media is determined using the CTLL2 assay. In this assay, a series of dilutions (¼ to ¹⁄₁₂₈) are made from the supernatant obtained from the controls and from cells transfected with the test molecules. 100 μl from each dilution (done in triplicates) are added to 5,000 CTLL2 cells in 20 μl medium. After 20 hours the cells are pulsed with $^3$H-thymidine for 4 hours, harvested, and then the DNA-associated radioactivity is determined. Interleukin-2 promotes the growth of CTLL2 cells, and a high radioactive count indicates high levels of IL-2, and hence an ineffective ribozyme in PBMN cells. FIG. 22 demonstrates that the expression of interleukin-2 is not effected by the TNF-α ribozyme, and indicates that the ribozyme is not cytotoxic to the cells and that the IL-2 gene expression is not regulated by the level of TNF-α gene expression. This is one of the reasons why the IL-2 is chosen as a second target in the experiments.

In vivo activity of IL-2 ribozyme and the IL-2 ribozyme linked to the 3' end of TNF-α ribozyme was investigated by CTLL2 assay Approximately 100,000 PBMN cells were transfected with the different molecules (25 μM final concentration) using DOTAP as a cationic liposome. After 8 hrs of transfection the cells were stimulated with PHA (5 μg/ml) for 16 hrs and then the IL-2 in the media was assayed by the CTLL2 assay as shown in FIG. 22.

The data presented in FIG. 23 indicate that both ribozymes are active. The activity of IL-2 ribozyme linked to the 3' end of TNF-α ribozyme is much higher than the IL-2 alone, suggesting that the protein may enhance both the stability and the activity of the ribozyme.

Another way to measure the interleukin 2 gene expression is to pulse the PBMN cells directly with $^3$H-thymidine Following transfection, the cells were stimulated with PHA for 48 hrs, pulsed with $^3$H-thymidine and then harvested 18 hrs later. In this assay, the IL-2 promotes the growth of T cells and a high radioactive count indicates a high level of IL-2 and hence, an ineffective molecule. The results of 3 experiments are presented below.

|  | A | B | C | D |
|---|---|---|---|---|
| exp1: | 2478 | 1566 | 566 | 130 |
| exp2 | 4641 | 1862 | 2000 | 213 |
| exp3 | 11403 | 5285 | 3586 | 32 |
| Medium | 6174 | 2904 | 2050 | 125 |
| % of inhibition | 0 | 53 | 67 | 0 |

A: Control
B: Cells transfected with IL-2 ribozyme alone.
C: Cells transfected with IL-2 ribozyme linked to 3' end of TNF ribozyme.
D: Unstimulated cells.

The medium presented in the above table indicates that both ribozymes are active in vivo. The IL-2 ribozyme linked to TNF-α ribozyme is more active than the IL-2 alone.

It has been demonstrated herein that the 3' truncated ribozyme binds to proteins as TNF-α ribozyme. Thus this truncated ribozyme could be used as a stabilizer through the protein(s). In addition, this truncated ribozyme will be inactive, since it lacks its 3' end flanking sequences. The in vivo activity of TNF-α ribozyme and the 3' truncated ribozyme has been investigated at various transfection times. Cells were transfected with the TNF-α ribozyme or the 3' truncated ribozyme using DOTAP. In these experiments the cells were stimulated with LPS (100 mg/ml) after 6, 20, 42 or 72 hrs post transfection time. The TNF-α contained in the media was measured by radioimmunoassay (Amersham). The data is expressed in fmol/ml.

| Hrs post transfection time | Cells transfected by 3' truncated ribozyme | Cells transfected by TNFα ribozyme | unst cells |
|---|---|---|---|
| 6 | 284 | 180 | 24 |
| 20 | 350 | 116 | 52 |
| 42 | 1250 | 370 | 1250 |
| 72 | 1250 | 430 | 1250 |

These data indicate that the truncated ribozyme is not active compared to the TNF-α ribozyme and demonstrate that the TNF-α ribozyme is active even 72 hrs post transfection time.

As can be seen after 42 hrs the unstimulated cells secreted the same amount of TNF-α as the controls which have been stimulated. This may be due to the fact that the cells have been stimulated through contact with the plastic (it is known that long exposure of the cells to plastic may stimulate the expression of some lymphokine genes). The decay of ribozyme activity seen 48 hrs post transfection time may be due to the overexpression of the TNF-α gene due to the long exposure to the plastic and/or the decay of the ribozyme itself.

Conclusions

We have demonstrated that TNF-α ribozymes are unusually stable inside human cells. This phenomenon is not easily explained in terms of intracellular location, since the ribozymes appear to be distributed throughout the cells (FIG. 6). A significant fraction of the ribozymes was recovered as a complex having reduced electrophoretic mobility. Suppression of the ribonucleases by RNAsin increases the recovery of the complexes from cytoplasmic extracts. Addition of tRNA had no competitive effect. Inhibition of complex formation was achieved with only unlabelled ribozyme. Neither integrase nor IL-2 ribozymes formed detectable complexes; thus, the binding is specific for TNF-α ribozyme. The IL-2 ribozyme showed a reduced intracellular stability compared to the TNF-α ribozyme, raising the possibility that complex formation is related to stability.

The linkage of TNF-α ribozyme to IL-2 ribozyme both increased stability and conferred the ability to form complexes to the double ribozyme. Further, the linked ribozymes were active.

A 3' end truncated ribozyme binds to proteins. In contrast 5' truncated TNF-α ribozyme does not form protein complexes. Thus, the capacity of any ribozyme to bind to protein(s) will depend on its 5' and perhaps 3' base composition as well as the length. The data presented herein should help in the designing of such a ribozyme which binds endogenous protein(s).

Example 2: Catalysis of hammerhead ribozymes in complex with glyceraldehyde-3-phosphate dehydrogenase A cytoplasmic tumour necrosis factor alpha ribozyme (TNF-α-Rz) binding protein has been purified and identified by N-terminal microsequencing to be the enzyme glyceraldehyde-3-phosphate dehydrogenase (GAPDH) which is active in the glycolytic pathway. Localization studies of GAPDH in peripheral blood mononuclear cells by immunofluorescence showed that GAPDH is also present in the nucleus of the cells. GAPDH has also been shown to be involved in other cellular functions such as protein phosphorylation, interaction with microtubules, and DNA repair. Binding of GAPDH to the TNFα-Rz was inhibited by NAD+, NADH and ATP in a concentration dependent manner, suggesting that the Rossmann fold structure is an RNA binding site. Cleavage of an RNA target sequence by hammerhead ribozymes is enhanced 0.5 to 20-fold upon addition of GAPDH to the reaction mixture. In contrast, no significant stimulation was observed with other nonspecific proteins such as lactate dehydrogenase. The catalytic activity of ribozymes was enhanced by GAPDH. This effect was found to be related to its helix destabilizing property, since structural problems of ribozymes as well as the substrate can be overcome by the addition of the protein. The GAPDH also increased the dissociation of RNA products from the ribozyme. Interestingly, in vitro nonspecific interaction of the GAPDH with RNA was found to be adequate for cleavage enhancement. However, in vivo experiments suggested that a specific interaction of GAPDH with the ribozymes is more advantageous for the GAPDH activity. Taken together the present data indicate a novel function for GAPDH involving RNA catalysis. The universal presence of GAPDH in all different cell types and its potential specific interaction with hammerhead ribozymes provides a new basis for the development of strategies to suppress gene expression in vivo with transacting ribozymes or other gene therapy methods.

Introduction

Ribozymes are RNA molecules with enzymatic activity (Forster and Symons, (1987), Cell, 49:211–220; Cech, (1987), Science, 236:1532–1539; Ulhenbeck, (1987), Nature, 328: 596–619); Haseloff and Gerlach, (1988), Nature, 334:585–591). Ribozyme-mediated cleavage in trans was demonstrated in vitro by Ulhenbeck (1987) and subsequently by Haseloff and Gerlach (1988). The trans-cleavage reaction catalyzed by hammerhead ribozymes has offered a potentially important way to inactivate intracellular RNA target from almost any gene whose nucleotide sequence is known (Cotten and Birnstiel, (1987), EMBO J., 8:3861–3866; Cameron and Jennings, (1989), Proc. Natl. Acad. Sci., U.S.A., 86:9139–9143; Sarver et al., (1990), Science, 247:1222–1225; Sioud and Drlica, (1991), Proc. Natl., Acad. Sci., U.S.A., 88: 7303–7307; Sioud et al., (1992), J. Mol. Biol., 223:831–835). However, the stability of RNA molecules within the cell, together with turnover and localization of the ribozyme, are distinguishing parameters that are expected to be important for the application of ribozymes as therapeutic agents, especially in diseases caused by RNA retroviruses. It has been demonstrated that intracellular stability of a ribozyme can be improved with modifications of the nucleotide sequence. Several groups have addressed this issue by either using modified nucleotides or by substituting non-critical regions of the ribozyme with DNA (Paolella et al., (1992), EMBO J., 11:1913–1919; Taylor et al., (1992), Nucleic Acids Res., 20:4559–4565; Hendry et al., (1992), Nucleic Acids Res., 21:573–5741). We have been more interested in studying how modifications that involve naturally occurring nucleotides as well as endogenous cellular proteins affect stability and activity of hammerhead ribozymes in human cells (Sioud et al (1992), J. Mol. Biol., 223:831–835; Sioud, (1994), J. Mol. Biol., 242:619–629). Our interest in endogenous cellular proteins is based upon their ability to enhance stability and catalytic activity of RNA both in vitro and in vivo as well as their potential effect on the cellular localization of RNAs (Guddat et al., (1990) Cell, 60:619–628; Moore et al., (1993) In the RNA World, Laboratory Press). Catalytic RNA complexed with protein exists in nature (for review see Ahsen and Schroeder, (1993), BioEssays, 15:299–307). The two best known examples are RNase P and small nuclear ribonucleoprotein particles (snRNPs). In eubacteria, RNase P is found as a ribonucleoprotein (Kole & Altman, (1981) Biochemistry, 20:1902–1906). However in vitro, its RNA subunit (M1 RNA) has catalytic activity (Guerrier-Takada et al., (1983) Cell, 60:35:849–857; Reich et al., (1988) Science 239:178–181; Forster & Altman, (1990) Science, 249: 783–786; Li et al., (1992) Proc. Natl. Acad. Sci. U.S.A. 89: 3185–3189).

During pre-mRNA splicing, the removal of introns requires participation of six different snRNPs (U1, U2, U3, U4, U5, and U6) (Moore et al. (1993), In the RNA World. Cold Spring Harbor, Cold Spring harbor Laboratory Press, New York pp. 303–357; Lamm & Lamond, (1993), Biochem. Biophys. Acta, 1173:247–265). Cis-splicing takes place within a large macromolecular complex known as the spliceosome where proteins have been found to play a specific role in splice site selection (Dreyfuss et al., (1993) Ann. Rev. Biochem., 62:289–321; Moore et al., (1993), In the RNA World. Cold Spring Harbor, Cold Spring Harbor Laboratory Press, New York, pp. 303–357; Wu and Maniatis, (1993), Cell, 75:1061–1070; Brosi et al., (1993), Science, 262:102–105). The binding of protein to catalytic RNA may have a beneficial effect in general. This view has been supported by the recent finding that non-specific RNA binding protein derived from the p7 nucleocapsid (NC) protein of the HIV-1 and the hnRNP A1 protein enhanced the hammerhead ribozyme cleavage activity in vitro (Tsuchihashi et al., (1993), Science, 262: 99–102; Herschlag et al., (1994), The EMBO. J., 13:2913–2924; Bertrand and Rossi, (1994), 13:2904–2912). Furthermore, the effects of A1 and NCp7 on the different steps of the cleavage reaction were found to be affected by the length of the ribozyme-substrate duplex.

Previously we have observed that a TNFα-Rz was more stable in vivo than IL2-ribozymes (IL-2-Rz) despite their comparable length and transfection efficiency. This unexpected stability was found to correlate with the ribozyme's capacity to bind cellular proteins, especially a 40 kDa protein detected by UV crosslinking (Sioud, (1994), J. Mol. Biol., 242:619–629; Sioud et al., (1994) Nucleic Acids Res. 22:5571–5575). We have now identified this major TNF-α-Rz binding protein as GAPDH both at the sequence and antigenic level. Furthermore, we have demonstrated that in contrast to nonspecific proteins, GAPDH has the ability to stimulate the cleavage activity of hammerhead ribozymes. This increase in activity is most likely due to the helix destabilizing activity of GAPDH. Thus, it is possible that GAPDH may serve additional biochemical functions in the regulation of RNA metabolism such as stability, translation and catalysis.

Materials and Methods

Ion exchange chromatography of the cytoplasmic protein prepared from PBMN cells

Cytoplasmic protein extracts from PBMN cells were fractionated through an HPLC ion exchange column (Mono Q) that was pre-equilibrated with buffer I (20 mM HEPES, pH 7.5). Protein extracts (5 mg) were loaded onto the column in buffer I and eluted with a linear gradient ranging from 0 to 1M NaCl in buffer I. Fractions of 0.5 ml were collected and dialyzed against 50 mM HEPES or Tris buffer pH 7.5. Following dialysis each fraction was analyzed by SDS-PAGE as described by Laemmli (1970) Nature, 227:680–682, and assayed for binding to the TNF-α-Rz as described by Sioud (1994) Nucleic Acids Res. 22:5571–5575.

Gel mobility shift assays

The ability of the 37 kDa protein to bind to TNF-αRz and its derivatives was investigated as previously described (Sioud, 1994). Briefly, the protein (0.1 or 0.2 μg) was incubated for 25 minutes at room temperature with [$^{32}$P]-labelled RNA molecules (5 ng) in a reaction mixture containing 20 mM HEPES, 100 mM KCl, 0.2 mM EDTA, 2% (v/v) glycerol, 0.5 mM PMSF and 0.5 μg E. coli tRNA. Following incubation, the RNA protein complexes were separated on 6% (w/v) polyacrylamide gels with 22.5 mM Tris-borate buffer (pH 8.0) and 1 mM EDTA. For competition assays, the reactions were preincubated with various concentrations of unlabelled competitor for 10 minutes before adding [$^{32}$P]-labelled TNFα-Rz.

N-terminal sequencing

N-terminal protein sequencing of the purified protein was done by Prof. K. Sletten at the Biotechnology Center, University of Oslo. 100 μg of purified protein was analyzed by automatic Edman degradation on an applied Biosystem 477A protein sequencer (Applied Biosystems, Foster City, Calif.) with an on-line 120A phenylthio-hydrantion amino acid derivative analyzer.

Ribozyme RNAs

The RNAs used in this study are cited below, some of them have been described earlier by Sioud (1994). [$^{32}$P]-labelled RNAs were synthesized by in vitro transcription using purified DNA templates and T7 RNA polymerase as described by Promega.

TNF-α-Rz: (SEQ ID NO: 34)
5' GUAAGAUGAUCUCUGAUGAGUCCGUGAG-GACGAAACUGCCUGGUAC Ugaauu3'
IL-2-Rz1 (SEQ ID NO: 35):
5' GGUGCAAUGCAACUGAUGAGUCCGUGAG-GACGAAACAGGAgaauu3'
IL-2-Rz2 (SEQ ID NO: 36):
5' GGUGCAATGCAACUGAUGAGUCCGUGAG-GACGAAACAGGAGUUGCgaauu3'
IL-2-Rz3 (SEQ ID NO: 37):
5'GACUUAGUGCAAUGCAACUGAUGAGUC-CGUGAGGACGAAACAGGAGUUGCgaauu3'
Potential binding site for GAPDH (PB-RNA): (SEQ ID NO: 38):
5' GUAAGAUGAUCUCUGAUGAGUCCGUGAG-Gaauu 3'
IL-2-Rz linked to the 3'end of the PB-RNA (IL-2-PB-Rz): (SEQ ID NO: 39):
5' GUAAGAUGAUCUCUGAUGAGUCCGUGAG-GAAAAAGACUUAGUG CAAUG-CAACUGAUGAGUCCGUGAGGAGCGAAA-CAGGAGUUGCgaauu3'
other RNA sequences such as IL-2-Rz3 linked TNFα-Rz (IL-2TNFα-Rz) and IL-2-Rz3 linked to a Δ3' TNF-α-Rz (IL-2 Δ3' TNF-α-Rz) have been previously described by Sioud (1994).

In vivo activity of the IL-2 ribozymes

The in vitro transcribed ribozymes were delivered to the cells by use of cationic liposomes (DOTAP). Analysis of the ribozyme accumulation indicated that after 20 hrs of transfection, the ribozyme concentration within the cells was constant and remained the same for more than 30 hrs (steady state). Thus, following 20 hrs transfection time the IL-2 gene expression was induced by PHA for an additional 12–16 hrs. The amount of expressed IL-2 protein was determined with CTLL-2 assay as described previously (Sioud, 1994) as well as by an enzyme amplified sensitivity immuno-assay (EASIA, Medgenix).

Effect of GAPDH on the in vitro ribozymes cleavage activity

Standard cleavage reactions were carried out at 37° C. in buffer containing 50 mM Tris-HCl, pH 7.5 and 10 mM MgCl$_2$. Multiple turnover cleavage reactions in the presence or absence of GAPDH were performed with 5 mM MgCO$_2$, unless otherwise indicated. Ribozyme and substrate were heated separately at 90° C. for 1 min and cooled at 4° C. After this step both RNAs were mixed in cleavage buffer containing 0.2 U RNasin and then divided into 3 samples. Following addition of GAPDH or lactate dehydrogenase (LD) as an unspecific protein to one of the samples, reactions were initiated by the addition of MgCl$_2$. At specified times, 10 μl aliquots were removed and the reaction was stopped by the addition of 20 mM EDTA and phenol. Following a phenol extraction, the reaction products were separated via denaturing gel electrophoresis on 15% urea gels, and quantified by Phosphor-Imager (FUJIX BAS 1000).

Localization of GAPDH in PBMN cells

PBMN cells were attached to glass slides by cytospin centrifugation and fixed in 100% ethanol. After incubation at 37° C. for 30 minutes with pre-immune and immune rabbit serum to the 37 kDa purified protein, the cells were washed with PBS and phycoerythrin conjugated anti-rabbit IgG was added. The cells were subsequently incubated as above. After washing, the cells were examined by Lietz Aristoplan's microscope and photographed using MPS 46 Photoautomat.

Results

Identification of a ribozyme binding protein in peripheral blood mononuclear (PBMN) cell extracts as GAPDH There is a general consensus that proteins which have an affinity for DNA or RNA may be involved in nucleic acid metabolism or in the control of gene expression. Such proteins have been partially purified from crude extracts by chromatography on nucleic acid-cellulose columns (Janson & Ryden, (1989) Protein purification, VCH Publishers (UK) Ltd., Cambridge, United Kingdom). In contrast, the TNF-α-Rz binding protein described here was purified to homogeneity from PBMN crude protein extracts using one single Mono Q chromatography column (FIG. 24A). The protein complexity and the TNF-α-Rz binding activity in the various chromatographic fractions were monitored by SDS polyacrylamide gel electrophoresis (SDS-PAGE) and mobility shift assay, respectively. As can be seen from FIG. 24B, single TNF-α-Rz binding activity was recovered in fractions 8–11. The binding activity correlated with the presence of an approximately 37 kDa protein in each fraction (FIG. 24B and 24C). The examination of silver stained SDS-PAGE gels, an example of which is shown in FIG. 24C, indicated that fractions 8 and 9 contained a homogenous 37 kDa protein. This protein, as indicated by the arrow (FIG. 24C), was likely to be the major cytoplasmic protein which bound to the TNFα-Rz (Sioud, 1994).

The 37 kDa protein in fraction 8 and 9 was purified in a sufficient quantity for microsequencing. The peptide sequence was found to contain the sequence VKVGVNG-FGRIG (SEQ ID NO: 33). A database search indicated that this peptide is present within the $NH_2$ terminal region of GAPDH, a 37 kDa enzyme which is active in the glycolytic pathway. Moreover, commercial preparations of GAPDH from human erythrocytes or muscle rabbit reacted strongly with rabbit polyclonal serum raised against our purified protein. Indirect immunofluorescence experiments using this polyclonal serum indicated that the protein was present both in the cytoplasm and in the nucleus of the cells (FIG. 25A and 25B).

Using crude protein extracts, we found that the binding activity present in cytoplasmic and nuclear protein extracts was more specific for TNF-α-Rz than for other ribozymes and RNA antisense (Sioud, 1994). Moreover, we have found that the binding protein may recognize a putative folded structure that involves the interaction of the 5' end of the TNFα-Rz with its catalytic domain (PB-RNA=potential protein RNA binding site). When this structure was linked to the IL-2-Rz, the resulting RNA construct IL-2-PB-Rz bound strongly to the protein from crude extracts. Similarly, the purified 37 kDa protein or a commercial preparation of GAPDH from human erythrocytes bound preferentially to TNF-α-Rz and its derivatives compared to other RNA (FIG. 26A, 26B and 26C).

GAPDH binding to TNF-α-Rz is not competed by excess IL-2-Rzs or tRNA

It has been reported that GAPDH also binds to tRNA (Singh & Green, (1993) Science, 259:365–367). However, consistent with our previous experiments with crude extracts, the binding of the purified protein to TNF-α-Rz is not affected by a 240 fold excess of cold tRNA (FIG. 27A, lane 10) or 100 fold excess of IL-2-Rz (FIG. 27B, lane 10). In contrast, a 100 fold excess of cold TNF-α-Rz completely inhibited, via competitive inhibition, the binding of [$^{32}$P]-labelled TNF-α-Rz (FIG. 27A and 27B, both lane 6). Thus, indicating that the binding capacity of GAPDH to the TNFα-Rz was higher than that for tRNA and IL-2-Rz.

The Rossmann fold motif of GAPDH is a part of the ribozyme binding domain

The GAPDH functions as a homopolymer of four subunits, each containing a tight, but non-covalently bound coenzyme molecule ($NAD^+$) at the Rossmann fold motif (Rossmann et al., (1975) "Evolution and structural relationships among dehydrogenases." In The Enzymes (Boyer, P. D., ed.), pp. 61–102, Academic Press, New York). In order to study the involvement of such a structure on ribozyme binding we have performed competition experiments with $NAD^+$, NADH and ATP (FIG. 28). All compounds competed with the ribozyme binding, suggesting that the Rossmann fold motif is involved in ribozyme binding. Lactate dehydrogenase, which also contains the Rossmann fold motif, bound very weakly to the ribozyme, while other proteins without the Rossmann fold structure had no detectable ribozyme binding activity (data not shown). These results suggest that the conserved $NAD^+$ site is part of the GAPDH binding domain.

Effect of the GAPDH on TNFα-Rz cleavage activity

Figure 29D:
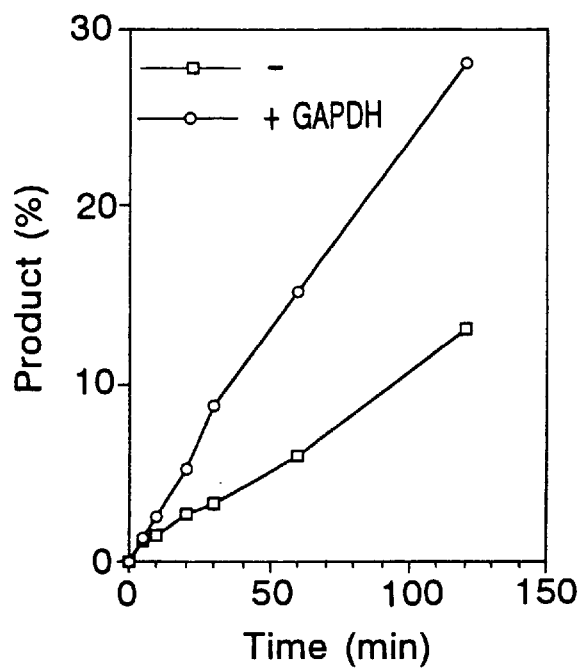

To analyze the effect of the purified 37 kDa protein as well as the commercial GAPDHs on hammerhead ribozyme catalytic function, we initially analysed the cleavage activity of TNF-α-Rz in the presence of different concentrations of GAPDH or nonspecific protein such as lactate dehydrogenase (LD). Cleavage enhancement by GAPDH is shown in FIG. 29 A. However, no significant effect on cleavage activity was observed with LD. Kinetic analysis of multiple turnover reactions in the presence of 100 ng/μl of GAPDH and 2 mM $MgCl_2$ (as shown in FIGS. 29B, 29C and 29D) indicate that the rate of the ribozyme cleavage increased by 3.8-fold upon addition of GAPDH.

The in vitro cleavage enhancement of the TNFα-Rz in the presence of purified protein was surprising, since under our conditions (low concentration of ribozyme vs protein) all of the ribozyme RNA molecules were thought to exist as ribozyme protein complexes. These results indicate that the interaction between the protein and the ribozyme exists at a minimum level during the catalysis. To test this, we examined whether the TNF-α target sequence (substrate) inhibits the binding of the protein to the TNF-α-Rz (FIG. 30). An assay was performed without magnesium in binding buffer. In contrast to IL-2 substrate, a 2-fold excess of the TNF-α-Rz substrate competed with GAPDH for binding to the ribozyme. This indicates that during the cleavage reaction, the substrate/ribozyme/GAPDH is a weak interaction.

Molecular mechanisms of reaction enhancement by GAPDH

We have noted the presence of an in vitro relationship between the effect of GAPDH on ribozyme catalysis and the expected secondary structure of the ribozyme. The binding of GAPDH to ribozymes may resolve misfolded RNA molecules that are structurally inactive. In order to see whether GAPDH can affect the structure of hammerhead ribozymes, we tested its effect on different IL-2 ribozymes directed against the same site on IL-2 mRNA. The binding of IL-2 ribozyme to the purified protein and to commercial GAPDH from human erythrocytes, was found to be weaker as compared to the TNF-α-Rz. However we noted that the binding of GAPDH from rabbit muscle to IL-2 ribozymes is much stronger than the commercial preparation of GAPDH derived from erythrocytes. Two of the IL-2 ribozymes (IL-2-Rz2 and IL-2-Rz3) contain a stable RNA duplex between their 5' and the 3' ends (FIG. 31A). This structure results in a low cleavage rate of IL-2-Rz2 and IL-2-Rz3 ($k_{cat}$=0.035 $min^{-1}$) compared to IL-2-Rz1 ($k_{cat}$=0.45 $min^{-1}$; FIG. 31 B).

If GAPDH, especially from rabbit, is capable of destabilizing the RNA duplex, then it may enhance the IL2-Rz2 activity, because binding of the IL-2-Rz2 or IL2-Rz3 to their substrate is rate limiting for these ribozymes. Kinetic quantification of IL-2-Rz2 cleavage rate (an example is shown in FIG. 32A, 32B, 32C, 32D and 32E) in the presence or absence of GAPDH from rabbit muscle, demonstrates that the IL-2-Rz2 cleavage rate increases by 15-fold upon addition of GAPDH, but not upon addition of LD. These results are consistent with GAPDH having the capacity to melt the secondary structure that exists in IL-2-Rz2. This structure will not limit the ability of the ribozyme to hybridize to its target and perform catalysis. Thus, a stable RNA secondary structure present in the ribozyme will not limit its activity in the presence of GAPDH. The cleavage enhancement by GAPDH on IL-2-Rz3 was found to be similar to IL-2-Rz2. However its effect on IL-2-Rz1 was found to be much lower (0.5 to 2-fold).

Control experiments (FIG. 32 E) suggest that the rate of cleavage enhancement is a result of the GAPDH protein.

Low cleavage occurred with the ribozyme in the absence of GAPDH (Lane 2). However more than 600 of the substrate was cleaved with added GAPDH (lane 3) and only the expected product was seen. Furthermore, omission of $Mg^{++}$ from the reaction mixture resulted in no detectable cleavage product or degradation product with added GAPDH, (Lane 4) and phenol extraction of the GAPDH preparation prior to addition abolished enhancement of the activity (Lane 5).

Effect of GAPDH on IL-2-Rz2 and IL-2-R3 DNA armed ribozyme activities

In order to understand how GAPDH enhances ribozyme catalysis, experiments were performed with IL-2-Rz2 and IL2-Rz3 DNA-armed ribozymes (FIG. 33A as an example) in the presence or absence of GAPDH. Cleavage rate analysis as shown in FIG. 33B and 33C, indicates a 2-fold increase of catalysis upon addition of GAPDH compared to a 15-fold increase for an RNA-armed ribozyme (see FIG. 32). This result suggested that GAPDH may destabilize RNA/RNA duplexes much better than DNA/DNA duplexes. When GAPDH and the ribozymes are mixed at 37° C., the absorbance at 260 nm of the mixture containing the RNA-armed IL-2-Rz increased by 40% compared to only 4% of the mixture containing the DNA-armed IL-2-Rz2.

Effect of GAPDH on cleavage activity of a more structurally stable ribozyme

As demonstrated previously (Sioud, 1994) the linkage of the potential RNA binding site of GAPDH to IL-2-Rz (IL-2-PB-Rz) leads to the formation of stable complexes similar to that found with TNF-α-Rz. The in vitro cleavage rate of IL-2-PB-Rz was found to be 8 to 10-fold less than the original ribozyme (IL-2-R1), indicating that there is in vitro structural problems with IL-2-PB-Rz (FIG. 34A). Addition of GAPDH to the reaction mixture overcame problems related to the structure of the ribozyme. Indeed, the cleavage rate of Il-2-PB-Rz increased by 15-fold upon addition of GAPDH (FIG. 34B).

In general GAPDH binds nonspecifically to RNA with low affinity, compared to TNFα-Rz and its derivatives and tRNA (Singh & Green, 1992). We have investigated whether this nonspecific binding of GAPDH to RNA in general affects hammerhead ribozymes catalysis. In order to answer this question we have used as a model a TNFα-Rz substrate that is structurally less accessible to the ribozyme. This was made by creating an RNA duplex between the 5' and 3' ends of the target (FIG. 35A). As can be seen from FIG. 35B, problems arising from this structure were partially overcome by the addition of the GAPDH. Cleavage enhancement of 4-fold was obtained upon addition of GAPDH (Lane 4).

Effect of GAPDH on product dissociation

Given the ability of GAPDH to destabilize the RNA duplexes, we have investigated whether GAPDH could lower the activation barrier of the dissociation products. In these experiments the IL-2-Rz 5' labelled cleavage products were directly annealed with the ribozyme. The complexes were separated from free products by native gel electrophoresis (FIG. 36, Lanes 1–5). The addition of GAPDH to a sample identical to the sample analysed in Lane 5 resulted in the dissociation of the 5'end products from the ribozyme (Lane 6). Under the same conditions, no dissociation was observed for the full length substrate, which suggests that the free energy of the RNA duplex is the rate limiting factor for GAPDH activity.

In viva ribozyme activities

As demonstrated above the interaction of GAPDH with RNA in solution was found to be adequate to allow the in vitro destabilizing activity of GAPDH. To evaluate the in vivo activity of GAPDH on ribozyme catalysis we have investigated the in vivo activity of IL-2-Rz1, IL-2-Rz2, IL-2-Rz3, IL-2-PB-Rz and D-IL2-Rz2 (D=DNA armed ribozyme). IL-2-PB-Rz binds more specifically to GAPDH than the three other IL-2 ribozymes. After a transfection period of 20 hours the recovery of ribozymes was constant. Thus, a steady state had been reached where the amount of incoming ribozyme molecules is similar to the in vivo rate of ribozyme decay. Under these conditions the in vivo IL-2-ribozyme activity does not depend upon stability, but rather their activity may be affected by other factors such as proteins. Data presented in FIG. 37 indicate that in vivo activity of IL2-Rz was higher than for the same ribozymes when DNA-armed. Additionally the in vivo activity of IL-2-PB-Rz was significantly higher than all IL-2 ribozymes tested. These results would suggest that GAPDH is interacting with hammerhead ribozymes in vivo and a specific binding of GAPDH to the ribozyme may be advantageous in the cells.

Discussion

In the present study, we have demonstrated that GAPDH is the protein in cytoplasmic extracts that preferentially binds to TNF-α-Rz and its derivatives. In addition to its potential protective effect as previously suggested (Sioud, et al., (1994) Nuc. Acids Res. 22:5571–5575), GAPDH was found to enhance the ribozyme cleavage activity in vitro and in vivo through helix destabilization. GAPDH functions as a homotetramer that converts glyceraldehyde-3-phosphate to 1,3-diphosphoglycerate. Previous studies have attributed to GAPDH a variety of other biological activities unrelated to glycolysis, such as protein phosphorylation, interaction with microtubules, DNA repair and transport of tRNA (summarized by Meyer-Siegler et al., (1991) Proc. Natl. Acad. Sci., U.S.A., 88:8460–8464; Singh & Green, (1993) Science, 259:365–368). The ability of GAPDH to interact with hammerhead ribozymes without blocking their cleavage activity suggests that GAPDH may have a functional role in RNA catalysis.

Recently, non-specific RNA binding proteins such A1 and NCp7, have been shown to facilitate ribozyme cleavage reactions in vitro (Tsuchihashi et al., (1993) Science, 262:99–102; Herschlag et al., (1994) EMBO J., 13:2913–2924; Bertrand & Rossi, (1994) EMBO J. 13:2904–4912). In contrast to these nonspecific RNA binding proteins GAPDH exhibits RNA sequence specificities. As for tRNA (Singh & Green, (1993) Science, 259:365–368), the binding of GAPDH to the TNF-α-Rz was found to involve an RNA secondary structure that could involve the interaction of the 5' end of the ribozyme with the catalytic domain (Sioud, 1994). Both purified GAPDH and commercial GAPDH from human erythrocytes bound more specifically to the TNFα-Rz and to the IL-2-Rz ribozyme linked to the PB RNA as compared to other RNA molecules. This is a protein that generally recognizes RNA with low affinity but can exhibit distinct sequence preferences which may be of significant biological importance. A previous study has shown that GAPDH is a specific tRNA-binding protein implicated in nuclear export of tRNA (Singh & Green, 1993) and in addition the protein most likely to be involved in increased stability of IL-2 mRNA in MLA 144 cells (Henics et al., 1994).

Stimulation of ribozyme catalysis by the purified protein preparation as well as by the commercial GAPDH from human erythrocytes or rabbit muscle was found to result from the helix destablizing properties of GAPDH (Karpel et al., (1981) Biochim. Biophys. Acta, 654:256–267). The multiple turnover rate for IL-2-Rz2 increases because of the destabilization of the short RNA duplex within the ribozyme. The helix destabilizing activity of GAPDH also was found to increase the dissociation of the reaction products. An RNA hybrid with a longer duplex (e.g ribozyme substrate) was not dissociated by the GAPDH under the same conditions where the 5' end cleavage product was dissociated. This suggests that the free energy of the RNA duplex binding is the rate-limiting factor for the activity of GAPDH. Given the capacity of GAPDH to melt RNA duplexes, GAPDH may be important for translation and reverse transcription where RNA secondary structure may interfere with the function of ribosomes and reverse transcriptases. GAPDH may also have an important role in providing ribozymes accessibility to their cleavage sites.

Some GAPDH effects have also been ascribed to NCp7 and hnRNB A1 proteins (Herschlag et al., (1994) The EMBO J. 13:2913–2924; Bertrand & Rossi, (1994) 13:2904–2912). A ribozyme-substrate combination which has a duplex length of, for example 17 or 20 bases, was inhibited 5-fold by NCp7 (Bertrand & Rossi, (1994) EMBO J. 13:2904–2912) and not stimulated with A1. The TNF-α-substrate hybrid length is either 15, 20 or 27 bases, yet GAPDH could increase its catalysis, suggesting that the unwinding activity of GAPDH is stronger than A1 or NCp7, and therefore more specific.

In contrast to the GAPDH protein, hnRNP A1 was found to have annealing activity (Meyeda et al., (1994) EMBO J. 13:5483–5495). Given the ability of GAPDH to destabilize RNA duplexes, GAPDH may be important for RNA unwinding during translation and hnRNPA1 may be important for RNA annealing during splicing. Both proteins may compete for the same function. In contrast to the cleavage enhancement by GAPDH and A1 proteins (Bertrand & Rossi, 1994), the bacteriophage T4 gene 32 protein (gp30) has no significant effect on IL-2 ribozymes used in this study (data not shown), indicating that not all RNA binding proteins with helix-destabilizing activity can improve the activity of hammerhead ribozymes.

GAPDH interacts strongly with the TNFα-Rz, but does not alter the structure of the catalytic core of the ribozyme. This suggests that the molecular interaction between the ribozyme and GAPDH may require conformational changes upon the hybridization of the ribozyme to its target in order for cleavage to occur.

Our in vitro experiments suggest that an interaction which is not necessarily stable, between GAPDH and hammerhead ribozymes enhances the ribozyme catalytic activity through the helix destabilizing properties of GAPDH. In vivo experiments suggest that a high affinity binding site for GAPDH may localize the protein near the ribozyme, and therefore facilitate the interaction of GAPDH with the ribozyme. The in vivo activity of IL-2 ribozyme linked to the potential RNA binding site for GAPDH (IL-2-PB-Rz) was found to be higher compared to Il-2 ribozymes alone. This enhanced activity is unlikely to be due to the enhanced stability of IL-2-PB-Rz (Sioud, 1994), since our experiments were carried out at steady state. These results suggest the possibility of linking the ribozyme to a high affinity binding site for GAPDH in order to enhance the interaction between the ribozyme and the protein in vivo. In vitro experiments indicate that GAPDH destabilizes RNA/RNA duplexes much better than DNA/DNA duplexes. GAPDH enhanced the catalytic activity of IL-2-Rz2 (all RNA) 6 times more compared to the DNA-armed ribozyme (see FIGS. 32 and 33). Although the stability of DNA-armed ribozymes was higher than RNA-armed ribozymes, we showed that IL-2-Rz2 and IL-2-Rz3 are more active in vivo than the corresponding DNA-armed ribozymes. Therefore GAPDH, and possibly other cellular proteins, is providing catalytic enhancement specifically to the RNA-armed ribozymes.

AU binding proteins were found to affect mRNA stability by protecting the AUUUA-rich RNA against degradation by transacting nuclear matrix-associated endoribonuclease V. The presence of AUUUA motifs are important for the stabilizing effect of AUB proteins (Werner et al., (1992) J. Mol. Biol. 226:721). Since AUUUA motifs are recognized by many proteins including hnRNP A1 and GAPDH, it is possible that GAPDH and A1 may compete for the same RNA motif. In contrast to the AUUUA motifs that are cleaved specifically by the endoribonuclease V (Werner et al., 1992), a high affinity binding site for GAPDH, such as the PB-RNA (Sioud, 1994) and tRNA (Singh & Green, 1993), would not be a binding site for any special ribonucleases. Thus, a free RNA carrying the PB-RNA would be more stable than an RNA carrying the AUUUA motifs.

The identification of an enzyme which functions in the glycolytic pathway as a potential specific ribozyme binding protein with protective and stimulative effects was unexpected. However, there are several multi-functional proteins that are involved in RNA biogenesis, such as tyrosyl-tRNA synthetase, which also function as a splicing factor for mitochondrial group I introns (Mohr et al., (1992) Cell, 69:483–494). The RNA binding proteins involved in splicing, storage and transport of RNA contain single or multiple copies of a homologous amino-acid sequence such as the arginine-rich RNA binding domain (Query et al., (1989) Cell, 57:89–101; Eriani et al., (1990) Nature, 347:203–206; Nagai et al., (1990) Nature, 348:515–520; Burd & Dreyfuss, (1994) Science, 265:102–105). The GAPDH amino acid sequence shows no obvious homology with any of these well-characterized RNA binding motifs, indicating that the nature of the interaction of GAPDH with RNA may involve novel structural elements. The NAD$^+$, NADH and ATP competition experiments suggest that the Rossman fold is capable of binding to RNA. Hydrophobic interactions have been shown to be important for the Rossman fold (Rossmann et al., (1975) The Enzymes, (Boyer, P. S. ed.) pp. 61–102, Academic Press, New York). With regard to this, we have observed that the capacity of the ribozyme to bind the GAPDH was not affected by pH, highlighting the importance of hydrophobic interactions between the TNFα-Rz and the NAD$^+$ binding site. We have found that the GAPDH binding activity can be blocked by idioacetate, which suggests that alterations in the redox state of GAPDH might regulate its interaction with RNA and thus its catalytic activity.

Our results suggest GAPDH has a functional role in RNA stability and catalysis. It may be advantageous to link the ribozyme to a high affinity binding site for GAPDH which would facilitate the in vivo interaction between the protein and the ribozyme. These findings may improve the general usefulness of ribozymes as therapeutic agents.

What is claimed is:

1. A composition comprising a first RNA covalently linked to a second RNA, wherein the second RNA molecule comprises at least the following sequence: 5' GUAA-GAUGAUCUCUGAUGAGUCCGUGAGG 3' (SEQ ID NO:38).

2. The composition of claim 1, wherein the first RNA comprises a ribozyme or an antisense RNA.

3. The composition of claim 2, wherein the ribozyme or the antisense RNA comprises ribonucleotides each of which may be unmodified or modified or substituted in its sugar, phosphate or base.

4. The composition of claim 2, wherein the ribozyme is a TNF-α ribozyme.

5. A method of stabilizing an RNA which comprises covalently linking to such RNA a second RNA which comprises ribonucleotides having at least the following sequence: 5' GUAAGAUGAUCUCUGAUGAGUC-CGUGAGG 3' (SEQ ID NO:38).

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: (Mixed DNA/RNA oligomer
            see specification and figures for details)

( x i ) SEQUENCE DESCRIPTION: SEQ ID NO:1:

NAAGAUGAUC UCUGANGANN NNNNNNNNN GAAACUGCCU GGN　　　　　43

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: (Mixed DNA/RNA oligomer
            see specification and figures for details)

( x i ) SEQUENCE DESCRIPTION: SEQ ID NO:2:

AAGAUCUACU GCCUGG　　　　　16

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: (Mixed DNA/RNA oligomer
            see specification and figures for details)

( x i ) SEQUENCE DESCRIPTION: SEQ ID NO:3:

AAGAUGAUCU CUGAUGANNN NNNNNNNNG AAACUGCCUG GN　　　　　42

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:4:

AAGAUGAUCU CUGAUGAGUC CGUGAGGACG AAACUGCCUG GN　　　　　42

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: (Mixed DNA/RNA oligomer
            see specification and figures for details)

( x i ) SEQUENCE DESCRIPTION: SEQ ID NO:5:

NAAGAUGAUC UCUGANGANN NNNNNNNNN GAAACUGCCU GGN     43

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:6:

NAAGAUGAUC UGACUGCCUG GN     22

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:7:

AAGAUGAUCU ACUGCCUGG     19

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:8:

NNCUGANGAN NNNNNNNNN NGAAAN     26

( 2 ) INFORMATION FOR SEQ ID NO:9:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

GUGCAAUGCA ACUGAUGAGU CCGUGAGGAC GAAACAGGAG AAAAAGAUGA UCUCUGAUGA     60

GUCCGUGGGG ACGAAACUGC CUGGAAUU     88

( 2 ) INFORMATION FOR SEQ ID NO:10:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

GAAAUGAUCU CUGAUGAGUC CGUGAGGACG AAACUGCCUG GAAAUGCAAU GCAACUGAUG     60

AGUCCGUGAG GACGAAACAG GAGAAUU                                                87

( 2 ) INFORMATION FOR SEQ ID NO:11:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:11:

GGUGCAAUGC AACUGAUGAG UCCGUGAGGA CGAAACAGGA GAAUUGAUGA UCUGACUGCC        60

UGGAAUU                                                                 67

( 2 ) INFORMATION FOR SEQ ID NO:12:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:12:

GGAUGAUCUG ACUGCCUGGA AUUGUGCAAU GCAACUGAUG AGUCCGUGAG GACGAAACAG        60

GAGAAUU                                                                 67

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:13:

NNCUGANGAN GAAAN                                                        15

( 2 ) INFORMATION FOR SEQ ID NO:14:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:14:

GAUGAUCUCU GAUGAGUCCG UGAGGACGAA ACUGCCUGGU GCAAUGCAAC UGAUGAGUCC        60

GUGAGGACGA AACAGGAGAA AAA                                               83

( 2 ) INFORMATION FOR SEQ ID NO:15:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:15:

GAGUACUAAG AUGAUCUCUG AUGAGUCCGU GAGGACGAAA CUGCCUGGUC UAGACAUAAC    60

CCCUUGGGGC CUCUAAACGG GUCUUGAGGG UUUUUUC    97

( 2 ) INFORMATION FOR SEQ ID NO:16:

( i ) SEQUENCE CHARACTERISTICS:
          ( A ) LENGTH: 33 base pairs
          ( B ) TYPE: nucleic acid
          ( C ) STRANDEDNESS: single
          ( D ) TOPOLOGY: linear ( i i ) MOLECULE TYPE: RNA (genomic)

( x i ) SEQUENCE DESCRIPTION: SEQ ID NO:16:

UCUGGCCCAG GCAGUCAGAU CAUCUUCUCG AAC    33

( 2 ) INFORMATION FOR SEQ ID NO:17:

( i ) SEQUENCE CHARACTERISTICS:
          ( A ) LENGTH: 53 base pairs
          ( B ) TYPE: nucleic acid
          ( C ) STRANDEDNESS: single
          ( D ) TOPOLOGY: linear ( i i ) MOLECULE TYPE: RNA (genomic)

( x i ) SEQUENCE DESCRIPTION: SEQ ID NO:17:

GAGUACUAAG AUGAUCUCUG AUGAGUCCGU GAGGACGAAA CUGCCUGGUC UAG    53

( 2 ) INFORMATION FOR SEQ ID NO:18:

( i ) SEQUENCE CHARACTERISTICS:
          ( A ) LENGTH: 46 base pairs
          ( B ) TYPE: nucleic acid
          ( C ) STRANDEDNESS: single
          ( D ) TOPOLOGY: linear ( i i ) MOLECULE TYPE: RNA (genomic)

( x i ) SEQUENCE DESCRIPTION: SEQ ID NO:18:

GUAAGAUGAU CUCUGAUGAG UCCGUGAGGA CGAAACUGCC UGAAUU    46

( 2 ) INFORMATION FOR SEQ ID NO:19:

( i ) SEQUENCE CHARACTERISTICS:
          ( A ) LENGTH: 69 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:19:

AACAGCTGTA ATACGACTCA CTATAGAGTA CTAAGATGAT CTCTGATGAG TCCGTGAGGA    60

CGAAACTGA    69

( 2 ) INFORMATION FOR SEQ ID NO:20:

( i ) SEQUENCE CHARACTERISTICS:
          ( A ) LENGTH: 72 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:20:

```
TTCTCGAGAA  AAAACCCTCA  AGACCCGTTT  AGAGGCCCCA  AGGGGTTATG  TCTAGACCAG        60

GCAGTTTCGT  CC                                                                72
```

( 2 ) INFORMATION FOR SEQ ID NO:21:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
AACAGCTGTA  ATACGACTCA  CTATAGAGTA  CTAAGATGAT  CTGACTGCCT  GGTCTAG         57
```

( 2 ) INFORMATION FOR SEQ ID NO:22:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
TTCTCGAGAA  AAAACCCTCA  AGACCCGTTT  AGAGGCCCCA  AGGGGTTATG  TCTAGACCAG        60

CA                                                                            62
```

( 2 ) INFORMATION FOR SEQ ID NO:23:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:23:

```
GGUGCAAUGC  AACUGAUGAG  UCCGUGAGGA  CGAAACAGGA  GAAUUNNNN                     49
```

( 2 ) INFORMATION FOR SEQ ID NO:24:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:24:

```
GGUGCAAUGC  AACUGAUGAG  UNCCGUNNNN  GAGGACGAAA  CANNGGAGAA  AAAGAUGAUC        60

UCUGAUGANN  NGUCCGUGAG  GACGAAACUC  CNUGGAAUUN  NNNNNN                       106
```

( 2 ) INFORMATION FOR SEQ ID NO:25:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:25:

GGUGCAAUGC AACUGAUGAG UCCGUGAGGA CGNAAACAGG AGUUAAGAUG AUCUGUUACU        60

GNCCUNNNGG AAUNNNNNNN NNNNNNNNNN                                        90

(2) INFORMATION FOR SEQ ID NO:26:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:26:

GUAAGAUGAU CUCUGAUGAG UCCGUGAGGA CGAAACUGCC UGGUACUAAC CCCUUGGGGC        60

CUCUAAACGG GUCUUGAGGG GUUUUUUGAA UU                                     92

(2) INFORMATION FOR SEQ ID NO:27:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:27:

GUAAGAUGAU CUCUGAUGAG UCCGUGAGGA CGAAACUGCC UGGUACUGAA GGCCAGCUCC        60

ACGUCCGGA UCAUGCUUUC AGUGCUCAUG AAUU                                    94

(2) INFORMATION FOR SEQ ID NO:28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:28:

GACUUAGUGC AAUGCAACUG AUGAGUCCGU GAGGACGAAA CAGGAGUUGC GAAUU             55

(2) INFORMATION FOR SEQ ID NO:29:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:29:

GUAAGAUGAU CUCUGAUGAG UCCGUGAGGA CGAAACUGCC UGGUAUGAAA AAAGACUUAG        60

UGCAAUGCAA CUGAUGAGUC CGUGAGGACG AAACAGGAGU UGCGAAUU                    108

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear ( i i ) MOLECULE TYPE: RNA (genomic)

( x i ) SEQUENCE DESCRIPTION: SEQ ID NO:30:

GCUGAUGAGU CCGUGAGGAC GAAACUGCCU GGUACUAAAU U 41

( 2 ) INFORMATION FOR SEQ ID NO:31:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:31:

GUAAGAUGAU CUCUGAUGAG UCCGUGAGGA CGAAGAAUU 39

( 2 ) INFORMATION FOR SEQ ID NO:32:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:32:

GAGUACUAAG AUGAUCUCUG AUGAGUCCGU GAGGACGAAA CUGCCUGGU 49

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Val Lys Val Gly Val Asn Gly Phe Gly Arg Ile Gly
1               5                   10

( 2 ) INFORMATION FOR SEQ ID NO:34:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:34:

GUAAGAUGAU CUCUGAUGAG UCCGUGAGGA CGAAACUGCC UGGUACUGAA UU 52

( 2 ) INFORMATION FOR SEQ ID NO:35:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:35:

| | |
|---|---|
| GGUGCAAUGC AACUGAUGAG UCCGUGAGGA CGAAACAGGA GAAUU | 4 5 |

( 2 ) INFORMATION FOR SEQ ID NO:36:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:36:

| | |
|---|---|
| GGUGCAATGC AACUGAUGAG UCCGUGAGGA CGAAACAGGA GUUGCGAAUU | 5 0 |

( 2 ) INFORMATION FOR SEQ ID NO:37:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:37:

| | |
|---|---|
| GACUUAGUGC AAUGCAACUG AUGAGUCCGU GAGGACGAAA CAGGAGUUGC GAAUU | 5 5 |

( 2 ) INFORMATION FOR SEQ ID NO:38:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

| | |
|---|---|
| GUAAGAUGAU CUCUGAUGAG UCCGUGAGGA AUU | 3 3 |

( 2 ) INFORMATION FOR SEQ ID NO:39:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

| | |
|---|---|
| GUAAGAUGAU CUCUGAUGAG UCCGUGAGGA AAAAGACUUA GUGCAAUGCA ACUGAUGAGU | 6 0 |
| CCGUGAGGAC GAAACAGGAG UUGCGAAUU | 8 9 |